(12) United States Patent
Abrams et al.

(10) Patent No.: US 8,252,832 B2
(45) Date of Patent: Aug. 28, 2012

(54) KINESIN INHIBITORS AS CANCER THERAPEUTICS

(75) Inventors: Tinya Abrams, Emeryville, CA (US); Paul Barsanti, Emeryville, CA (US); David Duhl, Emeryville, CA (US); Michel Faure, Emeryville, CA (US); Paul A. Renhowe, Danville, CA (US); Annette Olga Walter, Emeryville, CA (US)

(73) Assignee: Novartis AG, Basel (CH)

( * ) Notice: Subject to any disclaimer, the term of this patent is extended or adjusted under 35 U.S.C. 154(b) by 754 days.

(21) Appl. No.: 12/313,923

(22) Filed: Nov. 25, 2008

(65) Prior Publication Data

US 2009/0239922 A1 Sep. 24, 2009

Related U.S. Application Data

(60) Provisional application No. 61/013,966, filed on Dec. 14, 2007.

(51) Int. Cl.
*A61K 31/4174* (2006.01)
*C07D 233/64* (2006.01)

(52) U.S. Cl. .................................. 514/400; 548/338.1

(58) Field of Classification Search ................... 514/400; 548/338.1
See application file for complete search history.

(56) References Cited

U.S. PATENT DOCUMENTS

| 7,576,221 B2 * | 8/2009 | Wang et al. | 548/338.1 |
| 2006/0009472 A1 * | 1/2006 | Wang et al. | 514/255.05 |

FOREIGN PATENT DOCUMENTS

| WO | WO 2006/004924 | 1/2006 |
| WO | WO 2007/021794 | 2/2007 |
| WO | WO 2008/086122 | 7/2008 |

OTHER PUBLICATIONS

Patani et al., Bioisosterism: A Rational Approach in Drug Design, 1996, Chem. Rev., 96, 3147-3176.*
Pinkerton Anthony B "Imidazole based kinesin spindle protein inhibitors" Expert Opin Ther Patents 17 (7):875-878 (2007).

* cited by examiner

*Primary Examiner* — Kristin Bianchi
(74) *Attorney, Agent, or Firm* — Michael G. Smith

(57) ABSTRACT

The invention provides novel compounds having a substituted imidazole ring, and methods of using such compounds for the treatment of certain disorders such as hematological cancers and solid tumors. The compounds of the invention are tri-substituted imidazole derivatives that inhibit KSP. These compounds are also useful for the treatment of drug resistant tumors, such as solid tumors that express elevated levels of P-glycoprotein.

9 Claims, 7 Drawing Sheets

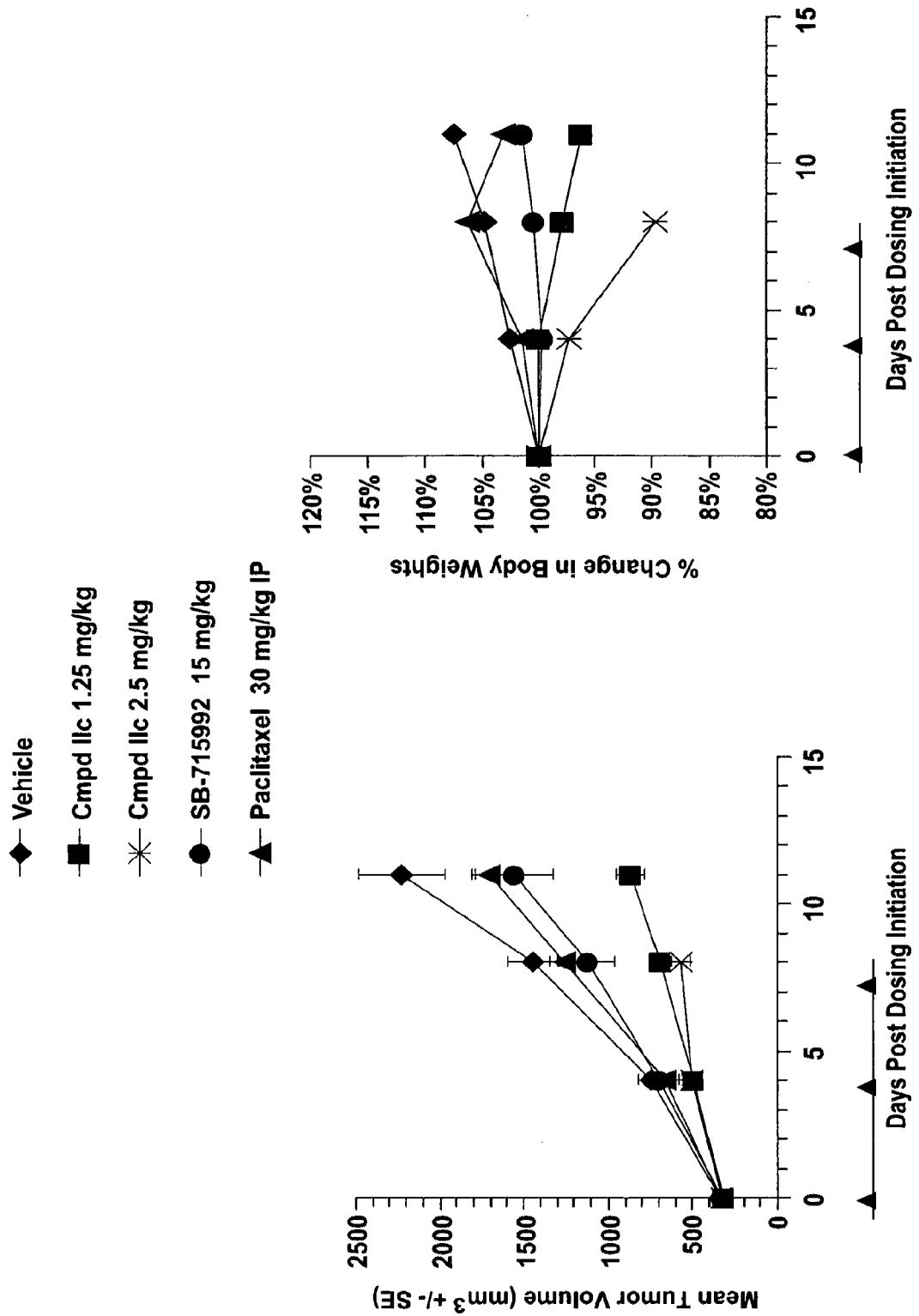

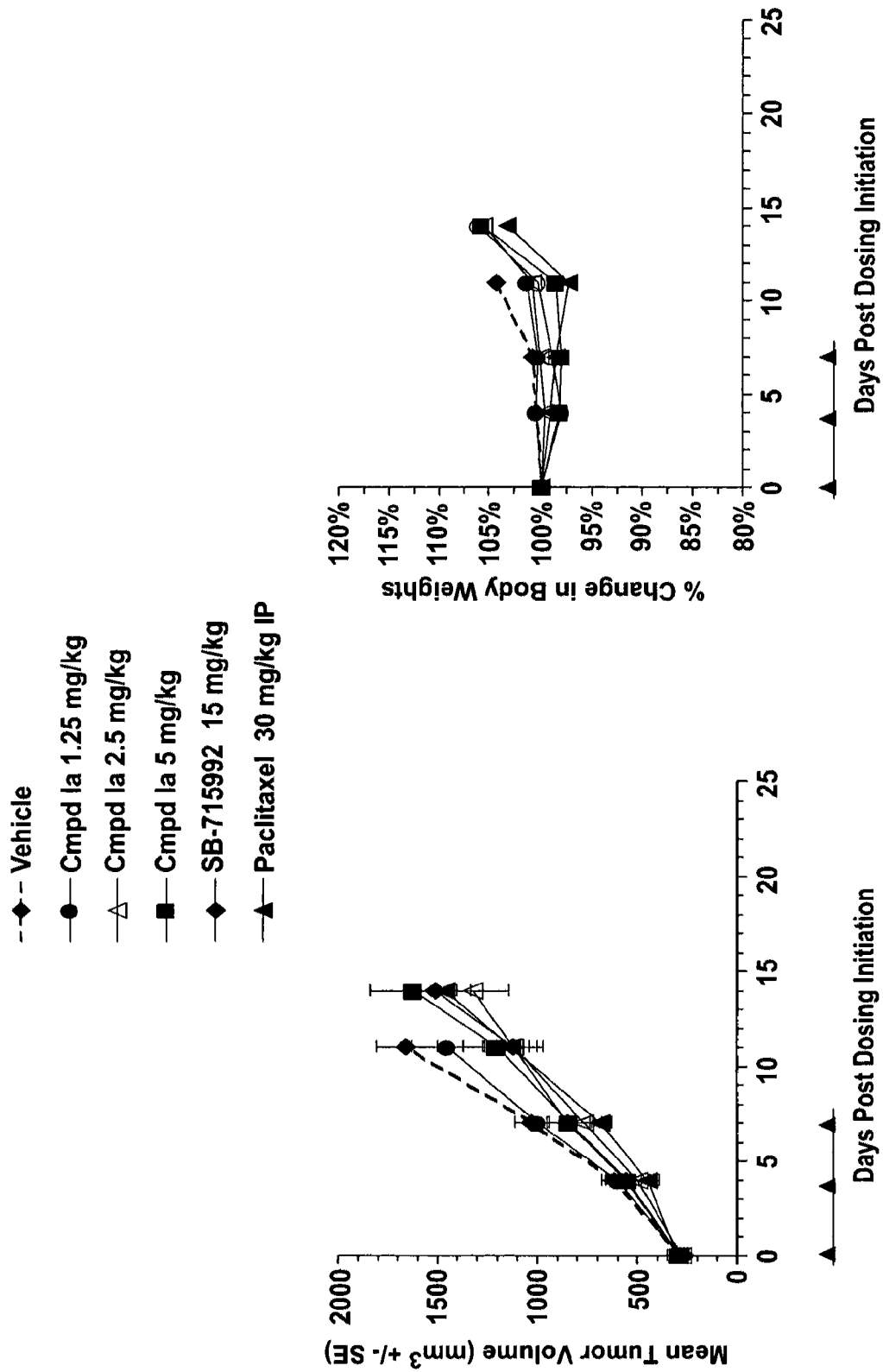

KINESIN INHIBITORS AS CANCER THERAPEUTICS

This application claims benefit of priority to U.S. Provisional Application No. 61/013,966, filed Dec. 14, 2007.

TECHNICAL FIELD

This invention relates to methods for treating proliferative disorders such as cancers by administering KSP inhibitors.

BACKGROUND

Kinesins are motor proteins that hydrolyze adenosine triphosphate as they travel along microtubules and generate mechanical force. These proteins are characterized by containing a motor domain having about 350 amino acid residues. The crystal structures of several kinesin motor domains have been resolved.

Currently, about one hundred kinesin-related proteins (KRP) have been identified. Kinesins are involved in a variety of cell biological processes including transport of organelles and vesicles, and maintenance of the endoplasmic reticulum. Several KRP's interact with the microtubules of the mitotic spindle or with the chromosomes directly and appear to play a pivotal role during the mitotic stages of the cell cycle. These mitotic KRP's are of particular interest for the development of cancer therapeutics.

Kinesin spindle protein (KSP) (also known as Eg5, HsEg5, KNSL1, or KIF11) is one of several kinesin-like motor proteins that are localized to the mitotic spindle and known to be required for formation and/or function of the bipolar mitotic spindle.

In 1995, the depletion of KSP using an antibody directed against the C-terminus of KSP was shown to arrest HeLa cells in mitosis with monoastral microtubule arrays (Blangy et al., Cell 83:1159-1169, 1995). Mutations in bimC and cut7 genes, which are considered to be homologues of KSP, cause failure in centrosome separation in *Aspergillus nidulans* (Enos, A. P., and N. R. Morris, Cell 60:1019-1027, 1990) and *Schizosaccharomyces pombe* (Hagan, I., and M. Yanagida, Nature 347:563-566, 1990). Treatment of cells with either ATRA (all trans-retinoic acid), which reduces KSP expression on the protein level, or depletion of KSP using antisense oligonucleotides revealed a significant growth inhibition in DAN-G pancreatic carcinoma cells indicating that KSP might be involved in the antiproliferative action of all trans-retinoic acid (Kaiser, A., et al., J. Biol. Chem. 274, 18925-18931, 1999). Interestingly, the *Xenopus laevis* Aurora-related protein kinase pEg2 was shown to associate and phosphorylate XlEg5 (Giet, R., et al., J. Biol. Chem. 274:15005-15013, 1999). Potential substrates of Aurora-related kinases are of particular interest for cancer drug development. For example, Aurora 1 and 2 kinases are over expressed on the protein and RNA level and the genes are amplified in colon cancer patients.

The first cell permeable small molecule inhibitor for KSP, "monoastral," was shown to arrest cells with monopolar spindles without affecting microtubule polymerization as do conventional chemotherapeutics such as taxanes and vinca alkaloids (Mayer, T. U., et al., Science 286:971-974, 1999). Monastrol was identified as an inhibitor in phenotype-based screens and it was suggested that this compound may serve as a lead for the development of anticancer drugs. The inhibition was determined not to be competitive with respect to adenosine triphosphate interaction with KSP, and was found to be rapidly reversible (DeBonis, S., et al., Biochemistry 42:338-349, 2003; Kapoor, T. M., et al., J. Cell Biol. 150:975-988, 2000).

In light of the importance of improved chemotherapeutics, there is a need for KSP inhibitors that are effective in vivo inhibitors of KSP and KSP-related proteins. Some inhibitors of KSP have been reported previously. For example, WO 06/002236 and PCT/US2006/031129 disclose certain classes of compounds indicated to be inhibitors of KSP. Ispinesib (SB-715992) is a clinical candidate from Cytokinetics that is indicated to act as a KSP inhibitor. The present invention provides new KSP inhibitors with improved activities and new methods of using these KSP inhibitors. In addition, it provides novel KSP inhibitors that are effective against cancer cells that are resistant to other therapeutic agents such as paclitaxel due to their expression of P-glycoprotein that acts as an efflux pump.

SUMMARY OF THE INVENTION

The invention provides a method for treating a proliferative disease selected from a solid tumor or a hematological cancer in a mammal comprising administering to said mammal a therapeutically effective amount of compound of structure I, a tautomer of the compound, a pharmaceutically acceptable salt of the compound, a pharmaceutically acceptable salt of the tautomer, or a mixture thereof, wherein the compound of structure I is

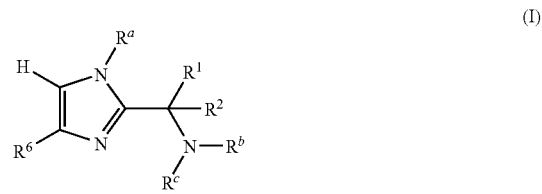

(I)

wherein:
$R^1$ is selected from the group consisting of aminoacyl, acylamino, carboxyl, carboxyl ester, aryl, and alkyl optionally substituted with hydroxy or halo;
$R^2$ is selected from the group consisting of hydrogen, alkyl, and aryl;
$R^a$ is L-$A^1$;
L is selected from the group consisting of —S(O)$_q$— where q is one or two, and $C_1$ to $C_5$ alkylene optionally substituted with hydroxy, halo, or acylamino;
$A^1$ is selected from the group consisting of aryl, substituted aryl, heteroaryl, substituted heteroaryl, heterocyclic, substituted heterocyclic, cycloalkyl, and substituted cycloalkyl;
$R^6$ is selected from the group consisting of heterocyclic, aryl and heteroaryl, all of which may be optionally substituted with —($R^8$)$_m$ where $R^8$ is as defined herein and m is an integer from 1 to 3;
$R^8$ is selected from the group consisting of cyano, alkyl, alkenyl, alkynyl, —CF$_3$, alkoxy, halo, and hydroxy; provided that when m is 2 or 3, each $R^8$ may be the same or different;
$R^b$ is either $R^4$ or $R^5$;
$R^4$ is selected from the group consisting of hydrogen, linear alkyl, -alkylene-aminoacyl, -alkylene-oxyacyl, -alkylene-acyloxy, -alkylene-hydroxy, -[alkylene]$_p$-nitrogen-containing heterocyclic, -[alkylene]$_p$-nitrogen-containing substituted heterocyclic, -[alkylene]$_p$-nitrogencontaining heteroaryl, -[alkylene]$_p$-nitrogen-containing substituted heteroaryl, and -[alkylene]$_p$-NR$^{10}$R$^{11}$ wherein p is 0 or 1, and the R$^4$ alkylene is a straight chained alkylene optionally mono- or disubstituted with one of the foregoing substituents selected from the group consisting of amino, substituted amino, hydroxy, alkyl, substituted alkyl, carboxyl, carboxyl ester, oxo, spirocycloalkyl, and halo;

R$^{10}$ and R$^{11}$ are independently selected from the group consisting of hydrogen, alkyl, substituted alkyl, —S(O)-alkyl, —S(O)-substituted alkyl, —S(O)$_2$-alkyl, —S(O)$_2$-substituted alkyl, heterocyclic, substituted heterocyclic, acyl, aryl, substituted aryl, heteroaryl, substituted heteroaryl, cycloalkyl, and substituted cycloalkyl, or when R$^{10}$ is hydrogen, R$^{11}$ is hydroxy, alkoxy, or substituted alkoxy;

R$^5$ is selected from the group consisting of hydrogen, alkyl, substituted alkyl, alkenyl, substituted alkenyl, alkynyl, substituted alkynyl, cycloalkyl, substituted cycloalkyl, heterocyclic, substituted heterocyclic, aryl, substituted aryl, heteroaryl, and substituted heteroaryl;

R$^c$ is selected from the group consisting of R$^3$ and —C(O)—N(R$^{13}$)(R$^{14}$);

R$^3$ is selected from the group consisting of hydrogen and —X-A, wherein X is selected from the group consisting of —C(O)—, —C(S)—, —S(O)—, —S(O)$_2$—, and —S(O)$_2$—N(R)—, where R is hydrogen or alkyl;

A is selected from the group consisting of hydrogen, optionally substituted alkyl, optionally substituted alkoxy, optionally substituted aryl, carboxyl, carboxyl ester, aminoacyl, optionally substituted heteroaryl, optionally substituted heterocyclic, and optionally substituted cycloalkyl, wherein the optionally substituted groups are substituted with 1 to 4 substituents selected from the group consisting of alkyl, substituted alkyl, alkoxy, substituted alkoxy, amino, substituted amino, aryloxy, substituted aryloxy, cyano, aryl, substituted aryl, heteroaryl, substituted heteroaryl, heterocyclic, substituted heterocyclic, heterocyclyloxy, substituted heterocyclyloxy, acyl, carboxyl, carboxyl ester, oxo (except when A is optionally substituted aryl or optionally substituted heteroaryl), halo, hydroxy, —S(O)$_2$—R$^9$ where R$^9$ is alkyl, substituted alkyl, aryl, substituted aryl, heteroaryl or substituted heteroaryl, and nitro; and R$^{13}$ and R$^{14}$ are independently selected from the group consisting of hydrogen, hydroxy, alkyl, substituted alkyl, cycloalkyl, substituted cycloalkyl, aryl, substituted aryl, heteroaryl, substituted heteroaryl, heterocyclic, and substituted heterocyclic provided that only 1 of R$^{13}$ or R$^{14}$ is hydroxy; or R$^{13}$ and R$^{14}$ together with the nitrogen atom pendent thereto join to form a heterocyclic or substituted heterocyclic.

In one embodiment, the invention provides a method for treating a proliferative disease selected from a solid tumor or a hematological cancer in a mammal comprising administering to said mammal a therapeutically effective amount of compound of structure I, a tautomer of the compound, a pharmaceutically acceptable salt of the compound, a pharmaceutically acceptable salt of the tautomer, or a mixture thereof, wherein said solid tumor is selected from the group consisting of lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, small cell lung carcinoma (SCLC), non-small cell lung carcinoma, pancreatic cancer, head and neck squamous cell cancer and sarcomas.

In another embodiment, the solid tumor is breast carcinoma. In a further embodiment, the breast carcinoma is metastatic breast carcinoma.

In one embodiment, the invention provides a method for treating a proliferative disease selected from a solid tumor or a hematological cancer in a mammal comprising administering to said mammal a therapeutically effective amount of compound of structure I, a tautomer of the compound, a pharmaceutically acceptable salt of the compound, a pharmaceutically acceptable salt of the tautomer, or a mixture thereof, wherein said solid tumor is gastric carcinoma.

In another embodiment, the solid tumor is prostate cancer. In one embodiment, the invention provides a method of treatment wherein the tumor is a multidrug resistant tumor. In another embodiment, the multidrug resistant tumor expresses an elevated level of P-glycoprotein. In some embodiments, treatment comprises use of a compound of formula (I) wherein:
  R$^1$ is a C1-C6 alkyl or cycloalkyl; and/or
  R$^2$ is H or a C1-C4 alkyl; and/or
  R$^6$ is an optionally substituted aryl group; and/or
  R$^a$ is an optionally substituted benzyl or arylmethyl group; and/or
  R$^b$ is amino-substituted C2-C6 alkylene, which may be further substituted by hydroxy, C1-C4 alkyl, C1-C4 haloalkyl, C1-C4 hydroxyalkyl, oxo, or halo; and/or
  R$^c$ is —X-A, where —X is —C(O)— and A is alkyl, which may be substituted with up to four groups selected from amino, halo, hydroxy, alkoxy, cyano, substituted amino, or S(O)$_2$R$^9$, where R$^9$ is C1-C4 alkyl.

In one embodiment, the invention provides a method for treating a proliferative disease selected from a solid tumor or a hematological cancer in a mammal comprising administering to said mammal a therapeutically effective amount of compound of structure I, a tautomer of the compound, a pharmaceutically acceptable salt of the compound, a pharmaceutically acceptable salt of the tautomer, or a mixture thereof, wherein said hematological cancer is selected from the group consisting of Hodgkin's lymphoma (HL), non-Hodgkin's lymphoma (NHL), leukemia, myelogenous leukemia, lymphocytic leukemia, acute myelogenous leukemia (AML), chronic myelogenous leukemia (CML), acute lymphocytic leukemia (ALL), chronic lymphocytic leukemia (CLL), myelodysplastic syndrome (MDS), hairy cell leukemia and multiple myeloma. The mammal may be a human.

In a further embodiment, the hematological cancer is acute myelogenous leukemia. In an alternate embodiment, the hematological cancer is multiple myeloma.

In preferred embodiments, the compounds of formula I have at least one of the following preferred structural features:

In some of these preferred embodiments, R$^1$ in the compound of formula I is a C1-C6 alkyl or cycloalkyl group.

In some of these preferred embodiments, R$^2$ in the compound of formula I is H or a C1-C4 alkyl.

In some of these preferred embodiments, R$^6$ in the compound of formula I is an optionally substituted aryl group; in certain embodiments, it is a halo-substituted phenyl ring.

In some of these preferred embodiments, R$^a$ in the compounds of formula I is an optionally substituted benzyl or arylmethyl (—CH$_2$-aryl) group; in certain embodiments, it is unsubstituted benzyl.

In some of these preferred embodiments, R$^b$ in the compound of formula I is amino-substituted C2-C6 alkylene, which may be further substituted by hydroxy, C1-C4 alkyl, C1-C4 haloalkyl, C1-C4 hydroxyalkyl, oxo, or halo.

In some of these preferred embodiments, $R^c$ in the compound of formula I is —X-A, where —X is —C(O)— and A is alkyl, which may be substituted with up to four groups selected from amino, halo, hydroxy, alkoxy, cyano, substituted amino, or $S(O)_2R^9$, where $R^9$ is C1-C4 alkyl.

In specific preferred embodiments, the compound of formula I comprises at least two of the preferred groups identified above for $R^1$, $R^2$, $R^6$, $R^a$, $R^b$ and $R^c$. In further embodiments, it comprises at least three of these preferred groups. In further embodiments, the compound of formula I comprises at least four of the preferred groups.

Further embodiments of compounds contemplated for use in methods of the invention are disclosed in WO2006/002236 entitled "Substituted Imidazole Derivatives" and published on Jan. 5, 2006, which publication is hereby incorporated by reference in its entirety. Still further embodiments of compounds are disclosed in PCT/US2006/031129 entitled "Substituted Imidazole Compounds As KSP Inhibitors" filed on Aug. 9, 2006, which is hereby incorporated by reference in its entirety. Still further embodiments of compounds are disclosed in U.S. Provisional Application No. 60/883,740, entitled Cyclized Derivatives as EG-5 Inhibitors and filed on Jan. 5, 2007, which is incorporated by reference in its entirety.

In another embodiment, a method is provided for treating a proliferative disease elected from a solid tumor or a hematological cancer in a mammal comprising administering to said mammal a therapeutically effective amount of compound of Formula II, a tautomer of the compound, a pharmaceutically acceptable salt of the compound, a pharmaceutically acceptable salt of the tautomer, or a mixture thereof, wherein the compound of Formula II is:

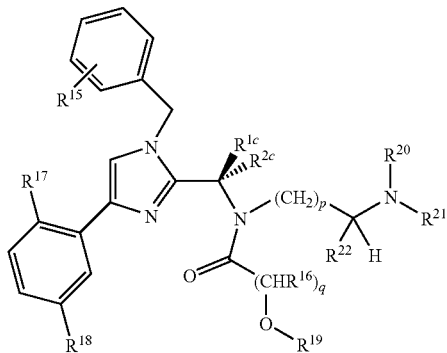

(II)

wherein:
$R^{1c}$ is selected from the group consisting of ethyl, isopropyl, t-butyl, phenyl, —CH(CH$_2$)$_2$O (oxetan-3-yl) and —CCH$_3$(CH$_2$)$_2$O (3-methyloxetan-3-yl);
$R^{2c}$ is hydrogen or methyl;
$R^{15}$, $R^{16}$, $R^{17}$ and $R^{18}$ are each independently selected from H, halo, C1-4 alkyl, C1-4 haloalkyl, and CN;
$R^{19}$, $R^{20}$ and $R^{21}$ are each independently H or optionally substituted C1-C10 acyl;
$R^{22}$ is C1-C4 haloalkyl;
p is an integer from 1 to 3; and
q is an integer from 1-3;
or a pharmaceutically acceptable salt thereof.

In some embodiments of the compounds of Formula II, $R^{1c}$ is selected from the group consisting of ethyl, isopropyl, and t-butyl;

$R^{2c}$ is H;
$R^{15}$, $R^{17}$ and $R^{18}$ are each independently selected from H, halo, C1-4 alkyl, C1-4 haloalkyl, and CN;
$R^{16}$ is H or C1-C4 alkyl;
$R^{19}$, $R^{20}$ and $R^{21}$ are each independently H or optionally substituted C1-C10 acyl;
$R^{22}$ is C1-C4 haloalkyl;
p is 2; and
q is 1.

These compounds also include the corresponding pharmaceutically acceptable salts.

The compounds of Formula II and Formula IIa-IIc (below) are a subset of the compounds of Formula I, and are characterized by the presence of a free hydroxyl group or a prodrug version of a free hydroxyl group in the acyl moiety, i.e., in these compounds, $R^{19}$ is H, or $R^{19}$ is an acyl group that can hydrolyze off in vivo to provide a compound wherein $R^{19}$ is H. The compounds wherein $R^{19}$ is a suitable acyl group are prodrugs that readily hydrolyze in the body to produce a compound where $R^{19}$ is H. Compounds wherein $R^{19}$ is H have been found to have surprisingly good activity for treating certain conditions like prostate cancer, and are particularly effective against tumors where P-gp is expressed and in certain hematological cancers. In particular, these compounds are effective against drug-resistant tumors expressing P-gp, a common resistance mechanism, while even very similar compounds without the hydroxyl are far less effective against such drug-resistant tumors. While it is common for a free hydroxyl to be an undesirable feature in a drug candidate due to metabolic issues such as oxidation and glycosylation, it was surprisingly found that compounds of Formula II or Ia, IIb or IIc, are more effective in vivo against certain tumors than similar compounds that do not contain a free hydroxyl and that cannot readily hydrolyze to provide a free hydroxyl ($R^{19}$=H). Their effectiveness against drug-resistant tumors makes these compounds of Formula II particularly useful for treating cancer.

In a further embodiment, a method for treating a proliferative disease selected from a solid tumor or a hematological cancer in a mammal comprising administering to said mammal a therapeutically effective amount of compound of formula II, a tautomer of the compound, a pharmaceutically acceptable salt of the compound, a pharmaceutically acceptable salt of the tautomer, or a mixture thereof, is provided wherein the solid tumor is selected from the group consisting of lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, small cell lung carcinoma (SCLC), non-small cell lung carcinoma, pancreatic cancer, brain cancer, head and neck squamous cell cancer and sarcomas. In certain embodiments, the tumor is a multi-drug resistant one, or one that expresses an elevated level of P-glycoprotein (P-gp).

In a further embodiment, a method is provided wherein the solid tumor is breast carcinoma. In a further embodiment, the breast carcinoma is metastatic breast carcinoma.

In an alternate embodiment, the solid tumor is gastric carcinoma. In a further embodiment, the solid tumor is prostate cancer. In one embodiment, the invention provides a method of treatment for a proliferative disease selected from a solid or hematological cancer comprising administration of Formula II wherein the tumor is a multidrug resistant cancer. In some embodiments, the hematological malignancy is selected from Acute myelogenous leukemia (AML), chronic myelogenous leukemia (CML), acute lymphoblastic leukemia (ALL), multiple myeloma (MM), non-Hodgkin lymphoma (NHL) and Hodgkin lymphoma (HL). In certain embodiments, the malignancy is a multi-drug resistant one, or one that expresses an elevated level of P-glycoprotein (P-gp).

In a further embodiment, a method for treating a proliferative disease elected from a solid tumor or a hematological cancer in a mammal comprising administering to said mammal a therapeutically effective amount of compound of formula II, a tautomer of the compound, a pharmaceutically acceptable salt of the compound, a pharmaceutically acceptable salt of the tautomer, or a mixture thereof, is provided wherein the hematological cancer is selected from the group consisting of Hodgkin's lymphoma (HL), non-Hodgkin's lymphoma (NHL), leukemia, myelogenous leukemia, lymphocytic leukemia, acute myelogenous leukemia (AML), chronic myelogenous leukemia (CML), acute lymphocytic leukemia (ALL), chronic lymphocytic leukemia (CLL), myelodysplastic syndrome (MDS), hairy cell leukemia and multiple myeloma.

In a further embodiment, a method is provided wherein said hematological cancer is acute myelogenous leukemia. In an alternate embodiment, the hematological cancer is multiple myeloma.

In another embodiment, a method is provided for treating a proliferative disease selected from a solid tumor or a hematological cancer in a mammal, where the method comprises administering to said mammal an amount of a KSP inhibitor of Formula (I) or Formula (II) and further comprises administering a second anticancer therapeutic. In one embodiment, the second anticancer therapeutic is given prior, along with, or following treatment with the KSP inhibitor of Formula (I) or Formula (II).

The second anticancer therapeutic can be selected from irinotecan, topotecan, gemictabine, imatinib, trastuzumab, 5-fluorouracil, leucovorin, carboplatin, cisplatin, docetaxel, paclitaxel, tezacitabine, cyclophosphamide, vinca alkaloids, anthracyclines, rituximab, and nilotinib.

In some embodiments, the second compound is a Bcr-Abl inhibitor.

In particular embodiments, the Bcr-Abl inhibitor is selected from the group of imatinib and nilotinib.

In still a further embodiment, the KSP inhibitor is a compound of formula (I) wherein:

$R^1$ is a C1-C6 alkyl or cycloalkyl; and/or $R^2$ is H or a C1-C4 alkyl; and/or $R^6$ is an optionally substituted aryl group; and/or $R^a$ is an optionally substituted benzyl or arylmethyl group; and/or $R^b$ is amino-substituted C2-C6 alkylene, which may be further substituted by hydroxy, C1-C4 alkyl, C1-C4 haloalkyl, C1-C4 hydroxyalkyl, oxo, or halo; and/or $R^c$ is —X-A, where —X is —C(O)— and A is alkyl, which may be substituted with up to four groups selected from amino, halo, hydroxy, alkoxy, cyano, substituted amino, or $S(O)_2R^9$, where $R^9$ is C1-C4 alkyl.

The invention provides a compound of formula (II):

(II)

wherein:
$R^{1c}$ is selected from the group consisting of ethyl, isopropyl, t-butyl, phenyl, —CH(CH$_2$)$_2$O (oxetan-3-yl) and —CCH$_3$(CH$_2$)$_2$O (3-methyloxetan-3-yl);
$R^{2c}$ is hydrogen or methyl;
$R^{15}$, $R^{16}$, $R^{17}$ and $R^{18}$ are each independently selected from H, halo, C1-4 alkyl, C1-4 haloalkyl, and CN;
$R^{19}$, $R^{20}$ and $R^{21}$ are each independently H or optionally substituted C1-C10 acyl;
$R^{22}$ is C1-C4 haloalkyl;
p is an integer from 1 to 3; and
q is an integer from 1-3;
or a pharmaceutically acceptable salt thereof.
In one embodiment, $R^{22}$ is fluoromethyl.
In another embodiment, p is 2.
In a further embodiment, q is 1.
In another embodiment, $R^{2c}$ and $R^{15}$ are each H.
In a further embodiment, $R^{17}$ and $R^{18}$ are each halo.
In yet another embodiment, $R^{19}$, $R^{20}$ and $R^{21}$ are each H.
In a further embodiment, $R^{19}$ is H.
In another embodiment, $R^{19}$ is optionally substituted C1-C10 acyl.
In some embodiments, the compound comprises two or more of the structural features described above for $R^{22}$, p, q, $R^{2c}$ and $R^{17}$-$R^{21}$. In some embodiments, the compound comprises at least three of these structural features. In some preferred embodiments of these compounds, $R^{22}$ is fluoromethyl, and p is 2, and q is 1, and $R^{2c}$ and $R^{15}$ are each H. In some such embodiments, $R^{17}$ and $R^{18}$ each represent F. And in some of these preferred embodiments, $R^{19}$, $R^{20}$ and $R^{21}$ are each H. Preferably in these embodiments, $R^{1c}$ is selected from ethyl, isopropyl and t-butyl.

The invention also provides a compound of formula IIa:

IIa or a pharmaceutically acceptable salt thereof.

The invention also provides a compound of Formula IIb:

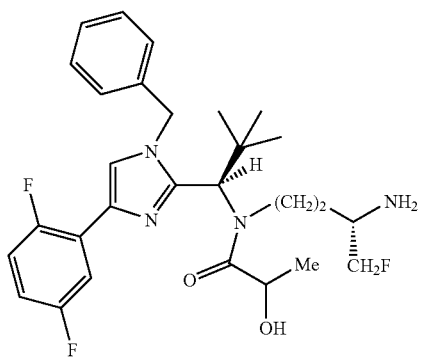

IIb or a pharmaceutically acceptable salt thereof.

The invention also provides a compound of formula IIc:

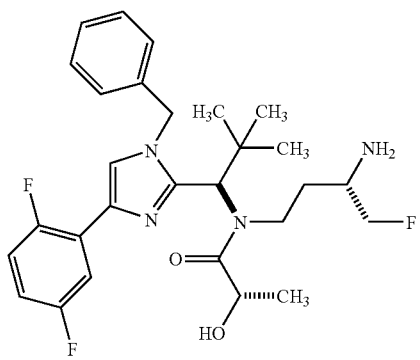

IIc (S)-N-((S)-3-amino-4-fluorobutyl)-N-((R)-1-(1-benzyl-4-(2,5-difluorophenyl)-1H-imidazol-2-yl)-2,2-dimethylpropyl)-2-hydroxypropanamide or a pharmaceutically acceptable salt thereof.

In one embodiment, the invention provides a method for treating a proliferative disease selected from a solid tumor or a hematological cancer in a mammal, where the method comprises administering to said mammal a therapeutically effective amount of compound of any one of formulas II, IIa, IIb or IIc, a tautomer of any one of these compounds, a pharmaceutically acceptable salt of any one of these compounds, a pharmaceutically acceptable salt of the tautomer, or a mixture thereof.

In a further embodiment, the solid tumor is selected from the group consisting of lung carcinoma, breast carcinoma, ovarian carcinoma, skin carcinoma, colon carcinoma, urinary bladder carcinoma, liver carcinoma, gastric carcinoma, prostate cancer, renal cell carcinoma, nasopharyngeal carcinoma, squamous cell carcinoma, thyroid papillary carcinoma, cervical carcinoma, small cell lung carcinoma (SCLC), non-small cell lung carcinoma, pancreatic cancer, head and neck squamous cell cancer, brain cancer, and sarcomas. In certain embodiments, the solid tumor is a tumor that is resistant to other cancer drugs. It can be a cancer that expresses an efflux pump, such as P-gp that promotes drug resistance, or a cancer that has been shown to be resistant to treatment with drugs like paclitaxel or SB-715992. Cancers that are resistant to drugs such as paclitaxel due to over expression by the cancer cells of an efflux pump, in particular P-glycoprotein (P-gp), are sensitive to compounds of formula II, as demonstrated herein, while similar compounds lacking the hydroxyl of the compounds of Formula II may not be effective in these drug resistant tumors. Compounds of formula Ia, IIb, and IIc are especially useful for the treatment of tumors that express P-gp and exhibit resistance to other therapeutic agents. These compounds are advantageous for this unexpected ability to treat drug-resistant tumors. Their activity on drug-resistant tumors is believed to be associated with the free hydroxyl on the amide moiety of Formula II.

In another embodiment, the solid tumor is breast carcinoma. In a further embodiment, the breast carcinoma is metastatic breast carcinoma.

In an alternate embodiment, the solid tumor is gastric carcinoma.

In another embodiment, the solid tumor is prostate cancer.

In each of these embodiments, the tumor is sometimes one that is resistant to other drugs. In some embodiments, the tumor is selected from kidney, liver, colon, brain or breast cancer. In certain embodiments, it is a tumor that expresses elevated levels of P-gp. Such elevated expression of P-gp can arise naturally or as a result of treatment with other drugs.

In another embodiment, the invention provides a method for treating a proliferative disease selected from a solid tumor or a hematological cancer in a mammal comprising administering to said mammal a therapeutically effective amount of compound of any one of formulas IIa, IIb or IIc, a tautomer of any one of these compounds, a pharmaceutically acceptable salt of any one of these compounds, a pharmaceutically acceptable salt of the tautomer, or a mixture thereof wherein the hematological cancer is selected from the group consisting of Hodgkin's lymphoma (HL), non-Hodgkin's lymphoma (NHL), leukemia, myelogenous leukemia, lymphocytic leukemia, acute myelogenous leukemia (AML), chronic myelogenous leukemia (CML), acute lymphocytic leukemia (ALL), chronic lymphocytic leukemia (CLL), myelodysplastic syndrome (MDS), hairy cell leukemia and multiple myeloma.

In another embodiment the hematological cancer is acute myelogenous leukemia.

In another embodiment, the hematological cancer is multiple myeloma.

BRIEF DESCRIPTION OF DRAWINGS

FIG. 6. Efficacy of compound IIc administered on a q4d×3 dose schedule in the KB8.5 tumor xenograft model. KB8.5 tumors were established in female athymic nu/nu mice (Charles River Laboratories) by subcutaneous injection of 5×10$^6$ cells in 0.2 mL of 1:1 ratio of HBSS and Matrigel™ into the right flank of each mouse. When tumors reached an average of 339 mm$^3$, mice were randomized based on tumor volumes into treatment groups (n=9). Animals were i.v. administered Compound IIc or SB-715992. Paclitaxel was administered at 30 mg/kg i.p. All were dosed on a q4d×3 schedule. (Left) Efficacy/tumor volumes of treatment groups vs. days post dosing initiation; (Right) Percent body weight change relative to initial weights on day of randomization/dosing initiation. Compound IIc at 1.25 mg/kg was statistically different from the vehicle group on day 11 (*$p<0.05$, ANOVA/Tukey's Test).

FIG. 7. Efficacy of compound IIa administered on a q4d×3 dose schedule in the KB8.5 tumor xenograft model. KB8.5 tumors were established in female athymic nu/nu mice (Charles River Laboratories) by subcutaneous injection of 5×10$^6$ cells in 0.2 mL of 1:1 ratio of HBSS and Matrigel™ into the right flank of each mouse. When tumors reached an average of 285 mm$^3$, mice were randomized based on tumor volumes into treatment groups (n=10). Animals were i.v. administered Compound IIa or SB-715992. Paclitaxel was administered at 30 mg/kg i.p. All were dosed on a q4d×3 schedule. (Left) Efficacy/tumor volumes of treatment groups vs. days post dosing initiation; (Right) Percent body weight change relative to initial weights on day of randomization/dosing initiation. No groups were statistically different from the vehicle group (ANOVA on Ranks).

EMBODIMENTS OF THE INVENTION

A. Definitions and Overview

Figure 1:
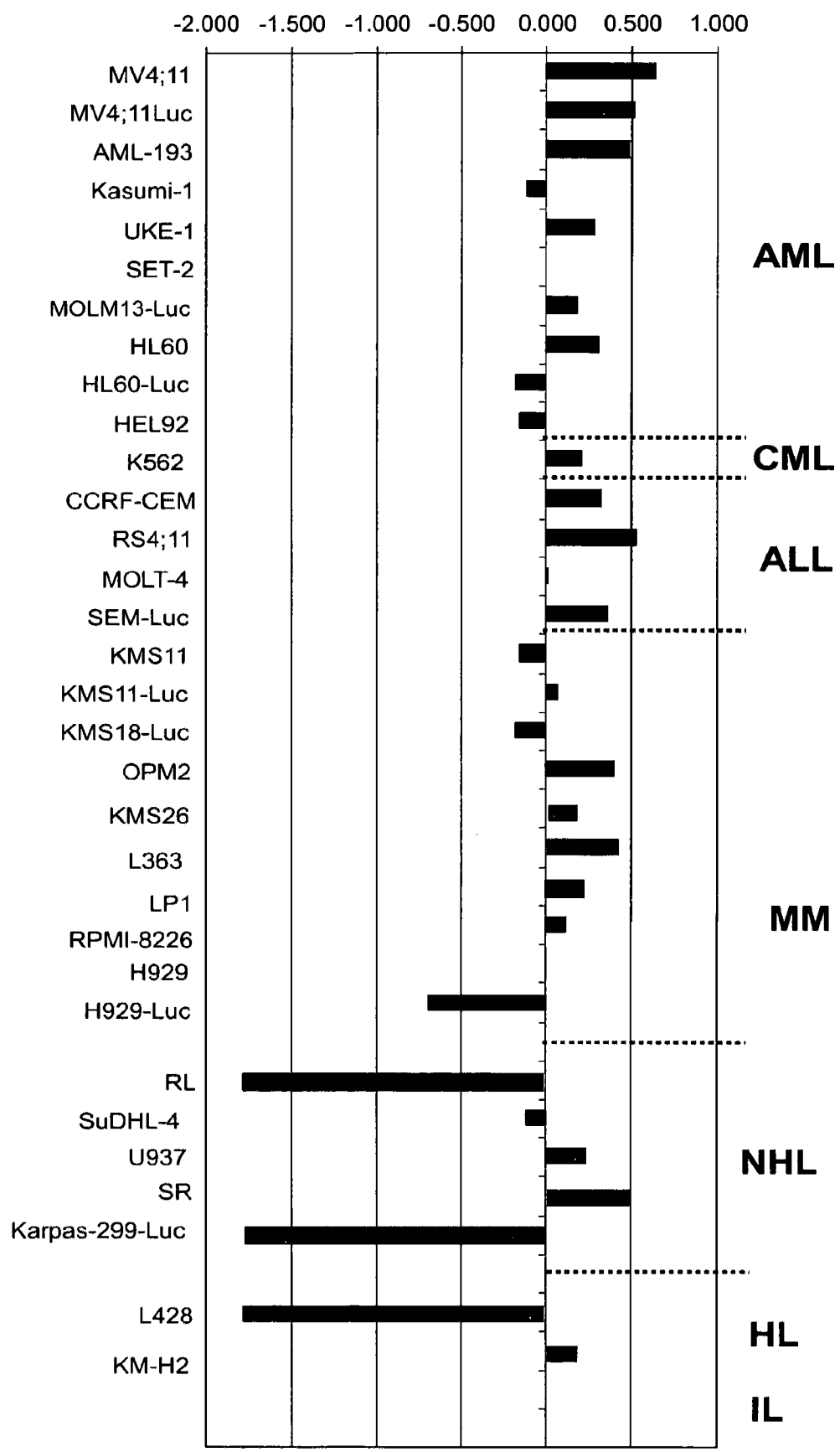
FIG. 1. Relative sensitivity to compound IIa for cell lines derived from hematological malignancies. Relative sensitivities based on the CellTiter Glo® assay of cell lines in a hematological malignancy panel are shown by plotting the difference between the average of the Log(GI50) (GI50 is the concentration at 50% inhibition) values for the entire panel and the Log(GI50) value for each cell line; positive values (bars to the right) indicate cell lines that are more sensitive than average and negative values (bars to the left) indicate cell lines that are less sensitive than average.

It is to be understood that the terminology used herein is for the purpose of describing particular embodiments only and is not intended to limit the scope of the present invention. It must be noted that as used herein and in the claims, the singular forms "a," "and" and "the" include plural referents unless the context clearly dictates otherwise. In this specification and in the claims which follow, reference will be made to a number of terms which shall be defined to have the following meanings:

As used herein, "alkyl" refers to monovalent saturated aliphatic straight chain, branched, or cyclic hydrocarbyl groups having from 1 to 10 carbon atoms and more preferably 1 to 4 carbon atoms. This term is exemplified by groups such as methyl, ethyl, n-propyl, iso-propyl, iso-butyl, n-butyl, t-butyl, n-pentyl, and the like.

The term "linear alkyl" refers to an alkyl group that is not branched.

"Substituted alkyl" refers to an alkyl group having one or more substituents, frequently from 1 to 4, and preferably 1 to 2, substituents. Suitable substituents for alkyl groups are selected from the group consisting of substituted or unsubstituted alkoxy, substituted or unsubstituted acyl, substituted or unsubstituted acylamino, substituted or unsubstituted acyloxy, substituted or unsubstituted amino, substituted or unsubstituted aminoacyl, aryl, substituted aryl, aryloxy, substituted aryloxy, cyano, halogen, hydroxyl, nitro, carboxyl, oxo, hydroxy-imino, substituted or unsubstituted alkoxy-imino carboxyl C1-C4 esters, cycloalkyl, substituted cycloalkyl, substituted or unsubstituted spirocycloalkyl, heteroaryl, substituted heteroaryl, heterocyclic, substituted heterocyclic, —SO$_2$-alkyl, —SO$_2$-substituted alkyl wherein said substituents are defined herein. Preferred substituents for alkyl groups include alkoxy, hydroxy, halo which is preferably F or Cl, cyano, oxo, substituted or unsubstituted amino, substituted or unsubstituted acyloxy and substituted or unsubstituted acylamino.

The term "haloalkyl" refers to an alkyl group wherein at least one hydrogen atom is replaced with a halogen atom. In one embodiment, the term refers to fluoromethyl, difluoromethyl or trifluoromethyl, and the like.

The term "hydroxyalkyl" refers to an alkyl group wherein at least one hydrogen atom is replaced with a hydroxy group. In one embodiment, the term refers to hydroxymethyl, 1- or 2-hydroxyethyl, 1-, 2-, or 3-hydroxypropyl, and the like.

"Alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like. 'Substituted alkylene" refers to an alkylene group having one or more substituents, preferably 1-4 and more preferably 1-2 substituents selected from the substituents suitable for alkyl groups.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)— cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the group —C(O)NRR where each R is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic, and where two R groups can be joined to form, together with the nitrogen atom they are attached to, a heterocyclic or substituted heterocyclic ring; wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Where two R groups join to form a ring, frequently it is a 5-6 membered ring that is optionally substituted as permitted according to the substituents that can be on the R groups; often it is selected from pyrrolidine, piperidine, morpholine, thiomorpholine, and piperazine.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Oxyacyl" or "carboxyl ester" refers to the groups —C(O)O-alkyl, substituted —C(O)O-alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Alkenyl" refers to alkenyl groups having from 2 to 6 carbon atoms and preferably 2 to 4 carbon atoms and having at least 1 and preferably from 1 to 2 sites of alkenyl unsaturation. Such groups are exemplified by vinyl, allyl, but-3-en-1-yl, and the like.

"Substituted alkenyl" refers to alkenyl groups having one or more, preferably from 1 to 4 substituents, and more preferably 1 to 2 substituents. Suitable substituents include those described for alkyl groups herein.

"Alkynyl" refers to alkynyl groups having from 2 to 6 carbon atoms and preferably 2 to 3 carbon atoms and having at least 1 and preferably from 1 to 2 sites of alkynyl unsaturation.

"Substituted alkynyl" refers to alkynyl groups having one or more, preferably from 1 to 4 substituents, and more preferably 1 to 2 substituents. Suitable substituents include those described as substituents for alkyl groups herein. "Cyano" refers to the group —CN.

"Amino" refers to the group —NH$_2$.

"Substituted amino" refers to the group —NR'R" where R' and R" are independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, —SO$_2$-alkyl, —SO$_2$-substituted alkyl, and where R' and R" are optionally joined, together with the nitrogen bound thereto, to form a heterocyclic or substituted heterocyclic group; provided that R' and R" are not both hydrogen. When R' is hydrogen and R" is alkyl, the substituted amino group is sometimes referred to herein as alkylamino. When R' and R" are alkyl, the substituted amino group is sometimes referred to herein as dialkylamino. When referring to a monosubstituted amino, it is meant that either R' or R" is hydrogen but not both. When referring to a disubstituted amino, it is meant that neither R' nor R" is hydrogen.

"Acylamino" refers to the groups —NRC(O)alkyl, —NRC(O)substituted alkyl, —NRC(O)cycloalkyl, —NRC(O)substituted cycloalkyl, —NRC(O)alkenyl, —NRC(O)substituted alkenyl, —NRC(O)alkynyl, —NRC(O)substituted alkynyl, —NRC(O)aryl, —NRC(O)substituted aryl, —NRC(O)heteroaryl, —NRC(O)substituted heteroaryl, —NRC(O)heterocyclic, and —NRC(O)substituted heterocyclic where R is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Nitro" refers to the group —NO$_2$.

"Cyano" refers to the group —CN.

"Aryl" or "Ar" refers to a monovalent aromatic carbocyclic group of from 6 to 14 carbon atoms having a single ring (e.g., phenyl) or multiple condensed rings (e.g., naphthyl or anthryl), wherein condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryls include phenyl and naphthyl.

"Substituted aryl" refers to aryl groups which are substituted with one or more, preferably from 1 to 3 substituents, and more preferably 1 to 2 substituents. Suitable substituents include hydroxy, acyl, acylamino, acyloxy, alkyl, substituted alkyl, alkoxy, substituted alkoxy, alkenyl, substituted alkenyl, alkynyl, substituted alkynyl, amino, substituted amino, aminoacyl, aryl, substituted aryl, aryloxy, substituted aryloxy, carboxyl, carboxyl esters, cyano, thiol, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, substituted heterocyclyloxy, amino sulfonyl (NH$_2$—SO$_2$—), and substituted amino sulfonyl.

"Aryloxy" refers to the group aryl-O— that includes, by way of example, phenoxy, naphthoxy, and the like.

"Substituted aryloxy" refers to substituted aryl-O— groups.

"Benzyl" refers to the group —CH$_2$-phenyl.

"Arylmethyl" refers to the group —CH$_2$-aryl.

"Carboxyl" refers to —COOH or salts thereof.

"Carboxyl ester" refers to a group having the formula —COOR, where R is substituted or unsubstituted alkyl, alkenyl, alkynyl, aryl, heteroaryl, arylalkyl, or heteroarylalkyl. Frequently, R is an optionally substituted C1-C4 alkyl group, such as methyl, ethyl, isopropyl, or methoxyethyl.

"Cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

"Spirocycloalkyl" refers to cyclic groups from 3 to 10 carbon atoms having a cycloalkyl ring with a spiro union (the union formed by a single atom which is the only common member of the rings) as exemplified by the following structure, wherein the two open valences are connected together to form a ring:

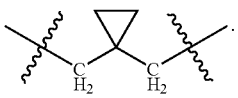

"Substituted cycloalkyl" refers to a cycloalkyl group, having from 1 to 5 substituents selected from the group consisting of alkyl, substituted alkyl, oxo (=O), thioxo (=S), alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Halo" or "halogen" refers to fluoro, chloro, bromo or iodo, and preferably is fluoro or chloro.

"Hydroxy" refers to the group —OH.

"Oxo" refers to the group =O.

"Heteroaryl" refers to an aromatic group having from 5 to 10 ring atoms including 1 to 4 heteroatoms selected from the group consisting of oxygen, nitrogen and sulfur as ring members. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O) sulfinyl, or sulfonyl moieties. Preferred heteroaryls include pyridinyl, pyrrolyl, indolyl, thiophenyl, ozaxolyl, isoxazolyl, thiazolyl, isothiazolyl, imidazolyl, triazolyl, and furanyl.

"Substituted heteroaryl" refers to heteroaryl groups that are substituted with from 1 to 3 substituents, preferably 1 or 2 substituents, selected from the same group of substituents defined for substituted aryl.

"Nitrogen-containing heteroaryl" and "nitrogen-containing substituted heteroaryl" refers to heteroaryl groups and substituted heteroaryl groups comprising at least one nitrogen ring atom and optionally comprising other heteroatoms such as sulfur, nitrogen, or oxygen and the like as ring members.

"Heteroaryloxy" refers to the group —O-heteroaryl and "substituted heteroaryloxy" refers to the group —O-substituted heteroaryl wherein heteroaryl and substituted heteroaryl are as defined herein.

"Heterocycle" or "heterocyclic" or "heterocycloalkyl" or "heterocyclyl" refers to a saturated or unsaturated group having a single ring or multiple condensed rings, including fused bridged and spiro ring systems, from 3 to 10 ring atoms including from 1 to 4 hetero atoms selected from the group consisting of nitrogen, sulfur and oxygen as ring members; in fused ring systems, one or more of the rings can be cycloalkyl, aryl or heteroaryl provided that the point of attachment is through the heterocyclic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with one or more and preferably from 1 to 3 substituents, selected from the substituents described herein. Suitable substituents include those described herein for alkyl and cycloalkyl groups.

Examples of heterocyclyls and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

"Nitrogen-containing heterocyclic" and "nitrogen-containing substituted heterocyclic" refers to heterocyclic groups and substituted heterocyclic groups comprising at least one nitrogen ring atom and optionally comprising other heteroatoms as ring atoms selected from, sulfur, oxygen and the like.

"Thiol" refers to the group —SH.

"Alkylthio" or "thioalkoxy" refers to the group —S-alkyl.

"Substituted alkylthio" or "substituted thioalkoxy" refers to the group —S-substituted alkyl.

"Arylthio" refers to the group —S-aryl, where aryl is defined above.

"Substituted arylthio" refers to the group —S-substituted aryl, where substituted aryl is defined above.

"Heteroarylthio" refers to the group —S-heteroaryl, where heteroaryl is as defined above.

"Substituted heteroarylthio" refers to the group —S-substituted heteroaryl, where substituted heteroaryl is defined above.

"Heterocyclicthio" refers to the group —S-heterocyclic and "substituted heterocyclicthio" refers to the group —S-substituted heterocyclic, where heterocyclic and substituted heterocyclic are as defined above.

"Heterocyclyloxy" refers to the group heterocyclyl-O— and "substituted heterocyclyloxy refers to the group substituted heterocyclyl-O— where heterocyclyl and substituted heterocyclyl are as defined above.

"Cycloalkylthio" refers to the group —S-cycloalkyl and "substituted cycloalkylthio" refers to the group —S-substituted cycloalkyl, where cycloalkyl and substituted cycloalkyl are as defined above.

"Biological activity" as used herein refers to an inhibition concentration when tested in at least one of the assays outlined in Examples 1-13.

As used herein, the term "pharmaceutically acceptable salts" refers to the nontoxic acid or alkaline earth metal salts of the compounds of formula (I) and (II). These salts can be prepared in situ during the final isolation and purification of the compounds of formula (I) and (II), or by separately reacting the base or acid functions with a suitable organic or inorganic acid or base, respectively. Representative pharmaceutically acceptable salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfonate, ethanesulfonate, glucoheptanoate, glycerophosphate, hemi-sulfate, heptanoate, hexanoate, fumarate, hippurate, hydrochloride, hydrobromide, hydroiodide, 2-hydroxyethanesulfonate, lactate, maleate, methanesulfonate, nicotinate, 2-napthalenesulfonate, oxalate, pamoate, pectinate, persulfate, 3-phenylpropionate, picrate, pivaloate, propionate, succinate, sulfate, tartrate, thiocyanate, p-toluenesulfonate and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides; arylalkyl halides like benzyl and phenethyl bromides, and others. Water or oil-soluble or dispersible products are thereby obtained.

Examples of acids that may be employed to form pharmaceutically acceptable acid addition salts include such inorganic acids as hydrochloric acid, sulfuric acid and phosphoric acid and such organic acids as acetic, hippuric, lactic, oxalic acid, maleic acid, methanesulfonic acid, succinic acid and citric acid. Basic addition salts can be prepared in situ during the final isolation and purification of the compounds of formula (I) and (II), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters which hydrolyze in vivo and include those that break down in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates.

The term "pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A discussion is provided in T. Higuchi and V. Stella, PRO-DRUGS AS NOVEL DELIVERY SYSTEMS, Vol. 14 of the A.C.S. Symposium Series, and in Edward B. Roche, ed., BIOREVERSIBLE CARRIERS IN DRUG DESIGN, American Pharmaceutical Association and Pergamon Press, 1987, both of which are incorporated herein by reference.

As used herein "anticancer agents" or "agent for the treatment of cancer" or "cancer therapeutics" refers to agents that include, by way of example only, agents that induce apoptosis; polynucleotides (e.g., ribozymes); polypeptides (e.g., enzymes); drugs; biological mimetics; alkaloids; alkylating agents; antitumor antibiotics; antimetabolites; hormones; platinum compounds; monoclonal antibodies; monoclonal antibodies conjugated with anticancer drugs, toxins, and/or radionuclides; biological response modifiers (e.g. interferons and interleukins, etc.); adoptive immunotherapy agents; hematopoietic growth factors; agents that induce tumor cell differentiation (e.g. all-trans-retinoic acid, etc.); gene therapy reagents; antisense therapy reagents and nucleotides; tumor vaccines; inhibitors of angiogenesis, and the like. Numerous other agents are well within the purview of one of skill in the art It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, 'substituted aryl' groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group on an ethenylic or acetylenic unsaturation, or a divalent group such as oxo on a phenyl ring). Such impermissible substitution patterns are well known to the skilled artisan.

Compounds of this invention may exhibit stereoisomerism by virtue of the presence of one or more asymmetric or chiral centers in the compounds. The present invention contemplates each of the various stereoisomers and mixtures thereof. Certain of the compounds of the invention comprise asymmetrically substituted carbon atoms. Such asymmetrically substituted carbon atoms can result in the compounds of the invention comprising mixtures of stereoisomers at a particular asymmetrically substituted carbon atom or a single stereoisomer. As a result, racemic mixtures, mixtures of diastereomers, single enantiomer, as well as single diastereomers of the compounds of the invention are included in the present invention. The terms "S" and "R" configuration, as used herein, are as defined by the IUPAC 1974 "RECOMMENDATIONS FOR SECTION E, FUNDAMENTAL STEREOCHEMISTRY," *Pure Appl. Chem.* 45:13-30, 1976. Desired enantiomers can be obtained by chiral synthesis from commercially available chiral starting materials by methods well known in the art, or may be obtained from mixtures of the enantiomers by separating the desired enantiomer by using known techniques. For some embodiments of the compounds of formula (II), a single isomer is depicted for at least one stereocenter in the compounds; where a single isomer of a particular stereocenter is depicted, the depicted absolute relative stereochemistry is a preferred embodiment. Where no specific stereochemistry is indicated, a stereocenter may be in the R or S configuration, or it may be any mixture of the two, including a racemic mixture.

Compounds of this invention may also exhibit geometrical isomerism. Geometrical isomers include the cis and trans forms of compounds of the invention having double bonds such as alkenyl, oxime, imine, or alkenylenyl moieties. The present invention comprises the individual geometrical isomers and stereoisomers and mixtures thereof.

Compounds of the invention can be prepared by methods known in the art and further described herein. For example, methods for making compounds of formula (I) and formula (II) are described in published application PCT/US2005/022062 (WO 06/002236) and the corresponding U.S. patent applications. Examples of additional synthesis methods applicable to the preparation of compounds of formula (II) are provided herein.

An example of the preparation of certain KSP inhibitors of Formula I and/or Formula II is shown below in Scheme 1.

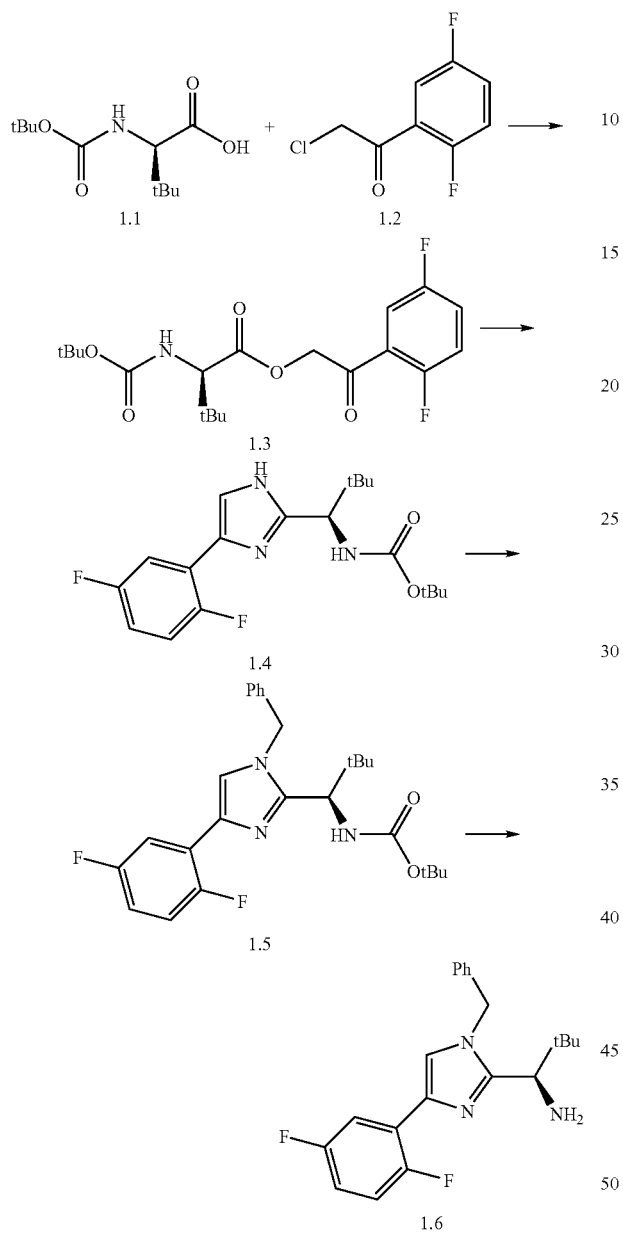

Compound 1.1 and 1.2 were reacted with $K_2CO_3$ in acetone containing KI. The use of $K_2CO_3$/acetone was found to be superior to $Cs_2CO_3$/ethanol because of the lower cost of $K_2CO_3$ and because compound 1.3 precipitated from the acetone solution upon addition of water, removing the need for an aqueous workup to extract 1.3. Keto ester 1.3 was then refluxed with ammonium acetate ($NH_4OAc$) in toluene to give imidazole 1.4. The use of toluene was found to afford higher yields of the imidazole in comparison to refluxing in xylenes with a Dean Stark trap, as the latter method led to the removal of ammonium acetate from the reaction mixture into the trap. Reaction of 1.4 with benzylbromide and $K_2CO_3$ in dimethylformamide afforded 1.5, which can be precipitated from the reaction solution upon addition of water. Treatment of 1.5 with methanol and acetyl chloride gave the HCl salt of 1.6 which was then converted to its free base when titrated with a NaOH/methanol solution. The formation of 1.6 from 1.1 and 1.2 was found to proceed with 81% yield with high purity (>97% as determined by HPLC) and high optical purity (>99% e.e.).

Compound 1.6 can be reacted with an aldehyde $HC(O)R^{b'}$ under reductive amination conditions or with $Y-R^b$, where Y is a leaving group, to introduce an alkyl group on the amine nitrogen, which can then be acylated to provide compounds of formula (I) or (II). Scheme 2 illustrates the preparation of an aldehyde that can be used in the reductive amination step to prepare compounds of formula I and/or formula (II), and particularly compounds of formula IIa or IIb or IIc.

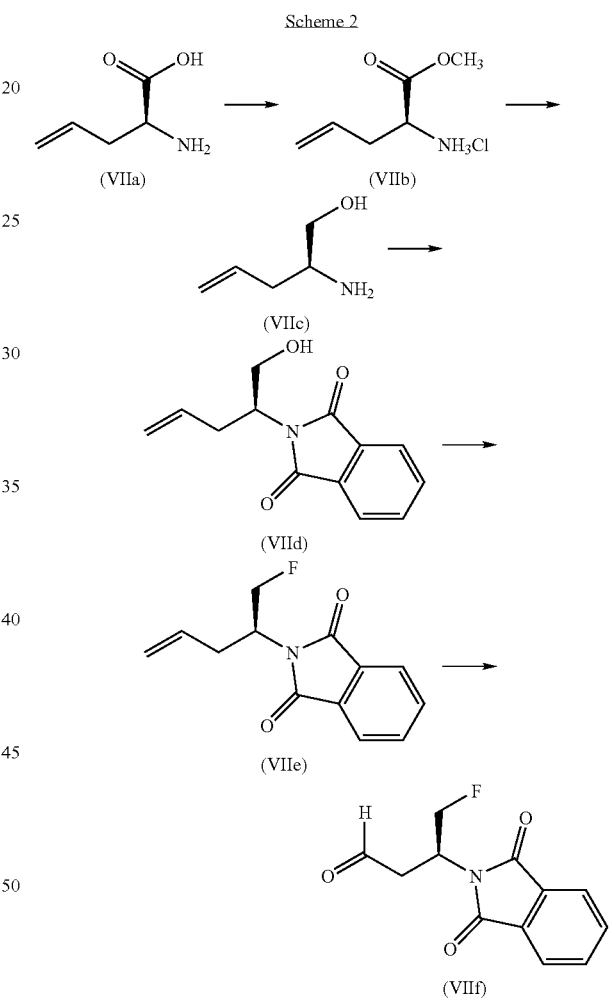

After the reductive amination, known acylating agents and conditions are used to acylate the secondary amine to provide compounds of formula (I) or (II). Scheme 3 illustrates the reductive amination to provide VIIIa. Acylation of the amine followed by deprotection of the phthalimide and removal of a protecting group on the free hydroxyl group provides compound IIa. Suitable protective groups for the hydroxyl include, for example, benzyl ethers that can be removed by hydrogenolysis and alkyl carbonates that can be selectively removed with reagents such as trimethylsilyl iodide. The measured mass of compound IIa, determined by high-resolution mass spectrometry, was 503.2609 for the [M+H]+ ion, which is consistent with the molecular formula $C_{27}H_{33}N_4O_2F_3$.

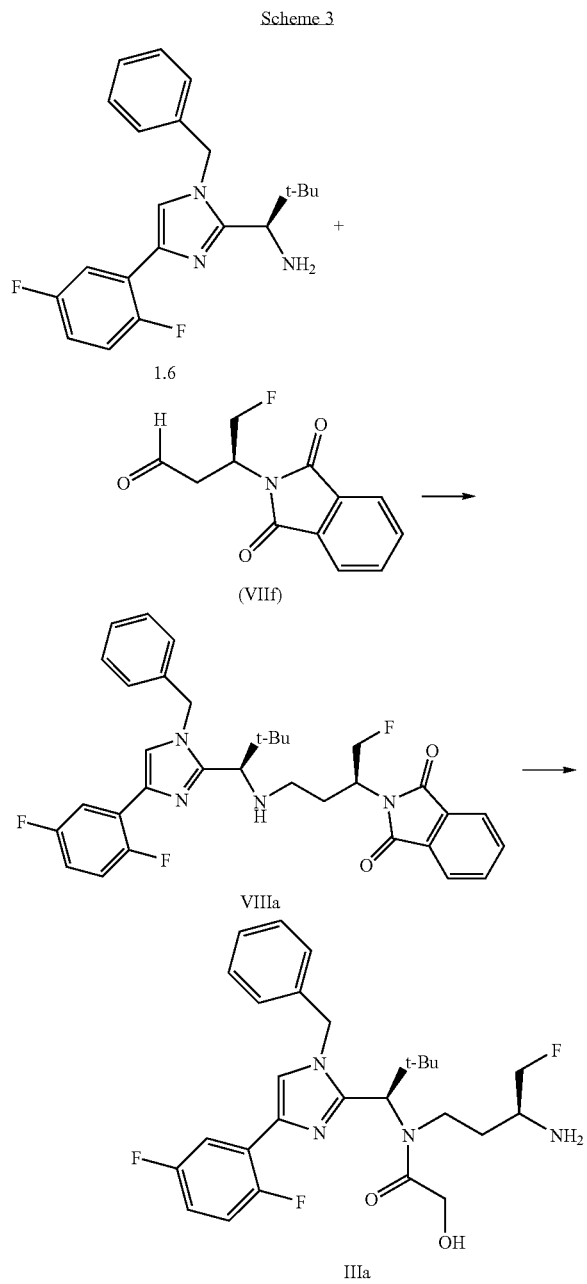

Scheme 3

This compound is further characterized by its IR spectrum, having absorption bands at 3500-2700 (br), 1641, 1591, 1508, 1491, 1162, and 1088 cm$^{-1}$. It is further characterized by the following nmr data:

| # | δ $^1$H [ppm] | n $^1$H | Mult* | # | δ $^{13}$C [ppm] |
|---|---|---|---|---|---|
| 1 | 7.84 | 1 | d | 1 | 172.9 |
| 2 | 7.74 | 1 | m | 2** | 158.4 |

-continued

| # | δ $^1$H [ppm] | n $^1$H | Mult* | # | δ $^{13}$C [ppm] |
|---|---|---|---|---|---|
| 3 | 7.38 | 2 | t | 3** | 154.8 |
| 4 | 7.34-7.27 | 4 | m | 4 | 144.4 |
| 5 | 7.09 | 1 | m | 5 | 136.7 |
| 6 | 5.71 | 1 | s | 6 | 131.6 |
| 7 | 5.16 | 2 | AB | 7 | 128.5 |
| 8 | 4.65 | 1 | s, broad | 8 | 127.8 |
| 9 | 4.21 | 2 | AB | 9 | 127.4 |
| 10 | 3.72 | 2 | d, t | 10** | 123.5 |
| 11 | 3.55 | 1 | t | 11** | 121.0 |
| 12 | 2.41 | 1 | m | 12** | 117.2 |
| 13 | 1.43 | 2 | s, broad | 13** | 113.6 |
| 14 | 0.96 | 1 | m | 14** | 112.4 |
| 15 | 0.91 | 3 | s | 15** | 87.2 |
| 16 | −0.77 | 1 | m | 16 | 59.9 |
|  |  |  |  | 17 | 53.1 |
|  |  |  |  | 18** | 49.1 |
|  |  |  |  | 19 | 48.5 |
|  |  |  |  | 20 | 41.7 |
|  |  |  |  | 21 | 37.1 |
|  |  |  |  | 22 | 32.2 |
|  |  |  |  | 23 | 27.3 |

*Multiplicity: AB(AB quartet), b(broad), d(doublet), dd(doublet of doublets), m(multiplet), s(singlet), t(triplet).
**Midpoint shift of $^{19}$F-coupled multiplet.

Note that the absolute stereochemistry of the chiral centers in this molecule is identified based on the chirality of known starting materials or intermediates. HPLC and nmr data support the conclusion that the above process provides the compound as a single isomer.

Using the same methods, compound IIc was prepared by use of a known chiral alpha-hydroxy acylating agent. It exhibited the expected mass spectrum for the assigned structure, including a molecular ion M+H at m/z=517.3, and analytical HPLC Rt=3.70 min (reverse phase). LC/ESI-MS data were recorded using a Waters LCT Premier mass spectrometer with dual electrospray ionization source and Agilent 1100 liquid chromatograph. The resolution of the MS system was approximately 12000 (FWHM definition). HPLC separation was performed at 1.0 mL/min flow rate with the gradient from 10% to 95% in 2.5 min. 10 mM Ammonium Formate was used as the modifier additive in the aqueous phase. Sulfadimethoxine (Sigma; protonated molecule m/z 311.0814) was used as a reference and acquired through the Lock-Spray™ channel every third scan. The mass accuracy of the system has been found to be <5 ppm.

Suitable acylating agents and acids for the acylation step include acyl halides, anhydrides, and acids having the appropriate R$^c$ group (see formula I). Suitable amide coupling conditions include use of a variety of amide coupling reagents to form the amide bond, such as the carbodiimides N—N'-dicyclohexylcarbodiimide (DCC), N—N'-diisopropylcarbodiimide (DIPCDI), and 1-ethyl-3-(3'-dimethylaminopropyl)carbodiimide (EDCI). The carbodiimides may be used in conjunction with additives such as dimethylaminopyridine (DMAP) or benzotriazoles such as 7-aza-1-hydroxybenzotriazole (HOAt), 1-hydroxybenzotriazole (HOBt), and 6-chloro-1-hydroxybenzotriazole (C1-HOBt); conditions for such amide bond formations are well known in the art.

Additional amide coupling reagents also include uronium and phosphonium based reagents. Uronium salts include N-[(dimethylamino)-1H-1,2,3-triazolo[4,5-b]pyridine-1-yl-methylene]-N-methyluronium hexafluorophosphate N-oxide (HATU), N-[(1H-benzotriazol-1-yl)(dimethylamino)methylene]-N-methyluronium hexafluorophosphate N-oxide (HBTU), N-[(1H-6-chlorobenzotriazol-1-yl)(dimethylamino)methylene]-N-methyluronium hexafluorophosphate N-oxide (HCTU), N-[(1H-benzotriazol-1-yl)(dimethylamino)methylene]-N-methyluronium tetrafluoroborate N-oxide (TBTU), and N-[(1H-6-chlorobenzotriazol-1-yl)(dimethylamino)methylene]-N-methyluronium tetrafluoroborate N-oxide (TCTU). Phosphonium salts include benzotriazole-1-yl-oxy-tris-(dimethylamino)-phosphonium hexafluorophosphate (BOP), 7-azabenzotriazol-1-yl-N-oxy-tris(pyrrolidino)phosphonium hexafluorophosphate (PyAOP) and benzotriazol-1-yl-N-oxy-tris(pyrrolidino) phosphonium hexafluorophosphate (PyBOP).

The amide formation step may be conducted in a polar solvent such as dimethylformamide (DMF) and may also include an organic base such as diisopropylethylamine (DIEA) or dimethylaminopyridine (DMAP).

Methods for the selection, incorporation and removal of suitable protecting groups for the hydroxyl during preparation of a compound of formula II are well known in the art. Based on the above reaction scheme, compounds of formula II are readily prepared by a person using ordinary skill in the art, who knows how to select suitable starting materials to provide the desired products.

A "KSP inhibitor" is a compound that is capable of inhibiting any measurable activity of a kinesin spindle protein (KSP). Preferably, a KSP inhibitor has an IC50 of less than 100 micromolar, more preferably less than 10 micromolar, and frequently less than 1 micromolar.

A "proliferative disease" includes any disease or condition affecting a vertebrate that is characterized by excessive or undesirable proliferating cells. The "method of treating a proliferative disease", according to this invention, includes a method for treating (inhibiting) the abnormal growth of cells, including transformed cells, in a patient in need of such treatment (e.g., a mammal such as a human), by administering, concurrently or sequentially, an effective amount of a KSP inhibitor alone or in combination with an effective amount of a chemotherapeutic agent and/or radiation. Abnormal growth of cells means cell growth independent of normal regulatory mechanisms (e.g., loss of contact inhibition), including the abnormal growth of tumor cells or benign and malignant cells of other proliferative diseases.

The terms "cancer" and "cancerous" refer to or describe the physiological condition in mammals that is typically characterized by unregulated cell growth.

"Tumor," as used herein, refers to all neoplastic cell growth and proliferation, whether malignant or benign, and all pre-cancerous and cancerous cells and tissues. The term "solid tumor" refers to a cancer or carcinoma of body tissues other than blood, bone marrow, and lymphoid system. Examples of solid tumors may be, but are not limited to, lung carcinoma, breast carcinoma, ovarian carcinoma, skin carcinoma, colon carcinoma, urinary bladder carcinoma, liver carcinoma, gastric carcinoma, prostate cancer, pancreatic cancer, renal cell carcinoma, nasopharyngeal carcinoma, squamous cell carcinoma, thyroid papillary carcinoma, cervical carcinoma, small cell lung carcinoma, non-small cell lung carcinoma, head and neck squamous cell cancer and sarcomas.

As used herein, the term "hematological cancer" refers to a cancer of the blood, and includes leukemia and malignant lymphoproliferative disorders, among others. "Leukemia" refers to a cancer of the blood, in which too many white or red blood cells are made, thus crowding out the other parts that make up the blood, such as platelets and normal red blood cells. It is understood that cases of leukemia are classified as acute or chronic. Cancer cells in acute leukemias are blocked at an immature stage, yet they continue to multiply. Consequently, there is a large accumulation of non-functional immature cells and the concomitant loss of functional cells. Chronic leukemias progress more slowly, with cancer cells developing to full maturity. Furthermore, the white blood cells may be myelogenous or lymphoid. Thus, certain forms of leukemia may be, by way of example, acute lymphotic (or lymphoblastic) leukemia (ALL); acute myelogenic leukemia (AML); chronic lymphocytic leukemia (CLL); or chronic myelogenic leukemia (CML); and myelodysplastic syndrome. "Malignant lymphoproliferative disorders" may refer to a lymphoma, such as Hodgkin's lymphoma, and non-Hodgkin's lymphoma, or multiple myeloma among others.

Some tumors described herein can be resistant to various therapeutic agents. 'Resistant' means that the cancer is not substantially affected by a therapeutic agent at its normal administration rates, or at rates that are tolerated by the patient. A major form of resistance against a variety of the antineoplastic agents involves the function of a group of membrane protein pumps that extrude these cytotoxic molecules. "Multi-drug resistant pumps" may refer to the super-family of ATP Binding Cassette (ABC) proteins, present in organisms from bacteria to humans. ABC transporter pumps are located in the plasma membrane of the cells or in the membrane of different cellular organelles, and mediate the translocation of various molecules across these barriers. Most ABC pumps utilize the energy of ATP hydrolysis for this transport activity (active transporters), but some ABC pumps form specific membrane channels.

Numerous clinical studies have revealed that the multi-drug resistance phenotype in tumors is associated with the overexpression of certain ABC pumps, termed multiple-drug resistant (MDR) proteins. The P-glycoprotein (termed P-gp, MDR1 or ABCB1)-mediated multi-drug resistance was the first discovered (Juliano, R. L. and Ung, v., Biochem. Biophys. Acta, 455, 152-162 (1976); Chen, D. et al., Cell, 47, 381-389 (1986); Ueda, K. et al., Proc. Natl. Acad. Sci., 84, 3004-3008 (1987)) and probably still is the most widely observed mechanism in clinical multi-drug resistance (Endicott, J A and Ling, v., Annu. Rev. Biochem., 58, 137-171 (1989); Higgins, C. E, Ann. Rev. Cell Biol., 8, 67-113 (1992); Gottesman, M M. and Pasta, I., Annu. Rev. Biochem., 62, 385-427 (1993); Gottesman, M. M et al., Nat. Rev. Cancer; 2, 48-58 (2002)). There are two other ABC pumps, which have been demonstrated to participate in the multi-drug resistance of tumors: the multi-drug resistance protein 1 (MRP1, ABCC1), and the mitoxantrone resistance protein (MXR/BCRP, ABCG2) ((Gottesman, M. M ibid, Cole, S. P. c. et al., Science, 258, 1650-1654 (1992); Borst, P. et al., J. Natl. Cancer. Inst., 92, 1295-1302 (2000); Deeley, R. G. and Cole, S. P. c., Sem. Cancer Bio I., 8, 193-204 (1997); Litman, l et al., Cell. Mol. Life. Sci., 58, 931-959 (2001)). Furthermore, other human ABC pumps capable of actively transporting various compounds out of cells may also be players in selected cases of multi-drug resistance. These include ABCB4 (MDR3) and ABCB11 (sister P-gp or BSEP), two pumps residing predominantly in the liver with a function involved in the secretion of phosphatidyl choline and bile acids, respectively (Lecureur, V. et al., Toxicol., 152, 203-219 (2000); Paulusma, c. c. et al., Science, 271, 1126-1128 (1996); Paulusma, c. c. et al., Hepatology, 25, 1539-1542 (1997)). MDR3 has been already shown to transport certain drugs as well (Smith, A J. et al., J Biol. Chem., 275, 23530-23539 (2000)). In addition to MRP1, five homologues (MRP2-MRP6) have been cloned. Overexpression of MRP2 (an organic anion transporter which can also extrude hydrophobic compounds) was definitively shown to confer cancer MDR9 (Kool, M et al., Cancer Res., 57, 3537-3547 (1997)). MRP3, an organic conjugate transporter pump, and MRP5, a nucleoside transporter pump, are also candidate proteins for causing certain forms of drug resistance (Borst, P. et al. *ibid*).

"Antibodies" and "immunoglobulins" (Igs) are glycoproteins having the same structural characteristics. While antibodies exhibit binding specificity to an antigen, immunoglobulins include both antibodies and other antibody-like molecules that lack antigen specificity. Polypeptides of the latter kind are, for example, produced at low levels by the lymph system and at increased levels by myelomas.

The word "label" when used herein refers to a detectable compound or composition that is conjugated directly or indirectly to the antibody so as to generate a "labeled" antibody. The label may be detectable by itself (e.g., radioisotope labels or fluorescent labels) or, in the case of an enzymatic label, may catalyze chemical alteration of a substrate compound or composition that is detectable. Radionuclides that can serve as detectable labels include, for example, I-131, I-123, I-125, Y-90, Re-188, Re-186, At-211, Cu-67, Bi-212, and Pd-109. The label might also be a non-radioactive entity such as a toxin that is detectable by its biological or biochemical activities.

The term "antagonist" is used in the broadest sense, and includes any molecule that partially or fully blocks, inhibits, or neutralizes a biological activity of a native target disclosed herein or the transcription or translation thereof.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers comprise buffers such as phosphate, citrate, succinate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and Pluronics. Administration "in combination with" one or more further therapeutic agents includes simultaneous (concurrent) and consecutive administration in any order. Preferably, the therapeutic agents to be combined in such methods are both present at therapeutically relevant levels simultaneously in the body of the treated subject.

A "host cell," as used herein, refers to a microorganism or a eukaryotic cell or cell line cultured as a unicellular entity that can be, or has been, used as a recipient for a recombinant vector or other transfer polynucleotides, and include the progeny of the original cell that has been transfected. It is understood that the progeny of a single cell may not necessarily be completely identical in morphology or in genomic or total DNA complement as the original parent, due to natural, accidental, or deliberate mutation.

"Treatment" is herein defined as the application or administration of a KSP inhibitor to a subject, or application or administration of a KSP inhibitor to an isolated tissue or cell line from a subject, where the subject has a solid tumor or hematological cancer, a symptom associated with a solid tumor or hematological cancer, or a predisposition toward development of a solid tumor or hematological cancer, where the purpose is to cure, heal, alleviate, relieve, alter, remedy, ameliorate, improve, or affect the solid tumor or hematological cancer, any associated symptoms of the solid tumor or hematological cancer, or the predisposition toward development of the solid tumor or hematological cancer. The subject may be a mammal, and in some embodiments the subject is a human. Frequently, the subject is a human who has been diagnosed with at least one of the conditions described herein as suitable for treatment with the compounds and methods of the invention. In specific embodiments, the subject can be one having a cancer that expresses an efflux pump that promotes drug resistance, such as P-gp, or the subject can be one having a tumor that has demonstrated resistance to drugs like paclitaxel or SB-715992.

By "treatment" is also intended the application or administration of a pharmaceutical composition comprising the KSP inhibitor to a subject, or application or administration of a pharmaceutical composition comprising the KSP inhibitor to an isolated tissue or cell line from a subject, who has a solid tumor or hematological cancer, a symptom associated with a solid tumor or hematological cancer, or a predisposition toward development of the solid tumor or hematological cancer, where the purpose is to cure, heal, alleviate, relieve, alter, remedy, ameliorate, improve, or affect the solid tumor or hematological cancer, any associated symptoms of the solid tumor or hematological cancer, or the predisposition toward development of the solid tumor or hematological cancer.

By "anti-tumor activity" is intended a reduction in the rate of malignant cell proliferation or accumulation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Therapy with at least one KSP inhibitor causes a physiological response that is beneficial with respect to treatment of solid tumors in a human. Therapy with at least one KSP inhibitor causes a physiological response that is beneficial with respect to treatment of hematological tumors in a human. It is recognized that the methods of the invention may be useful in preventing further tumor outgrowths arising during therapy.

In accordance with the methods of the present invention, at least one KSP inhibitor as defined elsewhere herein is used to promote a positive therapeutic response with respect to a solid tumor or hematological cancer. By "positive therapeutic response" with respect to cancer treatment is intended an improvement in the disease in association with the anti-cancer activity of these antibodies or fragments thereof, and/or an improvement in the symptoms associated with the disease. That is, an anti-proliferative effect, the prevention of further tumor outgrowths, a reduction in tumor size, a reduction in the number of cancer cells, and/or a decrease in one or more symptoms mediated by stimulation of cancer cells can be observed. Thus, for example, an improvement in the disease may be characterized as a complete response. By "complete response" is intended an absence of clinically detectable disease with normalization of any previously abnormal radiographic studies, bone marrow, and cerebrospinal fluid (CSF). Such a response must persist for at least one month following treatment according to the methods of the invention. Alternatively, an improvement in the disease may be categorized as being a partial response. By "partial response" is intended at least about a 50% decrease in all measurable tumor burden (i.e., the number of tumor cells present in the subject) in the absence of new lesions and persisting for at least one month. Such a response is applicable to measurable tumors only.

Tumor response can be assessed for changes in tumor morphology (i.e., overall tumor burden, tumor size, and the like) using screening techniques such as magnetic resonance imaging (MRI) scan, x-radiographic imaging, computed tomographic (CT) scan, bioluminescent imaging, for example, luciferase imaging, bone scan imaging, and tumor biopsy sampling including bone marrow aspiration (BMA). In addition to these positive therapeutic responses, the subject undergoing therapy with the KSP inhibitor may experience the beneficial effect of an improvement in the symptoms associated with the disease.

By "therapeutically effective dose or amount" or "effective amount" is intended an amount of KSP inhibitor that, when administered brings about a positive therapeutic response with respect to treatment of a patient with a solid tumor or hematological cancer. It is recognized that the method of treatment may comprise a single administration of a therapeutically effective dose or multiple administrations of a therapeutically effective dose of the inhibitor.

The Bcr-Abl tyrosine kinase gene encodes a fusion protein, and is created by the abnormal junction of the BCR and ABL genes. This fusion is found on the so-called Philadelphia chromosome caused by the reciprocal translocation t(9:22) that results in the formation of the Bcr-Abl fusion gene which causes unregulated expression of the ABL tyrosine kinase. The presence of a Philadelphia chromosome is considered one of the causative factors in both CML and ALL (Abraham, (2007) *Community Oncology* 4 (1) p. 11-14). Currently, the Bcr-Abl tyrosine kinase is the target for a new class of Bcr-Abl inhibitory therapeutic compounds, such as imatinib (Gleevec®, Novartis), dasatinib (Sprycel®, Bristol-Myers Squibb) and nilotinib (AML107, Novartis). The Bcr-Abl tyrosine kinase acts upstream of the KSP protein.

In some preferred embodiments, the KSP inhibitor is administered in combination with at least one other "active compound" which may be a cancer therapy, including, but not limited to, surgery, radiation therapy, chemotherapy, cytokine therapy, or other monoclonal antibody intended for use in treatment of the solid tumor of interest, where the additional cancer therapy is administered prior to, during, or subsequent to the KSP inhibitor therapy, and both therapeutic agents are present at therapeutic levels concurrently in the subject. Thus, where the combined therapies comprise administration of KSP inhibitor in combination with administration of another therapeutic agent, as with chemotherapy, cytokine therapy, or other monoclonal antibody, the methods of the invention encompass coadministration, using separate formulations or a single pharmaceutical formulation, and consecutive administration in either order, wherein preferably there is a time period where both (or all) active agents simultaneously exert their therapeutic activities. Where the methods of the present invention comprise combined therapeutic regimens, these therapies can be given simultaneously, i.e., KSP inhibitor is administered concurrently or within the same time frame as the other cancer therapy (i.e., the therapies are going on concurrently, but the KSP inhibitor is not administered precisely at the same time as the other cancer therapy). Alternatively, the KSP inhibitor of the present invention may also be administered prior to or subsequent to the other cancer therapy. Sequential administration of the different cancer therapies may be performed regardless of whether the treated subject responds to the first course of therapy to decrease the possibility of remission or relapse.

In some embodiments of the invention, the KSP inhibitors described herein, are administered in combination with chemotherapy or cytokine therapy, wherein the KSP inhibitor and the chemotherapeutic agent(s) or cytokine(s) may be administered sequentially, in either order, or simultaneously (i.e., concurrently or within the same time frame). Examples of suitable chemotherapeutic agents include, but are not limited to, CPT-11 (Irinotecan), which can be used, for example, in treating colorectal cancer and non-small cell lung cancer; gemcitabine, which can be used, for example, in treating lung cancer, breast cancer, and epithelial ovarian cancer; and other chemotherapeutic agents suitable for treatment of solid tumors. Cytokines of interest include, but are not limited to, alpha interferon, gamma interferon, interleukin-2 (IL-2), IL-12, IL-15, and IL-21, granulocyte macrophage colony stimulating factor (GM-CSF), granulocyte colony stimulating factor (G-CSF), or biologically active variants of these cytokines.

In other embodiments of the invention, the KSP inhibitors described herein, are administered in combination with monoclonal antibodies intended for treatment of the solid tumor. Thus, for example, where the subject is undergoing treatment for a gastric or colon cancer, therapy could include administration of effective amounts of a KSP inhibitor described herein, in combination with administration of effective amounts of a monoclonal antibody such as Erbitux® (also known as Cetuximab; ImClone Systems Incorporated, New York, N.Y. and Bristol Meyers Squibb, Princeton, N.J.). Similarly, where the subject is undergoing treatment for colorectal cancer, therapy could include administration of effective amounts of a KSP inhibitor, described herein, in combination with administration of effective amounts of the humanized monoclonal antibody Avastin™ (also known as bevacizumab; Genentech, Inc., San Francisco, Calif.), which binds to and inhibits vascular endothelial growth factor (VEGF), a protein that plays a critical role in tumor angiogenesis. Alternatively, in a subject undergoing treatment for breast cancer, therapy could include administration of effective amounts of a KSP inhibitor described herein, in combination with an effective amount of the humanized monoclonal antibody Herceptin® (also known as trastuzumab; Genentech In, San Francisco, Calif.). Other examples of monoclonal antibodies intended for treatment of solid tumors that can be used in combination with the KSP inhibitors of the present invention include, but are not limited to, an anti-EGFR antibody targeting the epidermal growth factor receptor (for example, IMC-C225 (ImClone Systems, New York, N.Y.) (see, for example, Mendelsohn and Baselga (2000) *Oncogene* 19:6550-6565 and Solbach et al. (2002) *Int. J. Cancer* 101:390-394); anti-IGF-1 receptor antibody, targeting the IGF-1 receptor protein (see, for example, Maloney et al. (2003) *Cancer Res.* 63:5073-5083 and Hailey et al. (2002) *Mol. Cancer. Ther.* 1:1349-1353; anti-MUC1 antibody, targeting the tumor-associated antigen MUC1; anti-α5β1, anti-αvβ5, and anti-αvβ3, targeting these respective integrins, which regulate cell adhesion and signaling processes involved in cell proliferation and survival (see, for example, Laidler et al. (2000) *Acta Biochimica Polonica* 47(4):1159-1170 and Cruet-Hennequart et al. (2003) *Oncogene* 22(11): 1688-1702); anti-P-cadherin antibody, targeting this cadherin family member (see, for example, copending U.S. Patent Application 20030194406); and anti-VE-cadherin antibody, targeting angiogenic-related function of this endothelial cell-specific adhesion molecule (see, for example, Liao et al. (2002) *Cancer Res.* 62:2567-2575). In preferred embodiments of these combinations, the KSP inhibitor is a compound of formula (II), and it can be a compound of formula IIa, IIb or IIc.

The KSP inhibitors of the invention and the monoclonal antibody can be administered sequentially, in either order, or simultaneously (i.e., concurrently or within the same time frame). Where more than one type of monoclonal antibody is administered, the methods of the present invention can further comprise exposure to radiation and/or chemotherapy as warranted for the cancer undergoing treatment and as recommended by the supervising medical practitioner.

EXAMPLES

Example 1

Assay for Determining KSP Activity

Purified microtubules obtained from bovine brain were purchased from Cytoskeleton Inc. (Denver, Colo., USA). The motor domain of human KSP (Eg 5, KNSL1) was cloned, expressed, and purified to greater than 95% homogeneity. Biomol Green™ was purchased from Affinity Research Products Ltd. (Matford Court, Exeter, Devon, United Kingdom). Microtubules and KSP motor protein (i.e., the KSP motor domain) were diluted in assay buffer (20 mM Tris-HCl (pH 7.5), 1 mM $MgCl_2$, 10 mM DTT and 0.25 mg/mL BSA) to a final concentration of 35 µg/mL microtubules and 45 nM KSP. The microtubule/KSP mixture was then pre-incubated at 37° C. for 10 min to promote the binding of KSP to microtubules.

To each well of the testing plate (384-well plate) containing 1.25 µL of inhibitor or test compound in DMSO (or DMSO only, in the case of controls) were added 25 µL of ATP solution (ATP diluted to a concentration of 300 µM in assay buffer) and 25 µL of the above-described microtubule/KSP solution. The plates were incubated at RT for 1 hour. Following incubation, 65 µL of Biomol Green™ (a malachite green-based dye that detects the release of inorganic phosphate) was added to each well. The plates were incubated for an additional 5-10 minutes then the absorbance at 630 nm was determined using a Victor II plate reader. The amount of absorbance at 630 nm corresponded to the amount of KSP activity in the samples. The $IC_{50}$ of each inhibitor or test compound was then determined based on the decrease in absorbance at 630 nm at each concentration, via nonlinear regression using either XLFit for Excel or Prism data analysis software by GraphPad Software Inc.

Preferred compounds of the invention have a biological activity as measured by an $IC_{50}$ of less than about 1 mM, with preferred embodiments having biological activity of less than about 25 µM, with particularly preferred embodiments having biological activity of less than about 1000 nM, and with the most preferred embodiments having biological activity of less than about 100 nM. Compounds of Formula II were tested in this assay and were found to have $IC_{50}$ values below the limits of quantitation for this assay (estimated to be 2-4 nM).

Example 2

Inhibition of Cellular Proliferation in Tumor Cell Lines Treated with Compound IIa Cell lines used were as follows: HCT-116 (National Cancer Institute's DCTF Tumor Repository, catalog #NCI-502568, Rockville, Md.), HCT-15 (National Cancer Institute's DCTF Tumor Repository, catalog#NCI-502711, Rockville, Md. available from American Type Tissue Collection, catalog #CLL-225), KB-3-1 (available from DSMZ, Deutsche Sammlung von Mikroorganismen und Zellkulturen GmbH (German Collection of Microorganisms and Cell Cultures—catalog number ACC 158), KB-V1 (available from DSMZ—catalog number ACC 149), AGS (available from American Type Culture Collection, Manassas Va., catalog number CRL-1739™), N87 (available from American Type Culture Collection, Manassas Va., catalog number CRL-5822), Hel92.1.7 (available from American Type Culture Collection, Manassas Va., catalog number TIB 180), K562 (available from American Type Culture Collection, Manassas Va., catalog number CRL-243™), MV4;11 (American Tissue Culture Collection, Manassas Va., catalog number CRL-9591) and U937 (available from American Type Culture Collection, Manassas Va., catalog number CRL-1593.2).

Cells were plated in 96-well plates at densities of about 500 cells per well of a 96-well plate and allowed to grow for 24 hours. The cells were then treated with various concentrations of compounds for 72 hours. Then, 100 µl of CellTiter-Glo® reagent was added (Promega Corporation). CellTiter-Glo® is used in a homogeneous method of determining the number of viable cells using the single CellTiter-Glo® reagent to detect ATP (U.S. Pat. Nos. 6,602,677 and 7,241,584) (see Promega product catalog #G7570). Following the addition of the CellTiter-Glo® reagent, the cells were incubated in the dark for 30 minutes. The amount of luminescence was determined for each well using a Wallac Trilux plate reader, which correlates with the number of cells per well. The number of viable cells in the wells that receive only DMSO (0.5%) served as an indication of 0% inhibition, while wells without cells served as 100% inhibition of cell growth. The compound concentration that resulted in a 50% growth inhibition (GI50) was determined graphically from sigmoidal dose-response curves of log-transformed dose values versus cell counts (percent of control) at 72 hours of continuous compound exposure. The data is presented below in Table 1. Broad anti-proliferative effects (GI50 values 0.1-6.5 nM) were observed in all cell lines tested. This broad activity is consistent with a compound that is a mitotic inhibitor.

TABLE 1

In vitro anti-proliferative activity (GI50 values in nM) of Compound IIa.

| Tumor type | Cell line | GI50 (nM) | # tests | Doubling time (hrs) |
| --- | --- | --- | --- | --- |
| Colon | HCT-116 | 0.1 | 4 | 22 |
| Colon | HCT-15 | 0.3 | 9 | 34 |
| Epidermoid | KB3.1 | 0.6 | 15 | 24 |
| Epidermoid | KB8.5 | 0.5 | 16 | 24 |
| Epidermoid | KBV1 | 6.5 | 11 | 29 |
| Gastric | AGS | 0.2 | 4 | 20 |
| Gastric | N87 | 1.0 | 2 | 47 |
| Leukemia | Hel92.1.7 | 0.5 | 4 | 18 |
| Leukemia | K562 | 0.1 | 4 | 30 |
| Leukemia | MV4-11 | 0.2 | 2 | 36.5 |
| Leukemia | U937 | 0.1 | 4 | 24 |

P-glycoprotein (P-gp, also known as MDR1) is an efflux pump that is an ABC transporter that mediates multi-drug resistance against several cytotoxic drugs in cells that express it. Some cell lines used in this study (HCT-15, KBV1, and KB8.5) express P-gp and as can be observed from Table 1, these cell lines are sensitive to the KSP inhibitors of Formula II. Example 12 below demonstrates that similar compounds of Formula I that lack a hydroxyl on the acyl moiety are not active in vivo against such tumors.

Example 3

In Vitro Effect of KSP Inhibitors on Cell Cycle Profile in Cancer Cell Lines Lymphoma cell line cells were treated with the KSP inhibitors of the invention and analyzed by FACs analysis. Approximately $2 \times 10^5$ cells were harvested, cell pellets were washed with cold PBS twice and re-suspended in 500 µL cold PBS. Cells were fixed by adding 8 mL cold 80% ethanol while vortexing slowly. After 15 minutes of incubation fixed cells were washed twice with PBS and cell pellets were re-suspended in 1 mL of PI/RNASE staining buffer (BD Pharmingen™ catalog #550825) and incubated for 15 minutes at 37° C. protected from light. Propidium iodide (PI) is a fluorescent vital dye that stains both DNA and RNA. Therefore the RNA must be removed by digestion with ribonuclease (RNase). Stained cells were passed through a cell strainer into a FACS tube to reduce the number of cell aggregates (BD Falcon #352235) prior to FACS analysis. The DNA content of the fixed and stained cells was analyzed by the BD FACSCalibur flow cytometer using the CellQuest software.

Treatment of cancer cells with the KSP inhibitors resulted in mitotic arrest, but the extent of arrest, its duration, and the consequences following arrest can vary among cell lines. Following mitotic arrest, cells have several options including coming out of arrest and dividing normally, undergoing apoptosis directly, or exiting mitosis without cytokinesis (a phenomenon called mitotic slippage). If cells undergo mitotic slippage, they can enter a pseudo-G1 and then either continue to cycle, senesce, or undergo apoptosis. Some of these differences are highlighted in the treatment of the lymphoma cell lines SUDHL-4 (a B Cell Lymphoma cell line obtained from DSMZ, Deutsche Sammlung von Mikroorganismen und Zellkulturen GmbH (German Collection of Microorganisms and Cell Cultures, catalog number ACC 495) and RL (a human Non-Hodgkin's lymphoma cell line, American Type Culture Collection, Manassas Va., catalog number CRL-2261™) with the KSP inhibitors.

Figure 2:
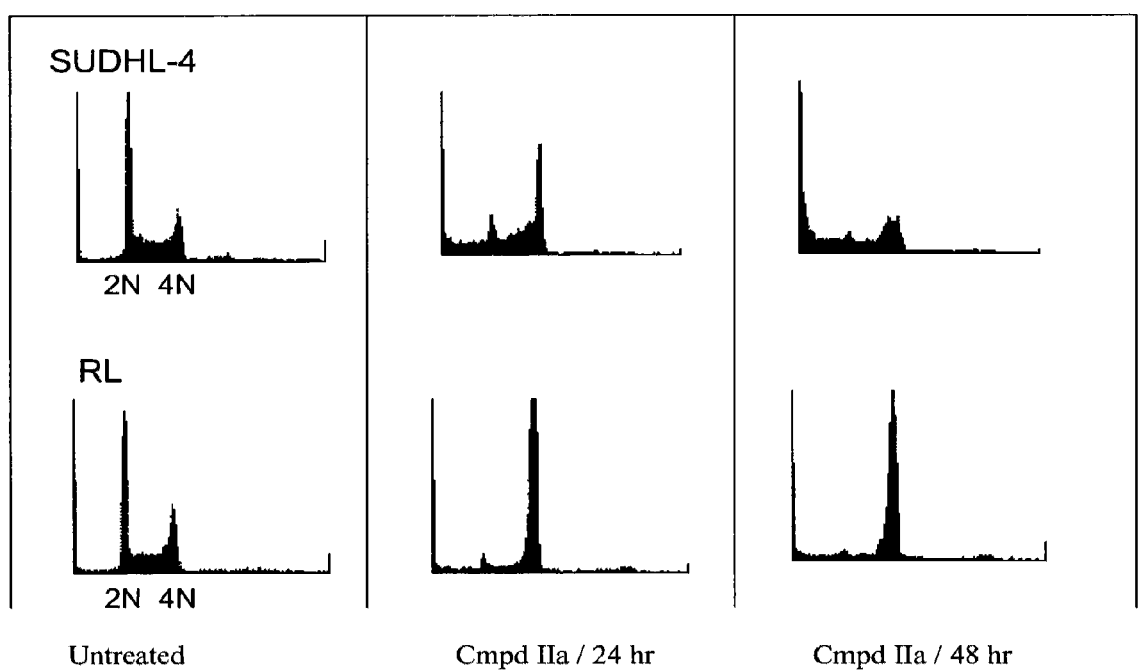
FIG. 2. Cell stage assessment by FACS for SUDHL-4 and RL cell lines treated with Compound IIa: the first column shows untreated cells, the second column shows the cells after 24 hrs with Compound IIa, and the third column shows the cells 48 hours after treatment with Compound IIa.

Both cell lines arrested in mitosis in response to compound IIa, but SUDHL-4 cells underwent apoptosis after 48 hr treatment as indicated by an increase of cells with <2N DNA content, while the RL lymphoma cells remained arrested in mitosis and neither induction of apoptosis nor mitotic slippage occurs. See FIG. 2.

Example 4

KSP Inhibitor Screening Assays

Identification of tumor types that are the most sensitive to the KSP inhibitors of the present invention can be accomplished using an unbiased approach that uses several cell-based assays. The assays chosen were as follows:

CellTiter-Glo®. This is an assay designed to measure ATP concentration in a cell culture, and can be correlated to cell number. Briefly CellTiter-Glo® (Promega Corporation) is a homogeneous method using the single CellTiter-Glo® reagent to detect ATP wherein ATP in the assay drives the activity of a thermostable luciferase to create a luminescent signal which can then be measured and correlated with the number of viable cells. Briefly, for adherent cells, 1,000 to 5,000 cells/well were plated in 96-well plates (100 µl/well) and let to adhere for 24 hours before being treated with drug. For non-adherent cells, 1,000 to 10,000 cells/well were plated in 96-well plates (100 µl/well) and immediately treated with drug. Drug dilutions were prepared in DMSO at 1000 times the final concentration. These dilutions were then diluted 1/100 in growth media before being added to the cells (11 µl/well) to achieve the desired final concentration. After 48 h in a 37° C. tissue culture incubator, the plates were processed for the CellTiter-Glo®assay according to the manufacturer's instructions. Protocol for a 72 hour cell proliferation assay: The 72 hour assay was performed the same way as the 48 hour assay except for the following modifications: For adherent cells, 500 to 5,000 cells/well were plated in 96-well plates (90 µl/well cell growth media) and left to adhere for 24 hours before being treated with drug. For non-adherent cells, 1,000 to 10,000 cells/well were plated in 96-well plates (90 µl/well cell growth media) and immediately treated with drug. Data values presented represent the concentration of test compound required for a 50% reduction in growth.

LDH release. The Cytotoxicity Detection KitPLUS (LDH) assay (Roche Diagnostics, Manheim, Germany) measures the amount of LDH released in the media by dying cells; LDH catalyzes the conversion of lactate into pyruvate. The enzymatic reaction is coupled to a chemical reaction that uses a tetrazolium salt to form a formazan that is red and can be detected by its absorbance at 490 nm. This assay measures the amount of cell death after drug treatment. Cells were plated at 10,000 cells/well in 96-well plates (100 µl/well). Adherent cells were let to adhere for 24 hours before being treated with drug, whereas non-adherent cells were immediately treated with drug. Drug dilutions were prepared in DMSO at 1000 times the final concentration. These dilutions were then diluted 1/100 in growth media before being added to the cells (11 µl/well) to achieve the desired final concentration. After 48 h in a 37° C. tissue culture incubator, the plates were processed for the Cytotoxicity Detection KitPLUS (LDH) assay according to the manufacturer's instructions. The media only values were subtracted from all the data points before analysis. Data values presented correspond to the compound concentration wherein LDH output is at half maximal level.

Caspase-Glo® 3/7. The Caspase-Glo® 3/7 Assay (Promega Corporation) is a homogeneous luminescent assay that measures caspase-3/7 activities. The assay provides a proluminescent caspase-3/7 DEVD-aminoluciferin substrate and a thermostable luciferase in a reagent optimized for caspase-3/7 activity, luciferase activity and cell lysis. Adding the single Caspase-Glo® 3/7 Reagent results in cell lysis, followed by caspase cleavage of the substrate. This liberates free aminoluciferin, which is consumed by the luciferase, generating a luminescent signal. The signal is proportional to caspase-3/7 activity. Data values presented correspond to the compound concentration wherein caspase 3/7 activity is at half maximal level.

Five cell lines were chosen with known differing sensitivities to the KSP inhibitors of the invention in an effort to demonstrate the predictive nature of the screening assays. The lines are as follows:

HCT-116 and HT29. HCT-116 is a cell line derived from a human colonic epithelial carcinoma, and has been shown to be sensitive to the KSP inhibitors of the invention in vivo. HT29 (available from American Type Culture Collection, Manassas Va., catalog number HTB-38) is also derived from a human colonic epithelial carcinoma, but is less sensitive to the KSP inhibitors.

MV4; 11 (American Tissue Culture Collection (catalog # CRL-9591, Rockville, Md.) is an acute myelogenous leukemia (AML) cell line.

Colo205 (American Tissue Culture Collection (catalog # HB-8307, Rockville, Md.) is a human colorectal cancer cell line.

T47D (available from American Tissue Culture Collection (catalog #HTB-133, Rockville, Md.) is a cell line derived from a human breast ductal carcinoma that appears to have a defect in the spindle checkpoint).

The data for Compound IIa is presented below in Table 2. The results demonstrate that generally the assays are in good agreement with each other and can be used in broad screens of varying cell types to screen KSP inhibitors and to screen for sensitive cell types.

TABLE 2

Proliferation/Survival screening assays

| Cell line | CTG Assay (nM) | | | LDH Assay (nM) | | | Caspase 3/7 Assay (nM) | | |
|---|---|---|---|---|---|---|---|---|---|
| | 24 h | 48 h | 72 h | 24 h | 48 h | 72 h | 24 h | 48 h | 72 h |
| MV4; 11 | 0.05 | 0.04 | 0.04 | NS | 0.03 | NS | 0.02 | 0.03 | NS |
| HCT-116 | >5 | 0.11 | 0.13 | 0.06 | 0.10 | 0.10 | 0.12 | 0.09 | NS |
| Colo-205 | >5 | 0.18 | 0.19 | NS | 0.11 | 0.16 | 0.13 | 0.21 | 0.19 |
| HT29 | >5 | >5 | 0.21 | NS | 0.35 | 0.27 | NS | NS | NS |
| T47-D | >5 | >5 | 0.45 | NS | 0.32 | 0.33 | NS | 0.39 | 0.40 |

CTG assay-results are GI50 values wherein GI50 value is calculated as the compound concentration resulting in a 50% survival rate.
LDH assay-results are EC50 values wherein EC50 values are calculated as the compound concentration resulting in the half-maximal effect.
Caspase 3/7 assay-results are EC50 values wherein EC50 values are calculated as the compound concentration resulting in the half-maximal effect.

Example 5

Activity of KSP Inhibitors Against NCI60 Panel of Cell Lines

The NCI-60 panel is a standardized panel of tumor cell lines that is often used to investigate the sensitivity of tumors from different origins to a given agent (Shoemaker 2006 *Nat Rev Cancer;* 6:813-23.) The CellTiter-Glo® assay described above was used to measure sensitivity of a number of tumor derived cell lines to the KSP inhibitor compounds. The data for Compound IIa is presented below in Table 3, and demonstrates that many tumor derived cell lines are sensitive to the KSP inhibitors of the invention.

TABLE 3

Summary of the CellTiter-Glo data for Compound IIa.

| Cell Panel | Cell Line | GI$_{50}$ | Log(GI$_{50}$) | Differential |
|---|---|---|---|---|
| Leukemia | CCRF-CEM | 0.215 | −0.6676 | 0.999 |
| Leukemia | HL-60 | 0.165 | −0.7825 | 1.114 |
| Leukemia | K-562 | 0.218 | −0.6615 | 0.993 |
| Leukemia | MOLT-4 | 0.331 | −0.4802 | 0.811 |
| Leukemia | RPMI-8226 | 0.351 | −0.4547 | 0.786 |
| Leukemia | SR | 0.095 | −1.0223 | 1.353 |
| NSCL | A549 | 10 | 1.0000 | −0.669 |
| NSCL | EKVX | 10 | 1.0000 | −0.669 |
| NSCL | HOP-62 | 10 | 1.0000 | −0.669 |
| NSCL | HOP-92 | 10 | 1.0000 | −0.669 |
| NSCL | NCI-H226 | 10 | 1.0000 | −0.669 |
| NSCL | NCI-H23 | 0.223 | −0.6517 | 0.983 |
| NSCL | NCI-H322M | 10 | 1.0000 | −0.669 |
| NSCL | NCI-H460 | 0.378 | −0.4225 | 0.754 |
| NSCL | NCI-H522 | 0.166 | −0.7799 | 1.111 |
| Colon | COLO 205 | 10 | 1.0000 | −0.669 |
| Colon | HCC-2998 | 0.608 | −0.2161 | 0.547 |
| Colon | HCT-116 | 0.138 | −0.8601 | 1.191 |
| Colon | HCT-15 | 0.378 | −0.4225 | 0.754 |
| Colon | HT29 | 10 | 1.0000 | −0.669 |
| Colon | KM12 | 0.423 | −0.3737 | 0.705 |
| Colon | SW-620 | 0.236 | −0.6271 | 0.958 |
| CNS | SF-268 | 10 | 1.0000 | −0.669 |
| CNS | SF-295 | 0.162 | −0.7905 | 1.122 |
| CNS | SF-539 | 0.387 | −0.4123 | 0.743 |
| CNS | SNB-19 | 10 | 1.0000 | −0.669 |
| CNS | SNB-75 | 10 | 1.0000 | −0.669 |
| CNS | U251 | 0.239 | −0.6216 | 0.953 |
| Melanoma | LOX IMVI | 10 | 1.0000 | −0.669 |
| Melanoma | MALME-3M | 10 | 1.0000 | −0.669 |
| Melanoma | M14 | 0.209 | −0.6799 | 1.011 |
| Melanoma | SK-MEL-2 | 2.773 | 0.4429 | −0.112 |
| Melanoma | SK-MEL-28 | 10 | 1.0000 | −0.669 |
| Melanoma | SK-MEL-5 | 10 | 1.0000 | −0.669 |
| Melanoma | UACC-257 | 10 | 1.0000 | −0.669 |
| Melanoma | UACC-62 | 10 | 1.0000 | −0.669 |
| Melanoma | MDA-MB-435 | 0.152 | −0.8182 | 1.149 |
| Ovarian | IGROV1 | 10 | 1.0000 | −0.669 |
| Ovarian | OVCAR-3 | 10 | 1.0000 | −0.669 |
| Ovarian | OVCAR-4 | 10 | 1.0000 | −0.669 |
| Ovarian | OVCAR-5 | 10 | 1.0000 | −0.669 |
| Ovarian | OVCAR-8 | 0.324 | −0.4895 | 0.821 |
| Ovarian | SK-OV-3 | 0.421 | −0.3757 | 0.707 |
| Ovarian | NCI/ADR-RES | 4.18 | 0.6212 | −0.290 |
| Renal | 786-0 | 10 | 1.0000 | −0.669 |
| Renal | A498 | 10 | 1.0000 | −0.669 |
| Renal | ACHN | 10 | 1.0000 | −0.669 |
| Renal | CAKI-1 | 10 | 1.0000 | −0.669 |
| Renal | RXF 393 | 10 | 1.0000 | −0.669 |
| Renal | SN12C | 10 | 1.0000 | −0.669 |
| Renal | TK-10 | 10 | 1.0000 | −0.669 |
| Renal | UO-31 | 10 | 1.0000 | −0.669 |
| Prostate | PC-3 | 10 | 1.0000 | −0.669 |
| Prostate | DU-145 | 0.435 | −0.3615 | 0.693 |
| Breast | MCF7 | 10 | 1.0000 | −0.669 |
| Breast | MDA-MB-231 | 0.333 | −0.4776 | 0.809 |
| Breast | HS 578T | 0.22 | −0.6576 | 0.989 |
| Breast | BT-474 | 10 | 1.0000 | −0.669 |
| Breast | BT-549 | 0.809 | −0.0921 | 0.423 |
| Breast | T-47D | 10 | 1.0000 | −0.669 |
| | Mean | 2.143 | 0.331 | |

GI$_{50}$ value is the compound concentration (expressed in nM) resulting in a 50% survival rate.
Differential: The difference between the mean Log(GI$_{50}$) (0.331) and the Log(GI$_{50}$) of each cell line.
Mean: The geometric mean for the GI$_{50}$ values and the arithmetic mean for the Log(GI$_{50}$) values.

Example 6

Activity of KSP Inhibitors Against Cell Lines Derived from Hematologic Malignancies The data presented in Table 3 demonstrated that the leukemic cell lines were the most sensitive to the KSP inhibitors of the invention. Thus, a panel of several cell lines derived from hematologic malignancies was tested in the CellTiter-Glo® assay described above, and are presented in Table 4 below and in FIG. 1.

TABLE 4

GI$_{50}$ values for Compound IIa against cell lines derived from hematological malignancies

| Disease | Cell Line | Catalog number | GI$_{50}$ (nM) | Log (GI$_{50}$) | Differential |
|---|---|---|---|---|---|
| AML | MV4; 11 | ATCC CRL-9591 | 0.08 | −1.114 | 0.644 |
| AML | MV4; 11Luc | Derived from MV4; 11 | 0.11 | −0.979 | 0.509 |
| AML | AML-193 | ATCC CRL-9589 | 0.11 | −0.959 | 0.489 |
| AML | Kasumi-1 | ATCC CRL-2724 | 0.44 | −0.357 | −0.113 |
| AML | SET-2 | Available from DSMZ ACC608 | 0.34 | −0.469 | −0.001 |

TABLE 4-continued

GI$_{50}$ values for Compound IIa against cell lines derived from hematological malignancies

| Disease | Cell Line | Catalog number | GI$_{50}$ (nM) | Log (GI$_{50}$) | Differential |
|---|---|---|---|---|---|
| AML | MOLM13-Luc | Available from ATCC 30-2001 | 0.23 | −0.645 | 0.175 |
| AML | HL60 | Available from ATCC CCL-240 | 0.17 | −0.783 | 0.313 |
| AML | HL60-Luc | Available from ATCC 30-2001 | 0.51 | −0.297 | −0.173 |
| AML | HEL92 | ATCC TIB-180 | 0.49 | −0.310 | −0.160 |
| CML | K562 | Available from ATCC CCL-243 | 0.21 | −0.680 | 0.210 |
| ALL | CCRF-CEM | ATCC CCL-119 | 0.16 | −0.785 | 0.315 |
| ALL | RS4;11 | ATCC CRL-1873 | 0.10 | −1.000 | 0.530 |
| ALL | MOLT-4 | Available from ATCC CRL-1582 | 0.33 | −0.480 | 0.010 |
| ALL | SEM-Luc | Available from ATCC 30-2001 | 0.15 | −0.824 | 0.354 |
| MM | KMS11 | See Namba et al below | 0.48 | −0.316 | −0.154 |
| MM | KMS11-Luc | Derived from KSM-11 | 0.29 | −0.538 | 0.068 |
| MM | KMS18-Luc | Available from ATCC 30-2001 | 0.52 | −0.286 | −0.184 |
| MM | OPM2 | DSMZ Acc50 | 0.14 | −0.870 | 0.400 |
| MM | KMS26 | Available from JCRB JCRB1187 | 0.24 | −0.620 | 0.150 |
| MM | L363 | Available from DSMZ ACC49 | 0.13 | −0.886 | 0.416 |
| MM | LP1 | Available from DSMZ ACC41 | 0.21 | −0.688 | 0.218 |
| MM | RPMI-8226 | Available from ATCC CRL-8658 ™ | 0.26 | −0.582 | 0.112 |
| MM | H929 | Available from ATCC CRL-9068 | 0.34 | −0.475 | 0.005 |
| MM | H929-Luc | Available from ATCC 30-2001 | 1.69 | 0.227 | −0.697 |
| NHL | RL | ATCC CRL-226 ™ | 20.00 | 1.301 | −1.771 |
| NHL | SuDHL-4 | DSMZ ACC495 | 0.45 | −0.350 | −0.120 |
| NHL | U937 | Available from ATCC CRL-1593.2 | 0.20 | −0.699 | 0.229 |
| NHL | SR | Available from ATCC SLR-2262 | 0.11 | −0.957 | 0.487 |
| NHL | Karpas-299-Luc | Available from ATCC 30-2001 | 20.18 | 1.305 | −1.775 |
| HL | L428 | DSMZ ACC197 | 20.00 | 1.301 | −1.771 |
| HL | KM-H2 | DSMZ ACC 8 | 0.23 | −0.632 | 0.162 |
| | Mean | | 0.34 | −0.470 | |

GI$_{50}$ value is the compound concentration resulting in a 50% survival rate.
Differential: The difference between the mean Log(GI$_{50}$) (−0.470) and the Log(GI$_{50}$) of each cell line.
Mean: The geometric mean for the GI$_{50}$ values and the arithmetic mean for the Log(GI$_{50}$) values. (KMS-11, see Namba et al (1989) *In Vitro Cell Dev. Biol.* 25 (8) p. 723-729)

Example 7

Sensitivity of Primary Blast Cells to KSP Inhibitors

The data from Table 4 demonstrates that several types of hematological cancer cell lines are sensitive to the KSP inhibitors of the invention. Primary blast cells from AML patients were tested for sensitivity to compound IIa as shown below. Frozen AML blasts from peripheral blood were obtained from AllCell LLC. (Emeryville, Calif.). Three frozen vials containing ~1×10$^7$ PBMCs were purchased. Peripheral blood mononuclear cells (PBMCs) from three newly diagnosed AML patients with a high percentage of blasts (#06-188, 80%; #06-366, 88%; #06-503, 73%) were cultured for several weeks and treated with the KSP inhibitors. The vials were rapidly thawed and the cells were cultured in Iscove's DMEM supplemented with 10% FBS and the following cytokines all at 10 ng/ml: GM-CSF, G-CSF, SCF, IL-3, and IL-6 (all from R&D Systems). Three assays were performed on the cells as follows:

CellTiter-Glo® assay on AML blasts. PBMCs containing AML blasts were seeded in 96-well plates (5000/well) and treated with various concentrations of the compound IIa (10 pM to 10 nM) for 48 hours before cells survival was measured as described above. GI50 values (nM) were calculated as for cell lines.

Cell cycle analysis using propidium iodide staining. PBMCs containing AML blasts were seeded in 6 well plates (0.6 to 1×10$^{06}$ cells/well) and treated with one of the following: DMSO (vehicle), Compound IIa at 0.2 or 2 nM, or Paclitaxel at 100 nM. Approximately 2×10$^5$ cells were harvested, cell pellets were washed with cold PBS twice and re-suspended in 500 μL cold PBS. Cells were fixed by adding 8 mL cold 80% ethanol while vortexing slowly. After 15 minutes of incubation fixed cells were washed twice with PBS and cell pellets were re-suspended in 1 mL of PI/RNASE staining buffer (BD Biosciences #550825) and incubated for 15 minutes at 37° C. protected from light. Propidium iodide (PI) is a fluorescent vital dye that stains both DNA and RNA. Therefore the RNA must be removed by digestion with ribonuclease (RNase). Stained cells were passed through a cell strainer into a FACS tube to reduce the number of cell aggregates (BD Falcon #352235) prior to FACS analysis. The DNA content of the fixed and stained cells was analyzed by the BD FACSCalibur flow cytometer using the CellQuest software.

Colony formation assay in methylcellulose containing medium. Semi-solid medium containing methylcellulose was purchased from StemCell Technologies Inc. (Methocult™ GF+H4435, Cat #04435). Blasts were seeded at densities ranging from 1×10$^3$ to 1×10$^5$ cells/well in non-tissue culture treated 6-well plates. DMSO (vehicle) or compound IIa (0.1, 0.2, 0.5, 1 and 2 nM) was added to the media at the same time as the cells. Colonies were counted under a microscope after 2 weeks. Live cells were stained with P-Iodonitrotetrazolium 750 μl/well at 1 mg/ml (Sigma Cat#18377); pictures were taken after an overnight incubation at 37° C.

Results: Although the apparent doubling time of these blasts was slower than that of most AML cell lines, 50-70 h versus 30-50 h, GI$_{50}$ values were obtained for compound IIa (0.12, 0.28 and 0.34 nM) were in line with that shown above for AML cell lines. Similar results were obtained using the colony formation assay, where the number of colonies was markedly reduced at 0.2 in M and colonies were absent at 0.5 nM and above for sample #06-366. Similar results were obtained for samples #06-188 and #06-503, in all cases colonies were absent at 0.5 nM and above. The cell cycle profile showed that for sample #06-366 at 24 hours there was an increase in the number of cells arrested in mitosis (4N population) followed at 48 hours by an increase in the number of dying cells (<2N population). These changes were more marked at the highest concentration (2 nM) than at the lower concentration (0.2 nM), which is near the GI$_{50}$. A high dose of Paclitaxel (100 nM) was used as a positive control for a strong mitotic arrest. Similar results were obtained for samples #06-188 and #06-503. For sample #06-503 data was collected at the 48 and 72 hour time points. The pattern at 48 hours is similar to that observed for sample #06-366 and at 72 hours the increase in the number of dying cells (<2N population) is more marked, especially at 2 nM. See FIG. 2. The fact that the G150 values are still very low indicates that cells that enter the cell cycle are very effectively killed by compound IIa.

Example 8

In Vivo Efficacy Determination of KSP Inhibitors

The cell line HCT-116 has been widely used in the evaluation of mitotic inhibitors such as microtubule disruptors, mitotic kinase inhibitors and KSP inhibitors. A multi-dose efficacy study on a four times per day for three days (q4d×3) dosing schedule was performed. Experiments were performed using outbred athymic nu/nu mice approximately 6-8 weeks old (Charles River Laboratories, Hollister, Calif.). Upon arrival, animals received a subcutaneous microchip implant (AVID, Folsom, La.) in the subscapular region for identification of individuals. Animals were allowed to acclimatize for 1 week before any experimental procedures began. Mice were housed 4-5 animals per cage in clear polycarbonate micro-isolator cages with a 12-hour light, 12-hour dark cycle at temperatures between 70-80 degrees Fahrenheit and 30-70% relative humidity. Food (Purina rodent chow pellets) and water were provided ad libitum. Mice were handled in accordance with Novartis ACUC regulations and guidelines and the ILAR Guide for the Care and Use of Laboratory Animals. Experiments were performed in an AAALAC accredited facility under an ACUC approved protocol.

Compound IIa (free base) and SB-715992 (ispinesib, a KSP inhibitor by Cytokinetics that is in clinical trials; as its free base) were formulated in 20% Captisol® for all the above doses for a dose volume of 8 mL/kg. Doses were adjusted to each animal's body weight. Formulations were made once at the beginning of study and stored at room temperature. Clinical grade paclitaxel was purchased pre-mixed in a cremophor-based vehicle (Mayne Pharma, now Hospira, Lake Forest, Ill., catalog #NDC-6170334209) and diluted in sterile saline to provide a dose volume of 16 mL/kg for a 30 mg/kg dose administered i.p.

Human HCT116 colon carcinoma cells were obtained from the National Cancer Institute's DCTD Tumor Repository (catalog #NCI-502568, Rockville, Md.) and tested to be free of *Mycoplasma* sp. and murine viruses in the IMPACT1 PCR assay panel (RADIL, University of Missouri, Columbia, Mo.). HCT116 cells were grown in RPMI 1640 with 2 mM L-glutamine (Mediatech Inc., catalog #15-040-CV) supplemented with 10% fetal bovine serum (JRH Biosciences, catalog #12003-1000M). These cells were grown as adherent cultures, maintained at 37° C. in a humidified atmosphere containing 5% carbon dioxide. Cells were cultured for fewer than 10 passages prior to use. Cells were harvested at 95% confluency, and centrifuged at ~800×g for 5 minutes at 4° C. and then resuspended in a cold HBSS (Mediatech Inc., catalog #21-021-CV) at a concentration of 50 million cells/mL for implantation subcutaneously (injection volume of 0.1 mL).

Female nu/nu mice (Charles River, Hollister, Calif.) were injected subcutaneously in the right flank with 5 million HCT-116 tumor cells suspended in Hank's Balanced Salt Solution (HBSS) in a total volume of 0.1 mL/mouse. For the efficacy studies, mice were randomized 10 days post-implant. 72 mice in Study 1 and 81 mice in study 2 were enrolled with a mean tumor volume of approximately 300 mm$^3$. Tumor xenografts were measured in two dimensions (L and W) with digital calipers twice weekly from the start of dosing on Day 0. Tumor volume was calculated as (L×W2)/2. Body weights were measured twice weekly and clinical observations were recorded daily. Tumor volume and body weights were captured and stored by StudyDirector software (StudyLog, South San Francisco, Calif.). Percent treatment/control (T/C) values were calculated using the following formula:

% $T/C = 100 \times \Delta T/\Delta C$ where:
T=mean tumor volume of the drug-treated group on the final day of the study;
ΔT=mean tumor volume of the drug-treated group on the final day of the study−mean tumor volume of the drug-treated group on initial day of dosing;
C=mean tumor volume of the control group on the final day of the study; and
ΔC=mean tumor volume of the control group on the final day of the study−mean tumor volume of the control group on initial day of dosing.

All data were expressed as mean and SEM. Between-groups comparisons for final tumor measurements were performed using the one-way ANOVA pair-wise analysis. Significance was determined using Kruskal-Wallis one-way ANOVA on Ranks and Dunn's method for multiple pair-wise comparisons. Statistical analysis was carried out using SigmaStat (Systat Software Inc., San Jose, Calif.).

A multi-dose efficacy study on a q4d×3 schedule was conducted to compare the antitumor activity of compound IIa to SB-715992 and paclitaxel. The results are shown in Table 5. In this study, the animals treated at the highest doses of 5 mg/kg compound IIa and 15 mg/kg SB-715992 only received the first two doses of the planned q4d×3 schedule due to significant weight loss, from which mice recovered. Even with only two doses, there was significant tumor regression in a similar manner (73% regression, p<0.05 for each). The two lower doses of 2.5 and 1.25 mg/kg compound IIa and 7.5 mg/kg SB-715992 given q4d×3 also similarly caused regression of HCT116 tumor xenografts (82%, 66%, 65% regression, p<0.05, respectively). Overall, paclitaxel was less effective than compound IIa; although tumors regressed initially, growth resumed soon after the cessation of dosing.

TABLE 5

Efficacy of compound IIa administered on a q4d × 3 dose schedule in the HCT116 tumor xenograft model.

| Compound | Dose, route, schedule | Tumor response | | | Host response | | |
|---|---|---|---|---|---|---|---|
| | | T/C, Day 1 7 (%) | Δ Tumor volume, Day 17 (mm$^3$) | Max. % Regression (Day) | Max. Δ body weight (Day) (g) | Max. Δ body weight (Day) (%) | Survival (alive/total) |
| Vehicle (20% Captisol ®) | q4d × 3, i.v. | 100 | 756 ± 95 | — | 0.9 ± 0.5 (D11) | 3.4 ± 0.02 (D11) | 9/9 |
| Cmpd IIa | 1.25 mg/kg, i.v., q4d × 3 | —* | −173 ± 12 | 66 (D20) | −0.7 ± 0.3 (D4) | −2.9 ± 0.01 (D4) | 9/9 |

TABLE 5-continued

Efficacy of compound IIa administered on a q4d × 3 dose schedule in the HCT116 tumor xenograft model.

| Compound | Dose, route, schedule | Tumor response | | | Host response | | |
|---|---|---|---|---|---|---|---|
| | | T/C, Day 17 (%) | Δ Tumor volume, Day 17 (mm³) | Max. % Regression (Day) | Max. Δ body weight (Day) (g) | Max. Δ body weight (Day) (%) | Survival (alive/total) |
| Cmpd IIa | 2.5 mg/kg, i.v., q4d × 3 | —* | −208 ± 17 | 82 (D20) | −1.8 ± 0.2 (D11) | −7.0 ± 0.03 (D11) | 9/9 |
| Cmpd IIa | 5 mg/kg, i.v., q4d × 3 | —* | −196 ± 11 | 73 (D20) | −3.0 ± 0.2 (D7) | −11.7 ± 0.02 (D7) | 8/9 (body weight loss) |
| SB-715992 | 3.5 mg/kg, i.v., q4d × 3 | 5 | 39 ± 4 | 10 (D11) | −0.7 ± 0.05 (D4) | −2.7 ± 0.17 (D4) | 9/9 |
| SB-715992 | 7.5 mg/kg, i.v., q4d × 3 | —* | −177 ± 55 | 65 (D17) | −0.3 ± 0.05 (D4) | −1.3 ± 0.25 (D4) | 9/9 |
| SB-715992 | 15 mg/kg, i.v., q4d × 3 | —* | −205 ± 24 | 73 (D20) | −2.5 ± 0.2 (D7) | −10.6 ± 0.75 (D7) | 9/9 |
| Paclitaxel | 30 mg/kg, i.p., q4d × 3 | —* | −80 ± 3 | 31 (D17) | −1.3 ± 0.1 (D7) | −5.0 ± 0.46 (D7) | 9/9 |

Since a dose as low as 1.25 mg/kg on a q4d×3 schedule induced regression of HCT116 xenografts, the efficacy study was repeated with a range of doses from 2 to 0.125 mg/kg to observe a dose response and determine how low a dose can be given to induce tumor regression. The results in Table 6 indicate that regression of tumors was observed as low as 1 mg/kg (46% regression, $p<0.05$, day 17) and tumor stasis was observed as low as 0.25 mg/kg of compound IIa during the dosing interval, but did not reach statistical significance compared to the vehicle control group. The anti-tumor effect of compound IIa at 0.125 mg/kg was not significantly different from vehicle control. Only the 7.5 mg/kg dose of SB-715992 induced tumors to regress. Additionally, 72 hrs after the last dose, blood was collected to compare the circulating neutrophil levels among groups. Neutrophils were reduced in a dose responsive manner, similar to the tumor efficacy effect.

TABLE 6

Efficacy of low doses of Compound IIa administered on a q4d × 3 dose schedule in the HCT116 tumor xenograft model.

| Compound | Dose, route, schedule | Tumor response | | | Host response | | | |
|---|---|---|---|---|---|---|---|---|
| | | T/C, Day 24 (%) | Δ Tumor volume, Day 24 (mm³) | Max. % Regression (Day) | Neutrophils/ul 72 h post-dose +/− S.D. | Max. Δ body weight (Day) (g) | Max. Δ body weight (Day) (%) | Survival (alive/total) |
| Vehicle (20% Captisol ®) | q4d × 3, i.v. | 100 | 1104 ± 262 | — | 1227 +/− 257 | −0.1 ± 0.2 (D3) | −0.4 ± 0.86 (D3) | 9/9 |
| Cmpd IIa | 0.125 mg/kg, i.v., q4d × 3 | 81 | 809 ± 193 | — | 1346 +/− 427 | −0.4 ± 0.16 (D3) | −1.4 ± 0.59 (D3) | 9/9 |
| Cmpd IIa | 0.25 mg/kg, i.v., q4d × 3 | 35 | 382 ± 120 | — | 785 +/− 374 | −0.6 ± 0.15 (D3) | −2.3 ± 0.58 (D3) | 9/9 |
| Cmpd IIa | 0.5 mg/kg, i.v., q4d × 3 | 14 | 155 ± 145 | 8 (D14) | 293 +/− 29 | −0.7 ± 0.18 (D3) | −2.7 ± 0.75 (D3) | 9/9 |
| Cmpd IIa | 1 mg/kg, i.v., q4d × 3 | —* | −34 ± 36 | 46 (D17) | 343 +/− 255 | −0.7 ± 0.23 (D3) | −2.8 ± 0.83 (D3) | 9/9 |
| Cmpd IIa | 2 mg/kg, i.v., q4d × 3 | —* | −141 ± 48 | 73 (D21) | 193 +/− 125 | −1.35 ± 0.87 (D10) | −4.7 ± 1.17 (D3) | 8/9 (body weight loss) |
| SB-715992 | 1.75 mg/kg, i.v., q4d × 3 | 36 | 395 ± 84 | — | 1026 +/− 229 | −0.6 ± 0.58 (D3) | −2.3 ± 0.51 (D3) | 9/9 |
| SB-715992 | 3.5 mg/kg, i.v., q4d × 3 | 15 | 165 ± 60 | 13 (D7) | 731 +/− 391 | −0.5 ± 0.37 (D3) | −2.0 ± 0.44 (D3) | 9/9 |
| SB-715992 | 7.5 mg/kg, i.v., q4d × 3 | — | −145 ± 25 | 65 (D21) | 476 +/− 112 | −0.7 ± 1.1 (D10) | −3.0 ± 2.49 (D10) | 9/9 |

Example 9

Efficacy of KSP Inhibitors in HCT15 Tumor Xenograft Model

HCT15 is a human adenocarcinoma cell line also known to express the P-gp pump. Thus a xenograft tumor model was performed using this cell line to verify the results from Example 10.

Experiments were performed using outbred athymic nu/nu mice (Charles River Laboratories) approximately 6-8 weeks old. Upon arrival, animals received a subcutaneous microchip implant (AVID, Folsom, La.) in the subscapular region for identification of individuals. Animals were allowed to acclimatize for 1 week before any experimental procedures began. Routine animal care and assurance of welfare were as described above.

Human HCT15 colon carcinoma cells were obtained from the National Cancer Institute's DCTD Tumor Repository (catalog #NCI-502711, Rockville, Md.). HCT15 cells were grown in RPMI 1640 with 2 mM L-glutamine (Mediatech Inc., catalog #15-040-CV) supplemented with 10% fetal bovine serum (JRH Biosciences, catalog #12003-1000M). The cells were tested to be free of *Mycoplasma* sp. and murine viruses in the IMPACT1 PCR assay panel (RADIL, University of Missouri, Columbia, Mo.)

These cells were grown as adherent cultures, maintained at 37° C. in a humidified atmosphere containing 5% carbon dioxide. Cells were cultured for fewer than 10 passages prior to use. Cells were harvested at 95% confluency, and centrifuged at ~800×g for 5 minutes at 4° C. and then resuspended in a 1:1 ratio of HBSS (Mediatech Inc., catalog #21-021-CV) plus Matrigel™ at a concentration of 50 million cells/mL for implantation subcutaneously (injection volume of 0.2 mL).

Treatments for the efficacy studies were initiated 10 days following tumor cell implantation when tumors were approximately 300 mm$^3$. Compound IIa and SB-715992 were administered intravenously (i.v.) via the tail vein in a volume of 8 mL/kg at the doses indicated. Paclitaxel was administered intraperitoneally (i.p.) in a volume of 16 mL/kg at 30 mg/kg.

For the efficacy studies, mice were randomized 10 days post-implant and were enrolled with a mean tumor volume of approximately 300 mm$^3$. Tumor xenografts were measured in two dimensions (L and W) with digital calipers twice weekly from the start of dosing on Day 0. Tumor volume was calculated as (L×W2)/2. Body weights were measured twice weekly and clinical observations were recorded daily. Tumor volume and body weights were captured and stored by StudyDirector software (StudyLog, South San Francisco, Calif.). Data was analyzed as described above.

The results in shown in Table 7 indicated that compound IIa demonstrated greater anti-HCT15 tumor efficacy than paclitaxel; at the 4 mg/kg dose, the percent T/C was 26% (p<0.05 vs. vehicle and similar vs. paclitaxel). Although the data shows a separation between 4 mg/kg KSP inhibitor and 7.5 and 15 mg/kg SB-715992 dosed groups, statistical significance was not achieved due to the variability of tumor volumes in this model. On day 10, a statistically significant difference was observed (p<0.05) between 4 mg/kg compound IIa and the 7.5 mg/kg SB-715992 dose. Paclitaxel a known substrate for P-gp has very low antitumor activity in this model. No significant body weight loss or outward signs of toxicity were observed in any of the treated mice. The increased antitumor activity in the HCT15 model demonstrates efficacy of compound IIa in tumor xenograft models that express high levels P-gp.

TABLE 7

Efficacy of Compound IIa administered on a q4d × 3 dose schedule in the HCT15 tumor xenograft model

| Compound | Dose, route, schedule | Tumor response | | | Host response | | |
|---|---|---|---|---|---|---|---|
| | | ΔT/ΔC, Day 15 (%) | Regression (%) | Δ Tumor volume, Day 15 (mm$^3$) | Max. Δ body weight, (Day) (g) | Max. Δ body weight, (Day) (%) | Survival (alive/total) |
| Vehicle (20% Captisol) | 8 mL/kg, q4d × 3, i.v. | 100 | — | 1123 ± 84 | 0.3 ± 0.2 (D10) | 1.4 ± 0.8 (D10) | 9/9 |
| COMPOUND IIa | 1.25 mg/kg, q4d × 3, i.v | 60 | — | 671 ± 172 | −0.5 ± 0.4 (D3) | −2.1 ± 0.6 (D3) | 9/9 |
| COMPOUND IIa | 2.5 mg/kg, q4d × 3, i.v | 65 | — | 735 ± 159 | 0.6 ± 0.2 (D3) | 2.3 ± 0.8 (D10) | 9/9 |
| COMPOUND IIa | 4.0 mg/kg, q4d × 3, i.v | 26* | — | 99 ± 78 | −0.8 ± 0.3 (D10) | −3.2 ± 1.4 (D10) | 9/9 |
| SB-715992 | 7.5 mg/kg, q4d × 3, i.v | 87 | — | 647 ± 164 | 0.6 ± 0.2 (D8) | 2.6 ± 1.0 (D8) | 9/9 |
| SB-715992 | 15 mg/kg, q4d × 3, i.v | 67 | — | 491 ± 109 | −1.2 ± 0.4 (D10) | −4.9 ± 1.4 (D10) | 9/9 |
| Paclitaxel | 30 mg/kg, Q4d × 3, i.p | 104 | — | 703 ± 198 | 0.8 ± 0.6 (D8) | 3.3 ± 1.0 (D8) | 9/9 |

Example 10

Efficacy of KSP Inhibitors in Acute Myelogenous Leukemia (AML) Xenograft Model The efficacy of compound IIa was assessed against the MV4; 11 tumor xenograft model (O'Farrell, et al 2003) in athymic mice. Efficacy was first tested in a subcutaneous MV4; 1 tumor xenograft model in mice, and also, because the bone marrow microenvironment plays an important role in AML cell growth and survival, efficacy was further evaluated in a MV4; 11-luc disseminated disease model in mice, where the cells home to and grow in bone marrow and some soft organs. Due to luciferase expression by the tumor cells, serial comprehensive monitoring of growth of leukemia lesions was determined using bioluminescence imaging.

Subcutaneous tumor efficacy studies were performed using outbred athymic nu/nu mice approximately 6-8 weeks old (Charles River Laboratories, Hollister, Calif.). The efficacy study in the disseminated disease model was performed using immunodeficient NOD-SCID female mice approximately 7-8 weeks old (Jackson Laboratories, Bar Harbor, Me.). Upon arrival, animals received a subcutaneous microchip implant (AVID, Folsom, La.) in the subscapular region for identification of individuals. Animals were allowed to acclimatize for 1 week before any experimental procedures began. Routine animal care and assurance of welfare were as described above.

Human MV4; 11 acute myelogenous leukemia cells were obtained from American Tissue Culture Collection (catalog #CRL-9591, Rockville, Md.) and tested to be free of *Mycoplasma* sp. and murine viruses in the IMPACT1 PCR assay panel (RADIL, University of Missouri, Columbia, Mo.). For the disseminated disease model, a stable pool of MV4; 11 cells expressing the luciferase gene was received from Fangxian Sun at the Genomics Institute of the Novartis Research Foundation in San Diego, Calif. (MV4; 11-luc). The MV4; 11 cells were grown in Iscove's modified Dulbecco's medium (Mediatech Inc., catalog #15-016-CV) supplemented with 10% fetal bovine serum (JRH Biosciences, catalog #12003-1000M), 4 mM L-glutamine and 5 ng/mL recombinant human granulocyte M-CSF (GM-CSF) (R&D Systems, catalog #215-GM). MV4; 11-luc were grown in the same media, but with the addition of 2 micrograms/mL of puromycin for selection of luciferase expression. These cells were grown as suspension cultures, maintained at 37° C. in a humidified atmosphere containing 5% carbon dioxide. Cells were cultured for fewer than 10 passages prior to use. Cells were harvested at approximately 2 million cells/mL, and centrifuged at ~800×g for 5 minutes at 4° C. and then resuspended in a cold HBSS (Mediatech Inc., catalog #21-021-CV) at a concentration of 25 million cells/mL (containing 50% Matrigel™, BD Biosciences, catalog #354234) for implantation subcutaneously (injection volume of 0.2 mL) or at a concentration of 100 million cells/mL for implantation intravenously (i.v.) via the tail vein (injection volume of 0.1 mL). Mice were irradiated with 3 gray for 3 minutes one day prior to the i.v. cell implant.

The compound IIa (free base) and SB-715992 (free base) were formulated in 20% Captisol for a dose volume of 8 mL/kg. Doses were adjusted to each animal's body weight. Formulations were made once at the beginning of study and stored at room temperature. Clinical grade paclitaxel was purchased pre-mixed in cremophor-based vehicle (Mayne Pharma, now Hospira, Lake Forest, Ill., catalog #NDC-6170334209) and diluted in sterile saline to provide a dose volume of 16 mL/kg for a 30 mg/kg dose administered i.p.

For the two efficacy evaluations in the subcutaneous tumor model, 10 million cells combined in a 1:1 mixture of HBSS and Matrigel™ were injected subcutaneously in the right flank in a total volume of 0.2 mL/mouse. Mice were randomized 17 days post-implant, and mice were enrolled with a mean tumor volume of approximately 250 mm$^3$. Tumor xenografts were measured in two dimensions (L and W) with digital calipers twice weekly from the start of dosing on Day 0. Tumor volume was calculated as (L×W2)/2. Body weights were measured twice weekly and clinical observations were recorded daily. Tumor volume and body weights were captured and stored by StudyDirector software (StudyLog, South San Francisco, Calif.).

For the efficacy evaluation in the disseminated disease model, female NOD-SCID mice received whole-body irradiation at 3 gray the day before tail vein injection of 10 million cells in 0.1 mL HBSS. Forty mice were randomized and enrolled on study 28 days post-implant, with a mean photon count (dorsal view+ventral view) of approximately 5×10$^7$ photons/second, as determined by bioluminescence imaging. Approximately 10 minutes prior to imaging, mice were injected i.p. with 150 mg/kg luciferin (Xenogen Corporation, Alameda, Calif.), followed by anesthetization with isoflurane. Photon emission was measured using a charge coupled device camera in the IVIS imaging system (Xenogen Corporation). Briefly, a gray-scale image of the mice was captured, followed by an overlay of a bioluminescence map representing the spatial distribution of photons detected from cleaved luciferin in the cancer cells expressing luciferase. Signal intensity was quantified using a customized version of the IGOR Pro version 4.09A Software (WaveMetrics, Inc., Lake Oswego, Oreg.) called Living Image version 2.50.2 (Xenogen). The sum of all detected photon counts from the dorsal+ventral views was determined. Bioluminescence of cancer cells in the animals was measured by imaging on designated days until the first mice developed hind limb paralysis due to disease burden, the main end point for when to humanely euthanize mice. The day of euthanasia for each mouse was recorded and the remaining percentage of mice surviving was plotted over time (Kaplan-Meier survival analysis). P values were calculated using the log-rank test (GraphPad Prism 4.0 software) to assess differences between treated and control groups (p<0.05 was considered significant). Body weights were measured twice weekly and clinical observations were recorded daily. Body weights were captured and stored by StudyDirector software (StudyLog, South San Francisco, Calif.). Data analysis was performed as described above.

Results, subcutaneous tumor model: The efficacy studies in the subcutaneous tumor model were conducted to compare activity of a range of doses of compound IIa administered q4d×3. In the first study, the highest tolerated doses in nu/nu mice were evaluated; 4 mg/kg compound IIa, 15 mg/kg SB-715992 and 30 mg/kg paclitaxel. Four remaining mice with tumors were administered 0.625 mg/kg of KSP inhibitor on the same schedule. The results are shown in Table 8. Tumor regressions were observed in all treatment groups during the dosing interval, with 9/9, 6/9 and 7/9 mice with sustained, complete tumor regressions (CR) for over 100 days in groups treated with the high doses of compound IIa, SB-715992 and paclitaxel, respectively. Although tumors regressed in the 0.625 mg/kg compound IIa treated group, they grew again approximately 10 days after the last dose. Doses of test agents were generally well tolerated with <10% maximal mean weight loss, although two mice lost>20% body weight in the SB-715992 treated group.

TABLE 8

Efficacy of Compound IIa administered on a q4d × 3 dose schedule in the subcutaneous MV4; 11 tumor xenograft model

| | Tumor response | | | Host response | | |
|---|---|---|---|---|---|---|
| | ΔT/ΔC, Day | % Max | Δ Tumor volume, | Max Δ body | % Max. Δ body | Survival |

| Compound | Dose, route, schedule | 24 (%) | Regression (Day) | Day 24 (mm³) | CR | weight (g) (Day) | weight (Day) | (alive/ total) |
|---|---|---|---|---|---|---|---|---|
| Vehicle (20% Captisol) | q4d × 3, i.v. | 100 | — | 911 ± 101 | 0 | 0.23 ± 0.3, (D10) | 1 ± 1.4 (D10) | 9/9 |
| COMPOUND IIa | 0.625 mg/kg, q4d × 3, i.v. | — | 69 (D10) | −32 ± 172 | 0 | −0.5 ± 1.3 (D7) | −1.7 ± 5.0 (D7) | 4/4 |
| COMPOUND IIa | 4 mg/kg, q4d × 3, i.v. | — | 100, (D60) | −176 ± 31 | 9 | −1.5 ± 0.4 (D10) | −5.9 ± 1.6 (D10) | 9/9 |
| SB-715992 | 15 mg/kg, q4d × 3, i.v. | — | 98 (D60) | −211 ± 28 | 6 | −1.4 ± 0.3 (D3) | −5.6 ± 1.1 (D3) | 7/9 (body weight loss) |
| Paclitaxel | 1 mg/kg, q4d × 3, i.p. | — | 75 (D46) | −151 ± 63 | 7 | 0.4 ± 0.3 (D10) | 0.4 ± 1.1 (D10) | 9/9 |

The second efficacy study in the subcutaneous tumor model was conducted comparing activity of a range of low doses of compound IIa administered q4d×3. The highest dose used was 2 mg/mg, which is half the highest tolerated dose in nude mice. Activity of compound IIa was compared to SB-715992 at 7.5 mg/kg, which is half its highest tolerated dose. The results are shown in Table 9 and in FIG. 2. Tumor regression was observed to varying extents in the 0.5, 1 and 2 mg/kg doses of compound IIa and 1.75, 3.5 and 7.5 mg/kg SB-715992. By 5 days after the last dose, tumors started to grow in the groups treated with the 0.5 mg/kg compound IIa and 1.75 mg/kg SB-715992. Then by 30 days after dosing, tumors started to grow in the 7.5 mg/kg of SB-715992 treated group. The 1 and 2 mg/kg doses of compound IIa caused long term regressions with 6 and 5 complete tumor regressions for over 100 days, respectively. Doses of test agents were generally well tolerated with <10% maximal mean weight loss.

out the body, including to the lung and liver. Therefore, photon emission from the whole body was subsequently recorded (dorsal+ventral views). These lesions ultimately led to hind limb paralysis with occasional significant body weight loss due to tumor burden, at which time mice were sacrificed. This was termed "conditional survival."

Serial whole-body monitoring of photon emission from MV4; 11-luc in mice was conducted until the first mice succumbed to disease, which happened after day 12 of the study. The 0.5 and 1 mg/kg doses of compound IIa administered q4d×3 significantly reduced bioluminescence signal compared with the vehicle treated group (p<0.05), a measure of disease burden while the effect of the 0.25 mg/kg treatment was not significant different from that of the vehicle. Compound IIa was well tolerated at these doses. Compound IIa significantly delayed the induction of hind limb paralysis and

TABLE 9

Study 2: Summary of the antitumor efficacy and tolerability of Compound IIa against MV4; 11 human AML subcutaneous xenograft tumors

| | | Tumor response | | | Host response | | | |
|---|---|---|---|---|---|---|---|---|
| Compound | Dose, route, schedule | ΔT/ΔC, Day 21 (%) | % Max. Regression (Day) | Δ Tumor volume, Day 21 (mm³) | CR | Max. Δ body weight (g) (Day) | % Max. Δ body weight (Day) | Survival (alive/ total) |
| Vehicle (20% Captisol) | q4d × 3, i.v. | 100 | — | 574 ± 84 | 0 | 0.3 ± 0.24 (D10) | 1.1 ± 0.9, D10 | 9/9 |
| COMPOUND IIa | 0.13 mg/kg, q4d × 3, i.v | 161 | — | 921 ± 341 | 0 | −0.6 ± 1.0 (D10) | 2.3 ± 1.7 (D10) | 9/9 |
| COMPOUND IIa | 0.25 mg/kg, q4d × 3, i.v | 133 | — | 765 ± 196 | 0 | 0.2 ± 0.14, (D10) | 0.64 ± 0.5 (D10) | 9/9 |
| COMPOUND IIa | 0.5 mg/kg, q4d × 3, i.v | 20 | 55 (D10) | 114 ± 110 | 0 | −0.6 ± 0.24 (D7) | −2.5 ± 0.8 (D7) | 9/9 |
| COMPOUND IIa | 1 mg/kg, q4d × 3, i.v | — | 89 (D63) | −194 ± 27 | 6 | −0.3 ± 0.2 (D7) | −1.1 ± 0.7 (D7) | 9/9 |
| COMPOUND IIa | 2 mg/kg, q4d × 3, i.v | — | 87 (D63) | −201 ± 23 | 5 | −0.1 ± 0.14 (D3) | −0.4 ± 0.6 (D3) | 9/9 |
| SB-715992 | 1.8 mg/kg, Q4d × 3, i.v | 59 | — | 339 ± 218 | 0 | 0.5 ± 0.4, D10 | 2.0 ± 1.0, D10 | 9/9 |
| SB-715992 | 3.5 mg/kg, Q4d × 3, i.v | 44 | 41 (D10) | 251 ± 132 | 0 | 0.2 ± 0.3, D3 | 0.7 ± 0.3, D3 | 9/9 |
| SB-715992 | 7.5 mg/kg, Q4d × 3, i.v | —* | 75 (D31) | −204 ± 20 | 3 | −0.4 ± 0.8, D10 | −1.4 ± 1.3, D10 | 9/9 |

Results, disseminated AML disease model: The activity of compound IIa was evaluated in a disseminated AML disease model of MV4; 11-luc, in which tumor cells were implanted intravenously. Treatment administration was initiated 28 days after cell implant, at which time animals are in a stage of advanced disease as indicated by extensive bioluminescence signal. The results are shown in Table 10. In the initial imaging, bioluminescence signal was observed in bone (mandible, skull, spine and long bones), but also disseminated throughout the body, including to the lung and liver. Therefore, phoenhanced survival of the mice with all three doses compared with the vehicle-treated cohort (p<0.05). The median survival in the vehicle-treated group was 15 days, whereas that of the 0.25, 0.5 and 1 mg/kg Compound IIa-treated groups was 27, 31 and 30 days, respectively. The early dose dependent reduction in tumor burden (bioluminescence) that occurred during the time of dosing did not translate into a dose dependent increase in survival. It appears that once the compound effect wore off, disease rapidly progressed in all groups.

TABLE 10

Efficacy of compound IIa administered on a q4d × 3 dose schedule in the MV4;11 disseminated disease model

| | | Tumor response | | | Host response | |
|---|---|---|---|---|---|---|
| Compound | Dose, route, schedule | ΔT/ΔC, Day 12 (%) | Regression, Day 12 (%) | Δ Tumor bioluminescence, Day 12 (photons/sec) | Median Day of Survival | Max. Δ body weight (g) (Day) | % Max. Δ body weight (Day) |
| Vehicle (20% Captisol) | q4d × 3, i.v. | 100 | — | $9.2 \times 10^8 \pm 2.6 \times 10^8$ | 15 | $-0.64 \pm 0.16$ (D6) | $-3.6 \pm 0.92$ (D6) |
| COMPOUND IIa | 0.25 mg/kg, q4d × 3, i.v | 46 | — | $4.3 \times 10^8 \pm 2.0 \times 10^8$ | 27** | $1.1 \pm 0.44$ (D5) | $5.6 \pm 1.3$ (D5) |
| COMPOUND IIa | 0.5 mg/kg, q4d × 3, i.v | — | 9* | $-4.0 \times 10^6 \pm 1.3 \times 10^7$ | 31** | $-0.57 \pm 0.45$ (D10) | $-2.6 \pm 2.3$ (D10) |
| COMPOUND IIa | 1 mg/kg, q4d × 3, i.v | — | 80* | $-3.9 \times^7 \pm 1.4 \times 10^7$ | 30** | $-0.77 \pm 0.32$ (D10) | $-4.2 \pm 1.7$ (D10) |

Example 11

Evaluation of the Efficacy of KSP Inhibitors in Human Multiple Myeloma KMS-11-luc Tumor Xenografts The efficacy of compound IIa was evaluated against human multiple myeloma KMS-11-luc tumor xenografts. Efficacy was first tested in a subcutaneous tumor xenograft model in mice with this line, where compound IIa induced a marked anti-tumor effect. Since the bone marrow microenvironment plays an important role in myeloma cell growth and survival, efficacy was further evaluated in a KMS-11-luc disseminated disease model in mice, where the cells preferentially home and grow in the orthotopic site of the bone marrow. Expression of the luciferase reporter gene in the cells allowed serial comprehensive monitoring of growth of myeloma lesions in bone by bioluminescence imaging.

Experiments were performed using immunodeficient SCID-Beige female mice approximately 7-8 weeks old (Charles River Laboratories, Wilmington, Mass.). Upon arrival, animals received a subcutaneous microchip implant (AVID, Folsom, La.) in the subscapular region for identification of individuals. Animals were allowed to acclimatize for 1 week before any experimental procedures began. Routine animal care and assurance of welfare were as described above.

Human KMS-11-luc multiple myeloma cells were obtained from the laboratory of Suzanne Trudel at the University of Toronto (Ontario, Canada) and tested to be free of Mycoplasma sp. and murine viruses in the IMPACT1 PCR assay panel (RADIL, University of Missouri, Columbia, Mo.). Prior to our receiving this cell line, it had been stably engineered to express luciferase by retroviral transfection of the pGC-gfp/luc vector. KMS-11-luc cells were grown in Iscove's medium supplemented with 2 mmol/L L-glutamine (Mediatech, Inc., Hemdon, Va.) and 10% fetal bovine serum (JRH Biosciences, catalog #12003-1000M). These cells were grown as suspension cultures, maintained at 37° C. in a humidified atmosphere containing 5% carbon dioxide. Cells were cultured for fewer than 10 passages prior to use. Cells were harvested at approximately 2 million cells/mL, and centrifuged at ~800×g for 5 minutes at 4° C. and then resuspended in a 1:1 mixture of cold Hank's balanced salt solution (HBSS) and Matrigel™ (Mediatech Inc., catalog #21-021-CV; BD Biosciences, catalog #354234, respectively) at a concentration of 50 million cells/mL for implantation subcutaneously (injection volume of 0.2 mL). Alternatively, for the disseminated disease model, cells were prepared only in cold HBSS at a concentration of 100 million cells/mL for intravenous (i.v.) implantation via the tail vein (injection volume of 0.1 mL).

Compound IIa and SB-715992 (free base) were formulated in 20% Captisol for a dose volume of 8 mL/kg. Doses were adjusted to each animal's body weight. Formulations were made once at the beginning of study and stored at room temperature. Clinical grade paclitaxel was purchased premixed in a cremophor-based vehicle (Mayne Pharma, now Hospira, Lake Forest, Ill., catalog #NDC-6170334209) and diluted in sterile saline to provide a dose volume of 16 mL/kg for a 30 mg/kg dose administered i.p.

For the efficacy evaluation in the subcutaneous tumor model, 10 million cells combined in a 1:1 mixture of HBSS and Matrigel™ were injected subcutaneously in the right flank in a total volume of 200 mL/mouse. Mice were randomized 11 days post-implant, and 54 mice were enrolled with a mean tumor volume of approximately 140 mm³. Tumor xenografts were measured in two dimensions (L and W) with digital calipers twice weekly from the start of dosing on Day 0. Tumor volume was calculated as (L×W2)/2. Body weights were measured twice weekly and clinical observations were recorded daily. Tumor volume and body weights were captured and stored by StudyDirector software (StudyLog, South San Francisco, Calif.). Data analysis was as described above.

For the efficacy evaluation in the disseminated disease model, 10 million cells in HBSS were injected i.v. via the tail vein in a total volume of 100 mL/mouse. Forty mice were randomized and enrolled on study 10 days post-implant, with a mean photon count in the leg bones (right+left) of approximately $9 \times 10^5$ photons/second, as determined by bioluminescence imaging. Approximately 10 minutes prior to imaging, mice were injected i.p. with 150 mg/kg luciferin (Xenogen Corporation, Alameda, Calif.), followed by anesthetization with isoflurane. Photon emission was measured using a charge coupled device camera in the IVIS imaging system (Xenogen Corporation). Briefly, a gray-scale image of the mice was captured, followed by an overlay of a bioluminescence map representing the spatial distribution of photons detected from cleaved luciferin in the cancer cells expressing luciferase. Signal intensity was quantified using a customized version of the IGOR Pro version 4.09A Software (WaveMetrics, Inc., Lake Oswego, Oreg.) called Living Image version 2.50.2 (Xenogen). The sum of all detected photon counts from the right+left legs were determined. Bioluminescence of cancer cells in the animals was measured by imaging on designated days until the first mice developed hind limb 7.5 mg/kg SB-715992 resulted in maximal regression of KMS-11-luc tumors by 56% and 49% (p<0.05), respectively, and tumor regrowth did not occur until approximately 4 weeks after the end of treatment. Doses of test agents were generally well tolerated with <10% maximal mean weight loss, with the exception of the 1 mg/kg dose of compound IIa, which resulted in 12% mean body weight loss 10 days after dosing initiation. One mouse in this group lost 20% body weight and was removed from study. All other mice in that group recovered any lost body weight after the last dose.

TABLE 11

Efficacy of Compound IIa administered on a q4d × 3 dose schedule in the subcutaneous KMS-11-luc tumor xenograft model

| Compound | Dose, route, schedule | Tumor response ||| Host response |||
|---|---|---|---|---|---|---|---|
| | | T/C, Day 31 (%) | Max. % Regression (Day) | Δ Tumor volume, Day 31 ($mm^3$) | Max. Δ body weight (Day) (g) | Max. Δ body weight (Day) (%) | Survival (alive/total) |
| Vehicle (20% Captisol) | Q4d × 3, i.v. | 100 | — | 2150 ± 191 | 0.31 ± 0.33 (D10) | 1.74 ± 1.37 (D10) | 9/9 |
| COMPOUND IIa | 0.25 mg/kg, Q4d × 3, i.v | 25 | 24 (D7) | 527 ± 152 | −1.4 ± 1.2, (D10) | −6.68 ± 1.67 (D10) | 9/9 |
| COMPOUND IIa | 0.5 mg/kg, Q4d × 3, i.v | 10 | 42 (D10) | 221 ± 71 | −0.94 ± 0.3 (D10) | −4.58 ± 1.67 (D10) | 9/9 |
| COMPOUND IIa | 1 mg/kg, Q4d × 3, i.v | 0.1* | 56 (D17) | 1.5 ± 26 | −2.76 ± 0.65 (D10) | −12.69 ± 5.0 (D10) | 8/9 |
| SB-715992 | 7.5 mg/kg, Q4d × 3, i.v. | —* | 49, (D14) | −46 ± 19 | −0.96 ± 0.31 (D10) | −4.8 ± 1.93 (D10) | 9/9 |
| Paclitaxel | 30 mg/kg, Q4d × 3, i.p. | 30 | 5 (D3) | 640 ± 190 | −0.63 ± 0.22 (D3) | −2.95 ± 1.0 (D10) | 9/9 | paralysis due to disease burden, the main end point for when to humanely euthanize mice. The day of euthanasia for each mouse was recorded, and the remaining percentage of mice surviving was plotted over time (Kaplan-Meier survival analysis). P values were calculated using the log-rank test (GraphPad Prism 4.0 software) to assess differences between treated and control groups (p<0.05 was considered significant). Body weights were measured twice weekly, and clinical observations were recorded daily. Body weights were captured and stored by StudyDirector software (StudyLog, South San Francisco, Calif.). Data analysis was as described above.

Results, Subcutaneous KMS-11-luc Tumor Xenograft Model: The efficacy study in the subcutaneous tumor model evaluated the activity of a range of doses of compound IIa administered on the q4d×3 schedule, with a high dose of 1 mg/mg, which is approximately half of its highest tolerated dose in SCID-Bg mice. Compound IIa activity was compared to SB-715992 (ispinesib, a KSP inhibitor by Cytokinetics that is in clinical trials) at half its highest tolerated dose of 7.5 mg/kg, and paclitaxel at its highest tolerated dose of 30 mg/kg q4d×3. The results are shown in Table 11. Tumor regression was observed to varying extents in all treatment groups during the dosing interval; however, tumor growth resumed after the completion of dosing. Tumor regrowth began earlier, and proceeded more rapidly, in mice treated with lower doses of compound IIa. By 8 days after the end of treatment, tumor re-growth was observed in the groups treated with paclitaxel and 0.25 mg/kg compound IIa. By 13 days post-treatment, tumor re-growth was observed in the group treated with 0.5 mg/kg of compound IIa. Doses of 1 mg/kg compound IIa and Results of disseminated KMS-11-luc Tumor Model: Drug treatment was initiated 10 days after cell implant. Bioluminescence imaging showed increased signal over time in the vehicle-treated group, suggesting localization in extra-skeletal regions, including lung, liver, and spleen. However, the predominant bioluminescence signal appeared to be skeletal, with multiple sources of signal, including long bones, skull, tooth root/mandible, pelvis and spine, in the majority of mice. Histological analyses of femurs collected from previous studies with this model have confirmed myeloma cell infiltration into bone marrow (Xin, et al 2006 Clin. Cancer Res. August 15; 12(16):4908-15.). Disease progression led primarily to hind limb paralysis with occasional significant body weight loss due to tumor burden, at which time mice were humanely euthanized. This was termed "conditional survival."

The results are shown in Table 12. The 0.5 and 1 mg/kg doses of compound IIa administered q4d×3 significantly reduced bioluminescence signal, a measure of overall disease burden, however, the 0.25 mg/kg treated group was not statistically different from the vehicle treated group. The 47% percent regression of signal on day 13 of mice treated with the 1 mg/kg dose was accompanied by >20% body weight loss by day 13 in one mouse in this group. All other animals in that group tolerated this dose. At the lower doses, compound IIa was well tolerated.

This dose dependent inhibition of disease burden, as measured by bioluminescence, resulted in a similar delay in hind limb paralysis and thus enhanced conditional survival of the mice compared with the vehicle-treated cohort in all groups. The median survival in the vehicle-treated group was 19 days, whereas that of the 0.25, 0.5 and 1 mg/kg compound IIa-treated group was 29, 35 and 52 days, respectively.

TABLE 12

Efficacy of Compound IIa administered on a q4d × 3 dose schedule in the KMS-11-luc disseminated disease model

| Compound | Dose, route, schedule | Tumor response | | | | Host response | |
|---|---|---|---|---|---|---|---|
| | | T/C, Day 13 (%) | Regression, Day 13 (%) | Δ Tumor Bioluminescence, Day 13 (photons/sec) | Mean Day of Survival | Max. Δ body weight (Day) (g) | Max. Δ body weight (Day) (%) |
| Vehicle (20% Captisol) | q4d × 3, i.v. | 100 | — | $1.5 \times 10^8 \pm 1.8 \times 10^7$ | 19** | 1.3 ± 0.19 (D14) | 5.9 ± 1.04 (D14) |
| COMPOUND IIa | 0.25 mg/kg, q4d × 3, i.v. | 15 | — | $2.2 \times 10^7 \pm 1.1 \times 10^6$ | 29** | 2.1 ± 1.23 (D14) | 5.0 ± 2.0 (D14) |
| COMPOUND IIa | 0.5 mg/kg, q4d × 3, i.v. | 0.7* | — | $1.1 \times 10^6 \pm 5.8 \times 10^5$ | 35** | 2.5 ± 0.23 (D14) | 6.7 ± 1.1 (D14) |
| COMPOUND IIa | 1 mg/kg, q4d × 3, i.v. | —* | 47 | $-4.3 \times 10^5 \pm 1.7 \times 10^5$ | 52** | -0.74 ± 0.75 (D13) | -3.3 ± 4.0 (D13) |

Example 12

Compounds of Formula II are Effective Against Drug-Resistant Tumors

Preclinical in vivo experiments have shown that compounds of Formula II are unexpectedly superior to structurally similar compounds that do not have a hydroxyl group or hydroxyl prodrug group in the acyl moiety. Tumor models that express an efflux pump, the plasma membrane P-glycoprotein (P-gp), were tested for sensitivity to compounds of Formula II and other drugs, including structurally similar compounds lacking the hydroxyl group (or acyloxy group) that is present in compounds of Formula II. P-gp is one mechanism of tumor resistance and perhaps the best understood and most classic example of an efflux resistance mechanism. The KB8.5 human cervical carcinoma subcutaneous xenograft model in mice was selected for pharmacological screening and subsequent selection and evaluation of these compounds; it corresponds to the KB3.1 cell line and differs only by having the efflux pump. The compounds of Formula II were compared to other KSP inhibitors as well as to paclitaxel, which is known to be affected by P-gp. The study described herein demonstrates that compounds of Formula II (e.g., Compounds IIa and IIc) are efficacious in vivo against a tumor that expresses P-gp and is resistant to other drugs, while a similar compound of Formula I lacking the hydroxyl group was not active against this tumor.

Materials

TABLE 1

Animal characteristics

| Species | Strain | Vendor | Gender | Weight | Age |
|---|---|---|---|---|---|
| Mouse (*Mus musculus*) | nu/nu | Charles River, Hollister, CA | female | 25 g | 6-8 weeks |

Experiments were performed using outbred athymic nu/nu mice (Charles River Laboratories) approximately 6-8 weeks old. Upon arrival, animals received a subcutaneous microchip implant (AVID, Folsom, La.) in the subscapular region for identification of individuals. Animals were allowed to acclimatize for 1 week before any experimental procedures began.

Maintenance Conditions

Mice were housed 4-5 animals per cage in clear polycarbonate micro-isolator cages with a 12-hour light, 12-hour dark cycle at temperatures between 70-80 degrees Fahrenheit and 30-70% relative humidity. Food (Purina rodent chow pellets) and water were provided ad libitum.

Experimental Conditions

The KB8.5 cells were grown in DMEM with 2 mM L-glutamine (Mediatech Inc., catalog #10-013-CV) supplemented with 10% fetal bovine serum (JRH Biosciences, catalog #12003-100 M). Once KB8.5 cells demonstrated a good growth rate, 10 ng/ml colchicine was added to maintain P-gp expression levels.

These cells were grown as adherent cultures, maintained at 37° C. in a humidified atmosphere containing 5% carbon dioxide. Cells were cultured for fewer than 10 passages prior to use. Cells were harvested at 95% confluency, and centrifuged at ~800×g for 5 minutes at 4° C. and then resuspended in a 1:1 ratio of HBSS (Mediatech Inc., catalog #21-021-CV) plus Matrigel™ at a concentration of 25 million cells/mL for the KB8.5 line for implantation subcutaneously (injection volume of 0.2 mL).

Compounds and Formulations

Compound IIa, compound IIc, compound IIa (shown below), and SB-715992 were formulated in a Captisol®-based formulation. Doses were administered intravenously (i.v.) and adjusted to each animal's body weight. Formulations were made once at the beginning of study and stored at room temperature. Clinical grade paclitaxel was purchased pre-mixed in a cremophor-based vehicle (Mayne Pharma, now Hospira, Lake Forest, Ill., catalog #NDC-6170334209) and diluted in sterile saline to provide a dose volume of 16 mL/kg for a 30 mg/kg dose administered intraperitoneally (i.p.)

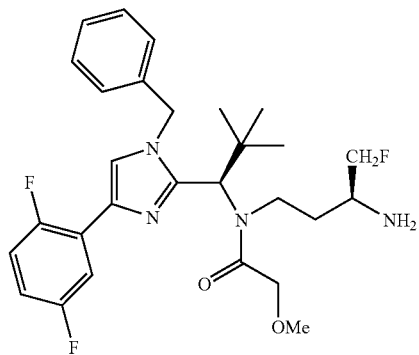

Ia

Compound IIa is structurally similar to compounds of formula II, but has a methoxy group rather than a hydroxy group or acyloxy group, and its in vitro activity against KSP is very similar to the activities of compounds IIa and IIc. For example, in the CellTiter-Glo® assay the GI50 value measured for compound Ia on HCT-15 cells was 0.3 nM, which is equivalent to compound IIa (see Example 2). Similarly, a value of 0.4 nM for the KB3.1 and KB8.5 cell lines was measured for compound Ia while values of 0.6 nM and 0.5 nM were measured for compound IIa on these same lines (see Example 2). However, the compounds of formula II have a free hydroxyl on the acyl group (or an acyloxy group that is a prodrug for a free hydroxyl), while Ia has a methyl ether instead. The methyl ether is well tolerated by the active site, as demonstrated by its activity in vitro, and in particular is also very effective on the p-GP resistant cell lines in vitro. In addition, it could be expected to be less susceptible to metabolic inactivation than the compounds of formula II in vivo. Indeed, as the data in the following Table illustrates, comparison of the pharmacokinetic parameters show that Compound Ia exhibits higher exposure and increased metabolic stability in vivo as compounds of Formula IIa and IIc. Surprisingly, though, compounds of formula II are advantageous in vivo relative to compounds known in the prior art against cancers expressing P-gp, since the P-gp resistant xenograft cancer was sensitive to compounds of Formula II but not to Compound Ia.

Interestingly, it was also found that the compounds of Formula II are significantly more efficacious than compounds lacking the hydroxyl entirely, e.g., a compound of Formula Ib:

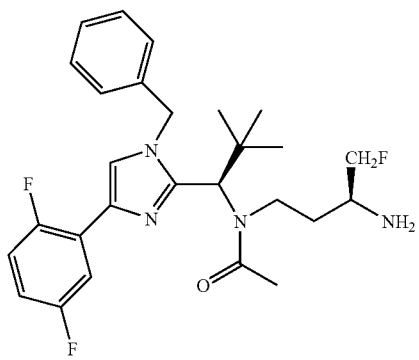

Ib

Compound Ib is much less active in vitro than the compounds of Formula II, having an IC-50 of 22 nm, compared to compounds IIa and IIc, which each have an IC-50 less than 1 nm. Compound Ib was not tested in the xenograft model, because its pharmacokinetics and its in vitro activity were too unfavorable to expect in vivo efficacy. It had been shown to have much lower in vivo availability based on data showing it exhibited a higher clearance rate and lower AUC ("Area under the curve", a standard way of measuring the in vivo exposure of a test subject to a compound), and it was also much less active at the target site as shown by its higher IC-50. By comparison, compounds Ia, IIa and IIc each exhibited better pharmacokinetic effects in vivo, as well as superior in vitro activity, and were tested in the xenograft cancer.

| Compound | In vitro activity (IC-50 - nm) | In vivo Clearance rate (mL/min/kg) | Half-Life in vivo (min) | AUC (ng-min/mL) |
|---|---|---|---|---|
| Ia | 0.6 | 29 | 117 | 160,000 |
| Ib | 22 | 94 | 90 | 52,000 |
| IIa | 0.8 | 41 | 110 | 116,000 |
| IIc | 0.9 | 47 | 110 | 102,000 |

Thus the compounds of Formula II are more effective in vitro and are more persistent in vivo than Compound Ib, and were unexpectedly shown to be effective on drug-resistant cancers expressing a multi-drug resistance (MDR) efflux pump, while Compound Ia was ineffective against the same MDR cancer in spite of its equal potency on the p-GP cell lines in vitro and higher availability in the test animal (lower clearance rate and higher AUC).

Study Methods

For the efficacy studies, mice were enrolled with a mean tumor volume of approximately 300 mm$^3$. Tumor xenografts were measured in two dimensions (L and W) with digital calipers twice weekly from the start of dosing on Day 0. Tumor volume was calculated as $(L \times W^2)/2$. Body weights were measured twice weekly and clinical observations were recorded daily. Tumor volume and body weights were captured and stored by StudyDirector software (StudyLog, South San Francisco, Calif.).

Data Analysis

Percent treatment/control (ΔT/ΔC) values for tumor volumes were calculated using the following formula:

$$\% \Delta T/\Delta C = 100 \times \Delta T/\Delta C$$

where:

T=mean tumor volume of the drug-treated group on the final day of the study;

ΔT=mean tumor volume of the drug-treated group on the final day of the study−mean tumor volume of the drug-treated group on initial day of dosing;

C=mean tumor volume of the control group on the final day of the study; and

ΔC=mean tumor volume of the control group on the final day of the study−mean tumor volume of the control group on initial day of dosing.

All data were expressed as mean and SEM. Between-groups comparisons for final tumor measurements were performed using the one-way ANOVA pair-wise analysis. Significance was determined using Kruskal-Wallis one-way ANOVA on Ranks, followed by appropriate post-hoc test (Dunn's Method or Tukey Test) for multiple pair-wise comparisons. Statistical analysis was carried out using SigmaStat (Systat Software Inc., San Jose, Calif.).

Efficacy Assessments in P-gp Expressing Xenograft Models

Figure 3A:
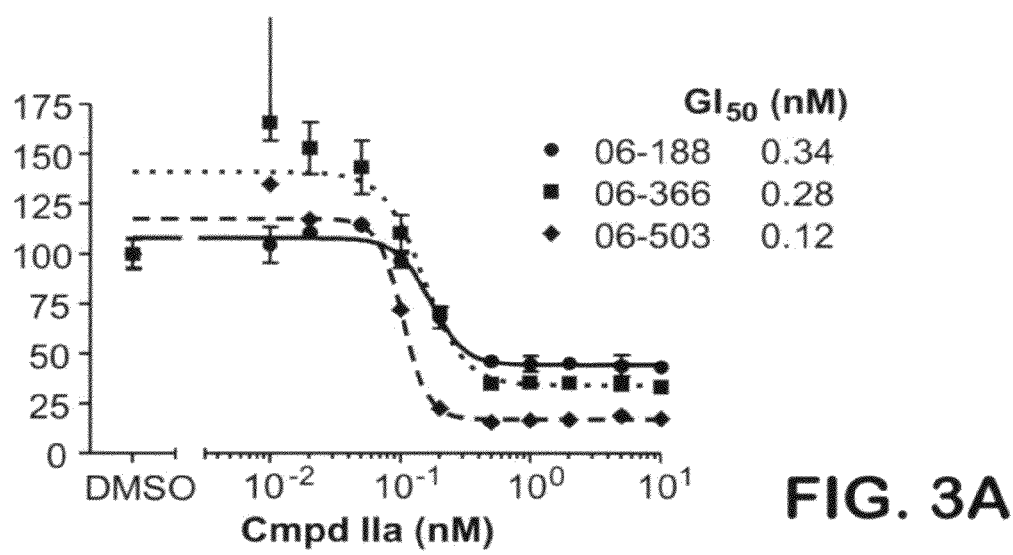
FIG. 3. Data showing that Compound IIa is cytotoxic to AML blast cells from AML patients. Panel A shows % Survival as a function of dosage. Panel B shows cell cultures after 2 weeks growth time. Panel C shows the percent of cells in <2N, 2N or 4N stage, comparing the effect of Compound IIa with that of paclitaxel.
Figure 3B:
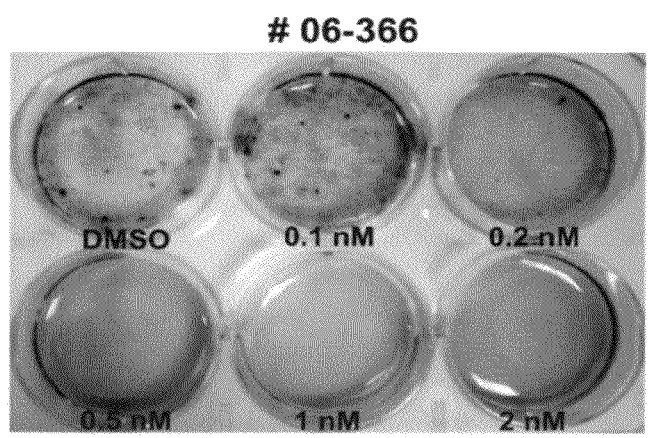
Figure 3C:
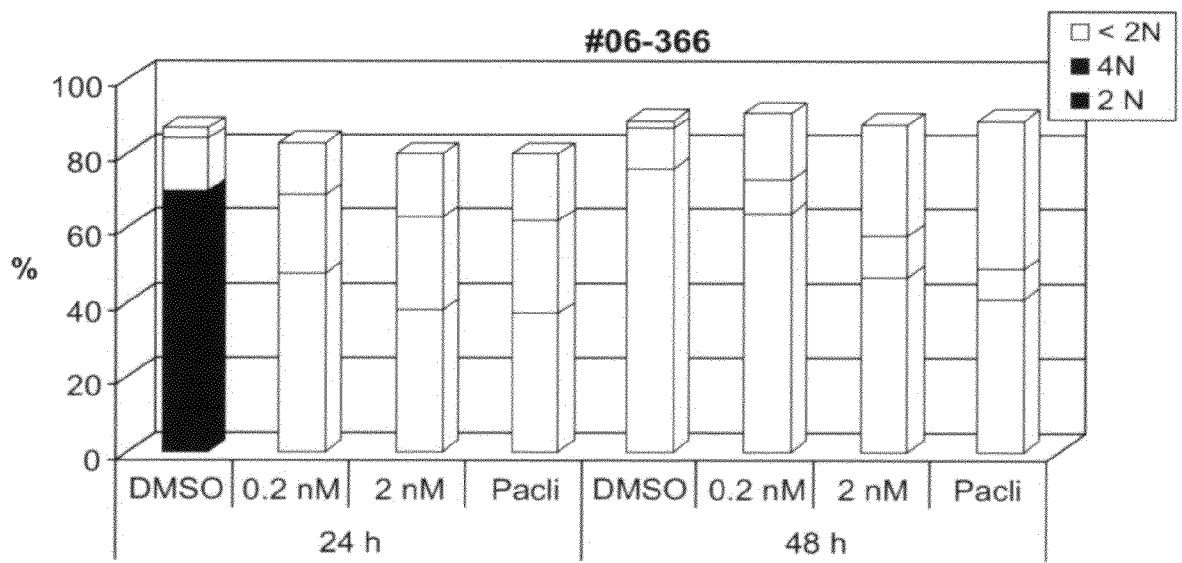

Multi-dose efficacy studies at the same 5 mg/kg dose on a q4d×3 schedule were conducted in these models, comparing activity of Compound IIa and Compound Ia. For the compound IIc, 2.5 mg/kg was not well tolerated, and so the efficacy comparison was to the dose level of 1.25 mg/kg. The results in FIG. 3 and Table 13 indicate that Compound IIa demonstrates significant anti-tumor efficacy in the model, with a percent ΔT/ΔC of 19% (p<0.05) in the KB8.5 xenograft model at day 11.

TABLE 13

Efficacy of Compound IIa administered on a q4d × 3 dose schedule in the KB8.5 tumor xenograft model.

| Compound | Dose, route, schedule | Tumor response ΔT/ΔC, Day 11 (%) | Host response % Max. Δ body weight, (Day) | Survival (alive/total) |
|---|---|---|---|---|
| Vehicle | i.v., q4d × 3 | 100 | 6 (D7) | 9/9 |
| Compound IIa | 5 mg/kg, i.v., q4d × 3 | 19* | −2 (D11) | 9/9 |
| SB-715992 | 15 mg/kg, i.v., q4d × 3 | 56 | 4 (D7) | 9/9 |
| Paclitaxel | 30 mg/kg, i.p., q4d × 3 | 78 | 5 (D11) | 9/9 |

KB8.5 cells were established in female nu/nu mice (Charles River) by subcutaneous injection of $5 \times 10^6$ cells in 0.2 mL of a 1:1 ratio of HBSS plus Matrigel ™ into the right flank of the mice. When tumors reached approximately 300 mm³, mice were randomized based on tumor volumes into treatment groups (n = 9). Compounds were administered at the dose levels and schedules indicated. The effect of the treatment on tumor volumes and body weights are presented as means ± SEM. The experiment was evaluated on treatment day 11.
*p < 0.05 versus vehicle and SB-715992 (Kruskal-Wallis One Way ANOVA on Ranks/Dunn's Method).

Figures 4A, 4B:
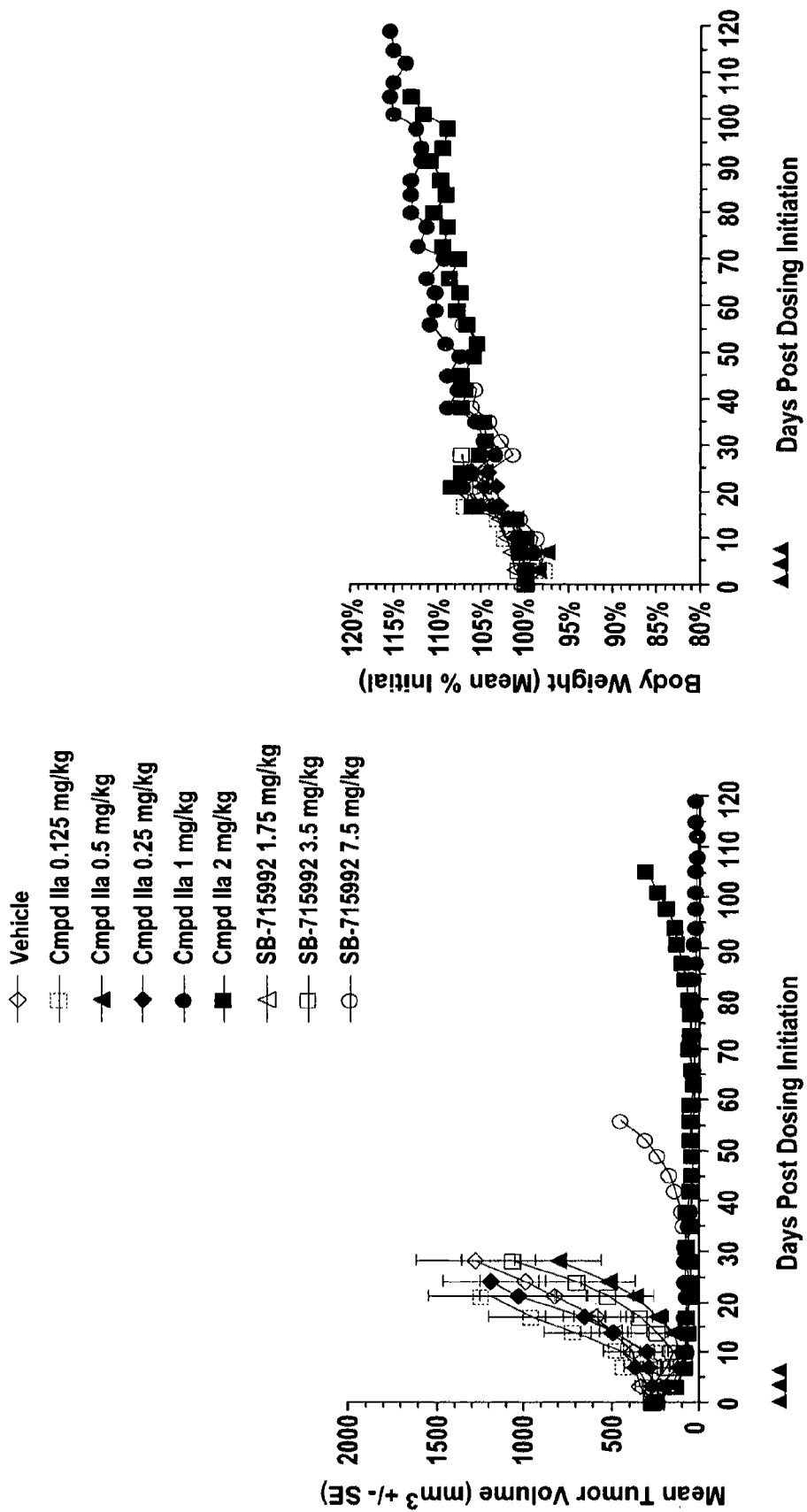
FIG. 4. Efficacy of compound IIa administered on a q4d×3 dose schedule in the MV4; 11 subcutaneous tumor xenograft model. MV4; 11 tumors were established in female athymic nu/nu mice by subcutaneous injection of $10^7$ cells in 0.2 mL of a 1:1 ratio of HBSS and Matrigel™ into the right flank of each mouse. When tumors reached 250 mm$^3$, approximately 24 days after cell implantation, mice were randomized according to tumor volume into treatment groups (n=9). Animals were intravenously administered vehicle (Captisol®), compound IIa or SB-715992 (Ispinesib, a KSP inhibitor by Cytokinetics that is in clinical trials) i.v. All were dosed on a q4d×3 schedule. (A) Efficacy/tumor volumes of treatment groups vs. days post randomization; (B) Percent body weight change relative to initial weights on day of randomization.

Likewise, the results in FIG. 4 and Table 14 indicate that Compound IIc demonstrates significant anti-tumor efficacy in this model, with a percent ΔT/ΔC of 39% (p<0.05) at day 11.

TABLE 14

Efficacy of Compound IIc administered on a q4d × 3 dose schedule in the KB8.5 tumor xenograft model.

| Compound | Dose, route, schedule | Tumor response ΔT/ΔC, Day 11 (%) | Host response % Max. Δ body weight, (Day) | Survival (alive/total) |
|---|---|---|---|---|
| Vehicle | i.v., q4d × 3 | 100 | +8 (D11) | 9/9 |
| Cmpd IIc | 1.25 mg/kg, i.v., q4d × 3 | 39* | −5 (D11) | 9/9 |
| Cmpd IIc | 2.5 mg/kg, i.v., q4d × 3 | Not applicable | −10 (D8) | All down on Day 8 due to 4/9 mice having 15% weight loss or more |
| SB-715992 | 15 mg/kg, i.v., q4d × 3 | 77 | −1 (D4) | 9/9 |
| Paclitaxel | 30 mg/kg, i.p., q4d × 3 | 87 | +3 (D11) | 9/9 |

KB8.5 cells were established in female nu/nu mice (Charles River) by subcutaneous injection of $5 \times 10^6$ cells in 0.2 mL of a 1:1 ratio of HBSS plus Matrigel ™ into the right flank of the mice. When tumors reached an average of 339 mm³, mice were randomized based on tumor volumes into treatment groups (n = 9). Compounds were administered at the dose levels and schedules indicated. The effect of the treatment on tumor volumes and body weights are presented as means ± SEM. The experiment was evaluated on treatment day 11.
*p < 0.05 versus vehicle (Kruskal-Wallis One Way ANOVA on Ranks/Tukey's Test).

Figures 5A, 5B:
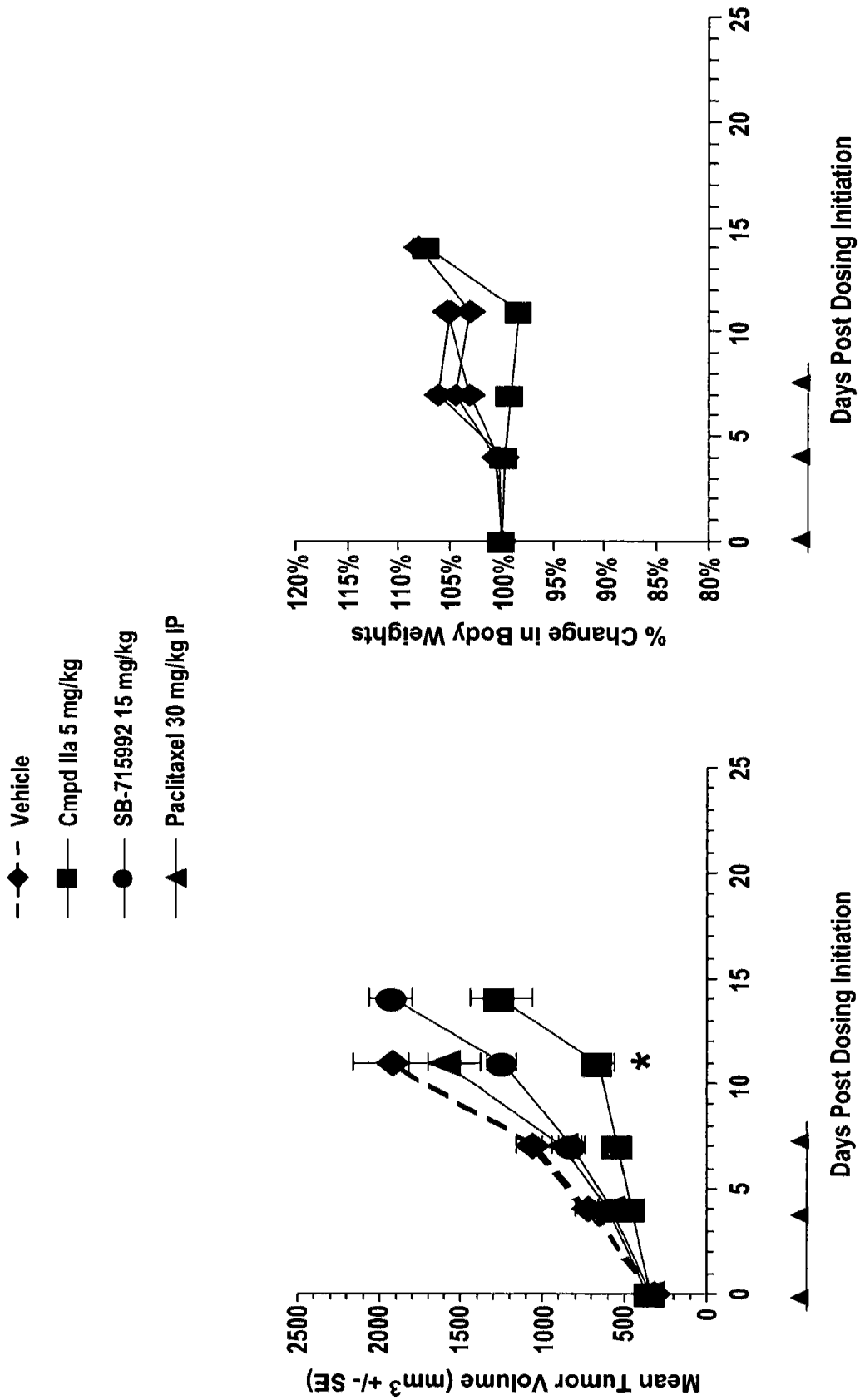
FIG. 5. Efficacy of compound IIa administered on a q4d×3 dose schedule in the KB8.5 tumor xenograft model. KB8.5 tumors were established in female athymic nu/nu mice (Charles River Laboratories) by subcutaneous injection of 5×10$^6$ cells in 0.2 mL of 1:1 ratio of HBSS and Matrigel™ into the right flank of each mouse. When tumors reached approximately 300 mm$^3$, approximately 10 days after cell implantation, mice were randomized according to tumor volume into treatment groups (n=9/group). Animals were i.v. administered Compound IIa or SB-715992. Paclitaxel was administered at 30 mg/kg i.p. All were dosed on a q4d×3 schedule. (Left) Efficacy/tumor volumes of treatment groups vs. days post dosing initiation; (Right) Percent body weight change relative to initial weights on day of randomization/dosing initiation. *$p<0.05$ compared with vehicle and SB-715992 (ANOVA/Dunn's Method).

In contrast, the similar compound lacking a hydroxyl on the acyl moiety and having a methoxy instead, Compound Ia, was not efficacious in the KB8.5 tumor xenograft model, as shown in FIG. 5 and Table 15.

TABLE 15

Efficacy of Compound Ia administered on a q4d × 3 dose schedule in the KB8.5 tumor xenograft model.

| Compound | Dose, route, schedule | Tumor response ΔT/ΔC, Day 11 (%) | Host response % Max. Δ body weight, (Day) | Survival (alive/total) |
|---|---|---|---|---|
| Vehicle | i.v., q4d × 3 | 100 | 4 (D11) | 10/10 |
| Cmpd Ia | 1.25 mg/kg, i.v., q4d × 3 | 84 | 1 (D11) | 10/10 |
| Cmpd Ia | 2.5 mg/kg, i.v., q4d × 3 | 61 | −0.4 (D4) | 10/10 |
| Cmpd Ia | 5 mg/kg, iv, q4d × 3 | 66 | −2 (D4) | 10/10 |
| SB-715992 | 15 mg/kg, i.v., q4d × 3 | 60 | −3 (D11) | 10/10 |

TABLE 15-continued

Efficacy of Compound Ia administered on a q4d × 3 dose schedule in the KB8.5 tumor xenograft model.

| | | Tumor response | Host response | |
|---|---|---|---|---|
| Compound | Dose, route, schedule | ΔT/ΔC, Day 11 (%) | % Max. Δ body weight, (Day) | Survival (alive/total) |
| Paclitaxel | 30 mg/kg, i.p., q4d × 3 | 60 | −2 (D4) | 10/10 |

KB8.5 cells were established in female nu/nu mice (Charles River) by subcutaneous injection of 5 × 10$^6$ cells in 0.2 mL of a 1:1 ratio of HBSS plus Matrigel ™ into the right flank of the mice. When tumors reached an average of 285 mm$^3$, mice were randomized based on tumor volumes into treatment groups (n = 10). Compounds were administered at the dose levels and schedules indicated. The effect of the treatment on tumor volumes and body weights are presented as means ± SEM. The experiment was evaluated on treatment day 11.
No groups were statistically different from vehicle group (Kruskal-Wallis One Way ANOVA on Ranks).

No significant body weight loss or outward signs of toxicity were observed in any of the treated mice, except for significant weight loss in the 2.5 mg/kg Compound IIc treated group. The increased antitumor activity seen in the P-gp positive KB8.5 model demonstrates an unexpected advantage of compounds of Formula II over a similar compound of Formula I lacking the hydroxyl functionality that characterizes the compounds of Formula II.

Example 13

Compounds of Formula II are Effective Against Many Tumor Explants

Compound IIa was tested against a panel of cell lines and tumor explants in a soft agar assay as described in Fiebig, H. H., Maier, A., and Burger, A. M. (*Clonogenic assay with established human tumour xenorafts: correlation of in vitro to in vivo activity as a basis for anticancer drug discovery*, Eur. J. Cancer 40, 802-820 (2004).) Table 16 lists the type of cancer, the name of the sample, its GI$_{50}$ (concentration needed to achieve 50% growth inhibition) value in the assay, the logarithm of the GI$_{50}$ (log(GI$_{50}$)), and the relative sensitivity of each sample (Differential). The differential is calculated by subtracting the log(GI$_{50}$) for each cell line from the average log(GI$_{50}$) across the entire panel (0.236 in this case); a positive value indicates a sample that is more sensitive than average, whereas a negative value indicates a sample that is less sensitive than average.

Most indications have samples that are sensitive. The most sensitive cancers based on this assay are: hematological cancers (leukemia and lymphoma, 5/5), small cell lung cancer (SCLC; 5/5), breast (7/10), bladder (4/6) and sarcomas (4/7).

TABLE 16

Activity of Compound IIa in various cancer cell lines.

| Cancer type | Tumor sample | GI$_{50}$ (nM) | log(GI$_{50}$) | Differential |
|---|---|---|---|---|
| Leukemia (ALL) | CCRFCEM | 0.287 | −0.542 | 0.779 |
| Leukemia (ALL) | JURKAT | 0.106 | −0.975 | 1.211 |
| Leukemia (CML) | K562 | 0.27 | −0.569 | 0.805 |
| Leukemia (ALL) | MOLT4 | 0.877 | −0.057 | 0.293 |
| Lymphoma (NHL) | U937 | 0.086 | −1.066 | 1.302 |
| NSCLC | 1012 | 0.926 | −0.033 | 0.270 |
| NSCLC | 289 | 4.899 | 0.690 | −0.454 |
| NSCLC | 526 | 1.265 | 0.102 | 0.134 |
| NSCLC | 629 | 10 | 1.000 | −0.764 |
| NSCLC | 677 | 1.162 | 0.065 | 0.171 |
| NSCLC | 737 | 3.068 | 0.487 | −0.250 |
| NSCLC | 1422 | 0.728 | −0.138 | 0.374 |
| NSCLC | 211 | 0.216 | −0.666 | 0.902 |
| NSCLC | 1176 | 3 | 0.477 | −0.241 |
| NSCLC | 1647 | 16.752 | 1.224 | −0.988 |
| SCLC | 538 | 0.339 | −0.470 | 0.706 |
| SCLC | 573 | 0.587 | −0.231 | 0.468 |
| SCLC | 615 | 0.082 | −1.086 | 1.323 |
| SCLC | 650 | 0.376 | −0.425 | 0.661 |
| SCLC | H69 | 0.269 | −0.570 | 0.807 |
| Colorectal | 1034 | 0.214 | −0.670 | 0.906 |
| Colorectal | 1044 | 0.612 | −0.213 | 0.450 |
| Colorectal | 1103 | 1 | 0.000 | 0.236 |
| Colorectal | 1299 | 10 | 1.000 | −0.764 |
| Colorectal | 1297 | 10 | 1.000 | −0.764 |
| Colorectal | 158 | 10 | 1.000 | −0.764 |
| Colorectal | 1729 | 10 | 1.000 | −0.764 |
| Colorectal | 1753 | 11.279 | 1.052 | −0.816 |
| Colorectal | 1788 | 2.246 | 0.351 | −0.115 |
| Colorectal | 1783 | 0.721 | −0.142 | 0.378 |
| Colorectal | 1784 | 5.969 | 0.776 | −0.539 |
| Colorectal | 233 | 0.238 | −0.623 | 0.860 |
| Colorectal | 243 | 10 | 1.000 | −0.764 |
| Colorectal | 260 | 10 | 1.000 | −0.764 |
| Colorectal | 268 | 6.24 | 0.795 | −0.559 |
| Colorectal | 280 | 10 | 1.000 | −0.764 |
| Colorectal | 504 | 0.273 | −0.564 | 0.800 |
| Colorectal | 533 | 1.753 | 0.244 | −0.007 |
| Colorectal | 609 | 10 | 1.000 | −0.764 |
| Colorectal | 647 | 10 | 1.000 | −0.764 |
| Colorectal | 676 | 10 | 1.000 | −0.764 |
| Colorectal | 742 | 1.873 | 0.273 | −0.036 |
| Colorectal | 94LX | 19.52 | 1.290 | −1.054 |
| Colorectal | 975 | 10 | 1.000 | −0.764 |
| Melanoma | 1341 | 10 | 1.000 | −0.764 |
| Melanoma | 462 | 10 | 1.000 | −0.764 |
| Melanoma | 989 | 12.722 | 1.105 | −0.868 |
| Ovarian | 1353 | 10 | 1.000 | −0.764 |
| Ovarian | 899 | 10.000 | 1.000 | −0.764 |
| Prostate | 22RV1 | 0.537 | −0.270 | 0.506 |
| Prostate | DU145 | 1 | 0.000 | 0.236 |
| Prostate | MRIH1579 | 10 | 1.000 | −0.764 |
| Prostate | PC3M | 0.424 | −0.373 | 0.609 |
| Breast | 1162 | 0.286 | −0.544 | 0.780 |
| Breast | 1322 | 1.402 | 0.147 | 0.090 |
| Breast | 1384 | 2.666 | 0.426 | −0.189 |
| Breast | 1398 | 0.239 | −0.622 | 0.858 |
| Breast | 401 | 0.563 | −0.249 | 0.486 |
| Breast | 449 | 0.534 | −0.272 | 0.509 |
| Breast | 574 | 10 | 1.000 | −0.764 |
| Breast | 583 | 0.239 | −0.622 | 0.858 |
| Breast | 713 | 0.244 | −0.613 | 0.849 |
| Breast | 857 | 2.456 | 0.390 | −0.154 |
| Bladder | 1036 | 0.115 | −0.939 | 1.176 |
| Bladder | 1218 | 0.509 | −0.293 | 0.530 |
| Bladder | 1228 | 0.315 | −0.502 | 0.738 |
| Bladder | 1258 | 17.076 | 1.232 | −0.996 |

TABLE 16-continued

Activity of Compound IIa in various cancer cell lines.

| Cancer type | Tumor sample | GI$_{50}$ (nM) | log(GI$_{50}$) | Differential |
|---|---|---|---|---|
| Bladder | 1352 | 0.972 | −0.012 | 0.249 |
| Bladder | 439 | 10 | 1.000 | −0.764 |
| Gastric | 1172 | 10 | 1.000 | −0.764 |
| Gastric | 209 | 10 | 1.000 | −0.764 |
| Gastric | 214 | 9 | 0.954 | −0.718 |
| Sarcoma | 117 | 0.249 | −0.604 | 0.840 |
| Sarcoma | 1186 | 0.327 | −0.485 | 0.722 |
| Sarcoma | 1301 | 0.235 | −0.629 | 0.865 |
| Sarcoma | 1410 | 2.246 | 0.351 | −0.115 |
| Sarcoma | 417 | 0.16 | −0.796 | 1.032 |
| Sarcoma | 463 | 19.122 | 1.282 | −1.045 |
| Sarcoma | 627 | 10 | 1.000 | −0.764 |
| Pancreas | 1657 | 26.952 | 1.431 | −1.194 |
| Pancreas | 1861 | 0.623 | −0.206 | 0.442 |
| Pancreas | 1869 | 10.865 | 1.036 | −0.800 |
| Pancreas | 1876 | 0.337 | −0.472 | 0.709 |
| Pancreas | 1872 | 0.282 | −0.550 | 0.786 |
| Pancreas | 1881 | 2.316 | 0.365 | −0.128 |
| Pancreas | 1887 | 10 | 1.000 | −0.764 |
| Pancreas | 1900 | 16.933 | 1.229 | −0.992 |
| Pancreas | 1912 | 0.112 | −0.951 | 1.187 |
| Pancreas | 1937 | 0.185 | −0.733 | 0.969 |
| Pancreas | 546 | 2.591 | 0.413 | −0.177 |
| Pancreas | 736 | 1.265 | 0.102 | 0.134 |
| Mean | | 1.724 | 0.236 | |

Example 14

Compounds of Formula II are Effective Against Many Solid Tumor Cell Lines

Compound IIa was tested against a panel of cell lines derived from solid tumors as described in See also McDermott, U., Sharma, S. V., Dowell, L., Greninger, P., Montagut, C., Lamb, J., Archibald, H., Raudales, R., Tam, A., Lee, D., Rothenberg, S. M., Supko, J. G., Sordella, R., Ulkus, L. E., Iafrate, A. J., Maheswaran, S., Njauw, C. N., Tsao, H., Drew, L., Hanke, J. H., Ma, X. J., Erlander, M. G., Gray, N. S., Haber, D. A., and Settleman, J. (2007), *Identification of genotype-correlated sensitivity to selective kinase inhibitors by using high-throughput tumor cell line profiling.* Proc. Natl. Acad. Sci. U.S. A 104, 19936-19941 (2007).) Cells were treated with the compound for 72 hours and the fraction of surviving cells, as compared to an untreated control, was reported. Table 17 lists the name of the cell line, the organ of origin, the fraction of surviving cells at the three concentrations tested (0.2 nM, 2.0 nM and 20 nM) and a sensitivity score. The sensitivity score was from 5 (most sensitive) to 1 (least sensitive) and the scoring was as follows: 5=surviving fraction≦0.2 at 0.2 nM; 4=0.2<surviving fraction≦0.5 at 0.2 nM; 3=surviving fraction>0.5 at 0.2 nM and ≦0.5 at 2.0 nM; 2=surviving fraction>0.5 at 2.0 nM and ≦0.5 at 20 nM; 1=surviving fraction>0.5 at 20 nM.

All indications have samples that are sensitive. One of the many possible ways to rank order these cancers for sensitivity is to calculate the average sensitivity score for each indication (sum of sensitivity scores/number of samples). If one takes very stringent criteria using an average score of 3 or more, the most sensitive cancers based on this assay are: ovary (3.38), stomach (3.32), brain (3.21), skin (3.02), cervix (3.00), and thyroid (3.00).

TABLE 17

Activity of Compound IIa in various solid tumor cell lines.

| Cell Line | Organ | 0.2 nM | 2.0 nM | 20 nM | Sensitivity |
|---|---|---|---|---|---|
| SCaBER | Bladder | 0.6666 | 0.0383 | 0.0238 | 3 |
| 1A6 | Bladder | 0.9359 | 0.0473 | 0.0309 | 3 |
| RT112/84 | Bladder | 1.0884 | 0.0457 | 0.0312 | 3 |
| 5637 | Bladder | 1.1044 | 0.0595 | 0.0423 | 3 |
| EJ138 | Bladder | 1.1072 | 0.0888 | 0.0712 | 3 |
| RT-112 | Bladder | 0.925 | 0.099 | 0.0915 | 3 |
| SW 780 | Bladder | 0.7289 | 0.091 | 0.0981 | 3 |
| RT4 | Bladder | 0.5091 | 0.1175 | 0.1008 | 3 |
| T24 | Bladder | 0.723 | 0.131 | 0.102 | 3 |
| 647-V | Bladder | 0.721 | 0.185 | 0.141 | 3 |
| VM-CUB1 | Bladder | 0.8161 | 0.1594 | 0.1497 | 3 |
| SW-1710 | Bladder | 0.7185 | 0.1353 | 0.1546 | 3 |
| KU-19-19 | Bladder | 0.9247 | 0.1929 | 0.1985 | 3 |
| UM-UC-3 | Bladder | 0.9804 | 0.2219 | 0.2074 | 3 |
| BFTC-905 | Bladder | 1.089 | 0.264 | 0.223 | 3 |
| HT 1376 | Bladder | 1.1586 | 0.2837 | 0.233 | 3 |
| CAL-29 | Bladder | 0.967 | 0.282 | 0.256 | 3 |
| J82 | Bladder | 0.7211 | 0.3475 | 0.2914 | 3 |
| 639-V | Bladder | 0.961 | 0.37 | 0.31 | 3 |
| TCCSUP | Bladder | 1.0148 | 0.5876 | 0.4752 | 2 |
| HT-1197 | Bladder | 1.0133 | 0.9855 | 0.8308 | 1 |
| CSR1 | Bone | 0.2156 | 0.0818 | 0.0769 | 4 |
| CS1 | Bone | 0.4253 | 0.1844 | 0.1903 | 4 |
| Hs 888.T | Bone | 0.4945 | 0.4138 | 0.3803 | 4 |
| MHH-ES-1 | Bone | 0.687 | 0.032 | 0.017 | 3 |
| SK-ES-1 | Bone | 0.9862 | 0.0606 | 0.0516 | 3 |
| KHOS-240S | Bone | 0.925 | 0.071 | 0.065 | 3 |
| Saos-2 | Bone | 0.6146 | 0.118 | 0.1008 | 3 |
| HOS | Bone | 1.033 | 0.078 | 0.118 | 3 |
| RD-ES | Bone | 0.6036 | 0.2671 | 0.1397 | 3 |
| KHOS-312H | Bone | 1.103 | 0.284 | 0.231 | 3 |
| U-2 OS | Bone | 1.0283 | 0.241 | 0.2322 | 3 |
| NY | Bone | 1.293 | 0.341 | 0.3 | 3 |
| CAL-72 | Bone | 0.9276 | 0.3256 | 0.3065 | 3 |
| HuO-3N1 | Bone | 0.9177 | 0.3533 | 0.3165 | 3 |
| MG-63 | Bone | 0.815 | 0.57 | 0.502 | 1 |
| H-EMC-SS | Bone | 0.8996 | 0.604 | 0.5042 | 1 |
| MC-IXC | Brain | 0.079 | 0.047 | 0.033 | 5 |
| SK-N-SH | Brain | 0.1798 | 0.0495 | 0.0574 | 5 |
| NB69 | Brain | 0.0922 | 0.0639 | 0.0662 | 5 |
| Hs 683 | Brain | 0.4152 | 0.0858 | 0.0278 | 4 |
| SK-N-AS | Brain | 0.357 | 0.0895 | 0.0819 | 4 |
| M059J | Brain | 0.4307 | 0.1343 | 0.0874 | 4 |
| SH-SY5Y | Brain | 0.4428 | 0.1183 | 0.0946 | 4 |
| Daoy | Brain | 0.4727 | 0.0556 | 0.1088 | 4 |
| MOG-G-CCM | Brain | 0.2092 | 0.1363 | 0.1564 | 4 |
| YKG-1 | Brain | 0.3102 | 0.1764 | 0.1624 | 4 |
| CCF-STTG1 | Brain | 0.3804 | 0.3579 | 0.2861 | 4 |
| GOS-3 | Brain | 0.4488 | 0.3264 | 0.2977 | 4 |
| SK-N-MC | Brain | 0.5584 | −0.0017 | −0.0048 | 3 |
| U-251 MG | Brain | 0.8575 | 0.0313 | 0.0321 | 3 |
| BE(2)-C | Brain | 0.757 | 0.0224 | 0.033 | 3 |
| LNZTA3WT4 | Brain | 0.5274 | 0.0814 | 0.052 | 3 |
| LNZTA3WT11 | Brain | 0.6268 | 0.0841 | 0.0567 | 3 |
| T98G | Brain | 0.6311 | 0.0972 | 0.0718 | 3 |
| LN-229 | Brain | 0.7177 | 0.1241 | 0.0965 | 3 |
| MOG-G-UVW | Brain | 0.7682 | 0.1238 | 0.1114 | 3 |
| H4 | Brain | 0.5851 | 0.1689 | 0.12 | 3 |
| PFSK-1 | Brain | 0.5585 | 0.1428 | 0.1766 | 3 |
| SW 1783 | Brain | 0.7547 | 0.2518 | 0.1872 | 3 |
| SF-295 | Brain | 0.5622 | 0.2393 | 0.191 | 3 |
| DK-MG | Brain | 0.5941 | 0.228 | 0.1916 | 3 |
| A172 | Brain | 0.6374 | 0.22 | 0.1923 | 3 |
| GAMG | Brain | 1.2891 | 0.2385 | 0.1923 | 3 |
| 1321N1 | Brain | 0.7485 | 0.2015 | 0.1977 | 3 |
| CHP-212 | Brain | 0.946 | 0.267 | 0.216 | 3 |
| LN-18 | Brain | 0.9918 | 0.238 | 0.2181 | 3 |
| U-118 MG | Brain | 0.9433 | 0.2612 | 0.2391 | 3 |
| U373 MG | Brain | 0.5474 | 0.307 | 0.2442 | 3 |
| SW 1088 | Brain | 0.7941 | 0.242 | 0.2644 | 3 |
| DBTRG-05MG | Brain | 0.8442 | 0.387 | 0.2789 | 3 |
| KG-1-C | Brain | 0.9548 | 0.3391 | 0.3367 | 3 |
| SCCH-26 | Brain | 0.8806 | 0.351 | 0.3398 | 3 |
| 42-MG-BA | Brain | 0.9486 | 0.4389 | 0.3783 | 3 |
| SNB-19 | Brain | 1.0241 | 0.4679 | 0.4543 | 3 |
| IPTP/98 | Brain | 0.8158 | 0.3799 | 0.4603 | 3 |

TABLE 17-continued

Activity of Compound IIa in various solid tumor cell lines.

| Cell Line | Organ | 0.2 nM | 2.0 nM | 20 nM | Sensitivity |
|---|---|---|---|---|---|
| GMS-10 | Brain | 0.9262 | 0.6735 | 0.5424 | 1 |
| U-138 MG | Brain | 0.8028 | 0.4448 | 0.5689 | 1 |
| LN-405 | Brain | 1.046 | 0.6715 | 0.7525 | 1 |
| AU565 | Breast | 0.1024 | 0.0539 | 0.0297 | 5 |
| HCC1954 | Breast | 0.2453 | 0.0742 | 0.0831 | 4 |
| Hs 578T | Breast | 0.287 | 0.075 | 0.085 | 4 |
| CAL-85-1 | Breast | 0.2062 | 0.1707 | 0.1396 | 4 |
| EFM-192B | Breast | 0.3565 | 0.2746 | 0.1884 | 4 |
| EFM-19 | Breast | 0.4888 | 0.2428 | 0.2227 | 4 |
| HCC1143 | Breast | 0.3856 | 0.2969 | 0.2799 | 4 |
| MDA-MB-415 | Breast | 0.4378 | 0.2779 | 0.2826 | 4 |
| MB 157 | Breast | 0.919 | 0.03 | 0.013 | 3 |
| MDA-MB-468 | Breast | 0.826 | 0.131 | 0.104 | 3 |
| MCF7 | Breast | 0.7312 | 0.1175 | 0.106 | 3 |
| MDA-MB-453 | Breast | 0.9677 | 0.1497 | 0.128 | 3 |
| HCC1806 | Breast | 0.63 | 0.157 | 0.135 | 3 |
| HCC38 | Breast | 0.799 | 0.198 | 0.135 | 3 |
| CAL-148 | Breast | 0.8879 | 0.1778 | 0.1446 | 3 |
| MDA-MB-436 | Breast | 0.9257 | 0.235 | 0.1588 | 3 |
| EVSA-T | Breast | 0.8101 | 0.1921 | 0.1617 | 3 |
| JIMT-1 | Breast | 1.0342 | 0.2107 | 0.2045 | 3 |
| CAL-120 | Breast | 0.7606 | 0.3094 | 0.2346 | 3 |
| CAL-51 | Breast | 1.0399 | 0.252 | 0.2391 | 3 |
| HCC1569 | Breast | 0.8118 | 0.3757 | 0.2706 | 3 |
| MDA-MB-435S | Breast | 0.736 | 0.4 | 0.369 | 3 |
| KPL-1 | Breast | 0.8294 | 0.4721 | 0.3691 | 3 |
| HCC70 | Breast | 1.029 | 0.4525 | 0.3868 | 3 |
| MDA-MB-361 | Breast | 0.51 | 0.4185 | 0.4945 | 3 |
| EFM-192C | Breast | 1.1771 | 0.5303 | 0.2644 | 2 |
| MDA-MB-175-VII | Breast | 0.9252 | 0.6705 | 0.4413 | 2 |
| UACC-893 | Breast | 0.578 | 0.635 | 0.474 | 2 |
| BT-474 | Breast | 1.7649 | 0.4043 | 0.4842 | 2 |
| BT-549 | Breast | 0.7005 | 0.6093 | 0.5628 | 1 |
| T47D | Breast | 1.1392 | 0.657 | 0.6325 | 1 |
| ZR-75-30 | Breast | 0.979 | 0.7094 | 0.6879 | 1 |
| MT-3 | Breast | 0.8962 | 0.6827 | 0.704 | 1 |
| BT-483 | Breast | 0.8449 | 1.114 | 0.8657 | 1 |
| C-4 I | Cervix | 0.3791 | 0.0476 | 0.0328 | 4 |
| CAL-39 | Cervix | 0.3382 | 0.1481 | 0.1479 | 4 |
| C-33 A | Cervix | 0.916 | 0.0127 | −0.006 | 3 |
| SISO | Cervix | 0.7157 | 0.0163 | −0.002 | 3 |
| HeLa | Cervix | 0.7398 | 0.048 | 0.0072 | 3 |
| MS751 | Cervix | 0.6941 | 0.0256 | 0.0552 | 3 |
| BT-B | Cervix | 0.788 | 0.0821 | 0.0657 | 3 |
| ME-180 | Cervix | 0.9997 | 0.1521 | 0.1564 | 3 |
| Ca Ski | Cervix | 0.7077 | 0.2047 | 0.1791 | 3 |
| SKG-IIIb | Cervix | 0.718 | 0.2701 | 0.2185 | 3 |
| DoTc2 4510 | Cervix | 0.9503 | 0.2981 | 0.2597 | 3 |
| SW756 | Cervix | 0.9509 | 0.371 | 0.3384 | 3 |
| SiHa | Cervix | 0.5524 | 0.3919 | 0.3415 | 3 |
| C-4 II | Cervix | 0.8416 | 0.4293 | 0.4254 | 3 |
| HT-3 | Cervix | 0.8834 | 0.6888 | 0.6523 | 1 |
| KYSE-50 | Esophagus | 0.183 | 0.055 | 0.063 | 5 |
| KYSE-410 | Esophagus | 0.244 | 0.211 | 0.214 | 4 |
| T.Tn | Esophagus | 0.4246 | 0.3322 | 0.2448 | 4 |
| T.T | Esophagus | 0.8253 | 0.0649 | 0.0197 | 3 |
| KYSE-180 | Esophagus | 0.617 | 0.085 | 0.079 | 3 |
| TE7 | Esophagus | 0.718 | 0.113 | 0.113 | 3 |
| KYSE-510 | Esophagus | 0.671 | 0.223 | 0.129 | 3 |
| KYSE-70 | Esophagus | 0.824 | 0.201 | 0.158 | 3 |
| KYSE-150 | Esophagus | 1.166 | 0.213 | 0.163 | 3 |
| OE21 | Esophagus | 0.7539 | 0.2571 | 0.2117 | 3 |
| KYSE-520 | Esophagus | 1.111 | 0.386 | 0.356 | 3 |
| KYSE-30 | Esophagus | 0.7729 | 0.5353 | 0.4066 | 2 |
| KYSE-270 | Esophagus | 1.057 | 0.582 | 0.453 | 2 |
| KYSE-140 | Esophagus | 1.114 | 0.512 | 0.461 | 2 |
| HCE7 | Esophagus | 0.865 | 0.488 | 0.512 | 1 |
| COLO-680N | Esophagus | 0.882 | 0.535 | 0.515 | 1 |
| OE33 | Esophagus | 1.006 | 0.5977 | 0.5259 | 1 |
| KYSE-220 | Esophagus | 0.833 | 0.626 | 0.661 | 1 |
| OE19 | Esophagus | 0.9684 | 0.8451 | 0.6916 | 1 |
| JR 029 | Head & Neck | 0.0671 | 0.0015 | 0.0021 | 5 |
| PCI-38 | Head & Neck | 0.2035 | 0.0781 | 0.0682 | 4 |
| CAL 27 | Head & Neck | 0.449 | 0.1068 | 0.069 | 4 |
| CAL-33 | Head & Neck | 0.5807 | 0.0516 | 0.0204 | 3 |
| HSC-2 | Head & Neck | 0.7659 | 0.0902 | 0.0707 | 3 |
| PCI-15B | Head & Neck | 0.8113 | 0.0605 | 0.0753 | 3 |
| HO-1-N-1 | Head & Neck | 0.9323 | 0.095 | 0.096 | 3 |
| PCI-6A | Head & Neck | 1.1429 | 0.1568 | 0.1195 | 3 |
| H3118 | Head & Neck | 0.8217 | 0.108 | 0.131 | 3 |
| ACC2 | Head & Neck | 1.1233 | 0.1636 | 0.1357 | 3 |
| ACCS | Head & Neck | 0.7258 | 0.2017 | 0.1658 | 3 |
| ACC3 | Head & Neck | 0.887 | 0.186 | 0.168 | 3 |
| BICR 78 | Head & Neck | 1.0035 | 0.1602 | 0.1694 | 3 |
| JR 028 | Head & Neck | 1.0931 | 0.2299 | 0.2027 | 3 |
| PCI-15 | Head & Neck | 1.0668 | 0.1987 | 0.2061 | 3 |
| SCC-9 | Head & Neck | 0.5841 | 0.2727 | 0.272 | 3 |
| SAT | Head & Neck | 0.854 | 0.302 | 0.307 | 3 |
| SCC90 | Head & Neck | 0.5915 | 0.3331 | 0.3358 | 3 |
| HN | Head & Neck | 0.9124 | 0.3981 | 0.3481 | 3 |
| PCI-15A | Head & Neck | 0.8516 | 0.3844 | 0.3675 | 3 |
| JR 013 | Head & Neck | 1.0158 | 0.3829 | 0.3766 | 3 |
| PCI-4B | Head & Neck | 1.2078 | 0.4475 | 0.3808 | 3 |
| PCI-30 | Head & Neck | 0.8216 | 0.362 | 0.4064 | 3 |
| UDSCC2 | Head & Neck | 0.5716 | 0.4203 | 0.4394 | 3 |
| JR 019 | Head & Neck | 1.0805 | 0.4801 | 0.484 | 3 |
| RPMI 2650 | Head & Neck | 1.1239 | 0.5619 | 0.4435 | 2 |
| JR 028EP | Head & Neck | 0.995 | 0.5386 | 0.4657 | 2 |
| BHY | Head & Neck | 1.0468 | 0.5311 | 0.4897 | 2 |
| PCI-4A | Head & Neck | 1.0214 | 0.6602 | 0.4984 | 2 |
| HSC-3 | Head & Neck | 1.069 | 0.3074 | 0.5475 | 1 |
| ACC 8-2 | Head & Neck | 1.1417 | 0.7519 | 0.5967 | 1 |
| JR 022 | Head & Neck | 1.0441 | 0.7332 | 0.6409 | 1 |
| PCI-6B | Head & Neck | 1.1076 | 0.7016 | 0.6703 | 1 |
| ACC112 | Head & Neck | 0.9498 | 0.7645 | 0.916 | 1 |
| GP5d | Intestine | 0.185 | 0.116 | 0.0711 | 5 |
| SW 48 | Intestine | 0.471 | 0.028 | 0.053 | 4 |
| T84 | Intestine | 0.462 | 0.068 | 0.058 | 4 |
| LoVo | Intestine | 0.2792 | 0.0659 | 0.0611 | 4 |
| COLO 205 | Intestine | 0.8137 | 0.0578 | 0.0376 | 3 |
| Hs 257.T | Intestine | 0.8128 | 0.0699 | 0.0465 | 3 |
| MDST8 | Intestine | 0.7601 | 0.094 | 0.0774 | 3 |
| CL-11 | Intestine | 0.9903 | 0.1858 | 0.1559 | 3 |
| SW-948 | Intestine | 1.0249 | 0.2096 | 0.1757 | 3 |
| CoCM-1 | Intestine | 1.062 | 0.227 | 0.191 | 3 |
| LS174T | Intestine | 0.8916 | 0.2634 | 0.2176 | 3 |
| COLO 201 | Intestine | 1.029 | 0.204 | 0.24 | 3 |
| SW620 | Intestine | 0.7593 | 0.2603 | 0.288 | 3 |
| WiDr | Intestine | 0.8917 | 0.3977 | 0.3243 | 3 |
| LS180 | Intestine | 0.9989 | 0.4556 | 0.3266 | 3 |
| SW837 | Intestine | 1.0342 | 0.4365 | 0.3773 | 3 |
| SK-CO-1 | Intestine | 0.93 | 0.464 | 0.405 | 3 |
| CL-14 | Intestine | 0.8508 | 0.6531 | 0.4248 | 2 |
| HRT-18 | Intestine | 0.744 | 0.523 | 0.425 | 2 |
| Caco-2 | Intestine | 0.769 | 0.538 | 0.496 | 2 |
| COLO-206F | Intestine | 1.075 | 0.651 | 0.543 | 1 |
| SW 1417 | Intestine | 1.016 | 0.769 | 0.607 | 1 |
| CL-34 | Intestine | 1.1299 | 0.4878 | 0.6107 | 1 |
| RCM-1 | Intestine | 1.0188 | 0.8159 | 0.6594 | 1 |
| COLO-678 | Intestine | 1.06 | 0.802 | 0.661 | 1 |
| OUMS-23 | Intestine | 0.7971 | 0.9316 | 0.7076 | 1 |
| SW 1116 | Intestine | 1.0852 | 1.0031 | 0.7353 | 1 |
| SW 1463 | Intestine | 1.164 | 0.925 | 0.862 | 1 |
| G-402 | Kidney | 0.4146 | 0.1885 | 0.1583 | 4 |
| SW 156 | Kidney | 0.4381 | 0.3386 | 0.2802 | 4 |
| CAL-54 | Kidney | 0.4808 | 0.3592 | 0.326 | 4 |
| SW 13 | Kidney | 0.697 | 0.014 | 0.023 | 3 |
| G-401 | Kidney | 0.857 | 0.081 | 0.073 | 3 |
| NH-6 | Kidney | 0.9578 | 0.1525 | 0.1175 | 3 |
| KMRM-M1 | Kidney | 1.072 | 0.139 | 0.126 | 3 |
| SN-12C | Kidney | 0.9117 | 0.1661 | 0.1382 | 3 |
| Caki-1 | Kidney | 0.6522 | 0.1373 | 0.1431 | 3 |
| 786-O | Kidney | 1.066 | 0.205 | 0.17 | 3 |
| VMRC-RCW | Kidney | 1.081 | 0.156 | 0.171 | 3 |
| UO-31 | Kidney | 0.8695 | 0.3772 | 0.3758 | 3 |
| 769-P | Kidney | 0.977 | 0.478 | 0.431 | 3 |
| KMRC-20 | Kidney | 0.84 | 0.466 | 0.459 | 3 |
| BFTC-909 | Kidney | 1.076 | 0.4325 | 0.4869 | 3 |
| KMRC-1 | Kidney | 0.8824 | 0.6127 | 0.5558 | 1 |
| VMRC-RCZ | Kidney | 0.9492 | 0.6125 | 0.5913 | 1 |

TABLE 17-continued

Activity of Compound IIa in various solid tumor cell lines.

| Cell Line | Organ | 0.2 nM | 2.0 nM | 20 nM | Sensitivity |
|---|---|---|---|---|---|
| ACHN | Kidney | 1.005 | 0.623 | 0.6277 | 1 |
| JHH-4 | Liver | 0.4019 | 0.0719 | 0.0775 | 4 |
| OCUG-1 | Liver | 0.4247 | 0.115 | 0.0881 | 4 |
| SNU-182 | Liver | 0.3211 | 0.3009 | 0.2618 | 4 |
| SNU-398 | Liver | 0.7925 | 0.0572 | 0.048 | 3 |
| JHH-7 | Liver | 0.526 | 0.0621 | 0.049 | 3 |
| SNU-475 | Liver | 0.9855 | 0.1516 | 0.1274 | 3 |
| JHH-6 | Liver | 0.6033 | 0.1987 | 0.1906 | 3 |
| HuCCT1 | Liver | 0.731 | 0.2303 | 0.1941 | 3 |
| EGI-1 | Liver | 0.8992 | 0.2121 | 0.2415 | 3 |
| huH-1 | Liver | 0.637 | 0.3355 | 0.2569 | 3 |
| SK-HEP-1 | Liver | 0.7567 | 0.2521 | 0.2684 | 3 |
| PLC/PRF/5 | Liver | 0.7758 | 0.2551 | 0.3086 | 3 |
| Hep G2 | Liver | 0.8333 | 0.2949 | 0.311 | 3 |
| SNU-423 | Liver | 0.9714 | 0.304 | 0.3364 | 3 |
| SNU-387 | Liver | 0.6457 | 0.4265 | 0.3953 | 3 |
| JHH-1 | Liver | 0.6947 | 0.4443 | 0.4458 | 3 |
| SNU-449 | Liver | 1.0774 | 0.486 | 0.4864 | 3 |
| C3A | Liver | 0.9439 | 0.4686 | 0.5087 | 1 |
| JHH-2 | Liver | 1.0593 | 0.7702 | 0.7744 | 1 |
| A549 | Lung | 0.4707 | 0.0974 | 0.129 | 4 |
| H290 | Lung | 0.4248 | 0.4081 | 0.3961 | 4 |
| H2691 | Lung | 0.468 | 0.4411 | 0.4795 | 4 |
| RERF-LC-MA | Lung | 0.639 | 0.0854 | 0.0623 | 3 |
| NCI-H841 | Lung | 0.8459 | 0.1149 | 0.1057 | 3 |
| SBC-3 | Lung | 0.9716 | 0.2057 | 0.155 | 3 |
| H2369 | Lung | 1.0518 | 0.172 | 0.1562 | 3 |
| ChaGo-K-1 | Lung | 1.0137 | 0.1936 | 0.1726 | 3 |
| H2804 | Lung | 0.8272 | 0.2981 | 0.195 | 3 |
| NCI-H2286 | Lung | 0.8997 | 0.2979 | 0.2466 | 3 |
| UMC-11 | Lung | 0.6174 | 0.2438 | 0.276 | 3 |
| H2373 | Lung | 0.8795 | 0.3019 | 0.2853 | 3 |
| H2461 | Lung | 0.8732 | 0.3484 | 0.2912 | 3 |
| H2795 | Lung | 1.0282 | 0.3473 | 0.3436 | 3 |
| NCI-H196 | Lung | 0.8976 | 0.3922 | 0.389 | 3 |
| H2722 | Lung | 0.8473 | 0.4877 | 0.4089 | 3 |
| H28 | Lung | 0.9309 | 0.4937 | 0.4124 | 3 |
| H2803 | Lung | 0.6578 | 0.4814 | 0.4939 | 3 |
| H2731 | Lung | 0.9841 | 0.5147 | 0.4912 | 2 |
| H2591 | Lung | 1.0024 | 0.5897 | 0.5288 | 1 |
| SW 1271 | Lung | 1.054 | 0.681 | 0.585 | 1 |
| H2052 | Lung | 0.9018 | 0.7748 | 0.6495 | 1 |
| H513 | Lung | 0.8696 | 0.747 | 0.7763 | 1 |
| NCI-H2195 | Lung | 1.0695 | 0.7473 | 0.7937 | 1 |
| VMRC-LCD | Lung:NSCLC | 0.1083 | 0.0165 | 0.0206 | 5 |
| NCI-H1703 | Lung:NSCLC | 0.0217 | 0.0234 | 0.0387 | 5 |
| DV-90 | Lung:NSCLC | 0.1662 | 0.0939 | 0.0801 | 5 |
| NCI-H520 | Lung:NSCLC | 0.1553 | 0.0853 | 0.0943 | 5 |
| HCC-44 | Lung:NSCLC | 0.4828 | 0.0622 | 0.0573 | 4 |
| LOU-NH91 | Lung:NSCLC | 0.2854 | 0.0649 | 0.0667 | 4 |
| NCI-H1792 | Lung:NSCLC | 0.4287 | 0.1012 | 0.085 | 4 |
| LU99A | Lung:NSCLC | 0.3858 | 0.1388 | 0.1203 | 4 |
| LU99B | Lung:NSCLC | 0.3259 | 0.1927 | 0.1616 | 4 |
| LCLC-103H | Lung:NSCLC | 0.4592 | 0.1711 | 0.163 | 4 |
| NCI-H2009 | Lung:NSCLC | 0.2163 | 0.1481 | 0.1764 | 4 |
| NCI-H2170 | Lung:NSCLC | 0.477 | 0.2033 | 0.1894 | 4 |
| CAL-12T | Lung:NSCLC | 0.4345 | 0.2399 | 0.2003 | 4 |
| SK-MES-1 | Lung:NSCLC | 0.2868 | 0.2316 | 0.2173 | 4 |
| NCI-H2122 | Lung:NSCLC | 0.8339 | 0.0731 | 0.0601 | 3 |
| NCI-H460 | Lung:NSCLC | 0.9368 | 0.0626 | 0.0624 | 3 |
| NCI-H1437 | Lung:NSCLC | 1.0697 | 0.11 | 0.0878 | 3 |
| ABC-1 | Lung:NSCLC | 0.7461 | 0.1129 | 0.0899 | 3 |
| NCI-H1299 | Lung:NSCLC | 0.902 | 0.105 | 0.094 | 3 |
| HCC-366 | Lung:NSCLC | 1.1043 | 0.0917 | 0.1002 | 3 |
| LU65B | Lung:NSCLC | 0.9138 | 0.1102 | 0.1013 | 3 |
| VMRC-LCP | Lung:NSCLC | 0.6195 | 0.1294 | 0.1061 | 3 |
| NCI-H3122 | Lung:NSCLC | 0.664 | 0.1227 | 0.113 | 3 |
| LU65A | Lung:NSCLC | 0.5925 | 0.1313 | 0.1233 | 3 |
| 201T | Lung:NSCLC | 1.1069 | 0.1758 | 0.1239 | 3 |
| EBC-1 | Lung:NSCLC | 0.806 | 0.155 | 0.128 | 3 |
| NCI-H1666 | Lung:NSCLC | 1 | 0.112 | 0.135 | 3 |
| RERF-LC-MS | Lung:NSCLC | 0.6674 | 0.141 | 0.1425 | 3 |
| 273T | Lung:NSCLC | 0.8467 | 0.1865 | 0.159 | 3 |
| NCI-H2110 | Lung:NSCLC | 0.929 | 0.244 | 0.194 | 3 |
| NCI-H2085 | Lung:NSCLC | 1.0485 | 0.2496 | 0.2008 | 3 |
| NCI-H358 | Lung:NSCLC | 1.1308 | 0.2687 | 0.2249 | 3 |
| LU99C | Lung:NSCLC | 0.5091 | 0.1845 | 0.2281 | 3 |
| EPLC-272H | Lung:NSCLC | 0.7924 | 0.2789 | 0.24 | 3 |
| NCI-H2087 | Lung:NSCLC | 0.7317 | 0.2612 | 0.2452 | 3 |
| NCI-H1915 | Lung:NSCLC | 1.1651 | 0.2784 | 0.25 | 3 |
| COR-L23 | Lung:NSCLC | 1.0115 | 0.2364 | 0.2645 | 3 |
| NCI-H1944 | Lung:NSCLC | 0.7625 | 0.2508 | 0.2692 | 3 |
| LU65 | Lung:NSCLC | 1.0552 | 0.3022 | 0.2768 | 3 |
| SW 1573 | Lung:NSCLC | 0.6665 | 0.3095 | 0.2782 | 3 |
| SK-MES | Lung:NSCLC | 0.7978 | 0.3101 | 0.3203 | 3 |
| NCI-H2172 | Lung:NSCLC | 0.9469 | 0.4313 | 0.3324 | 3 |
| NCI-H322 | Lung:NSCLC | 0.5775 | 0.4467 | 0.3978 | 3 |
| NCI-H1623 | Lung:NSCLC | 0.8983 | 0.436 | 0.4131 | 3 |
| NCI-H2030 | Lung:NSCLC | 0.9091 | 0.4382 | 0.4146 | 3 |
| NCI-H1869 | Lung:NSCLC | 0.53 | 0.4401 | 0.4219 | 3 |
| NCI-H1793 | Lung:NSCLC | 0.8914 | 0.4837 | 0.426 | 3 |
| NCI-H2228 | Lung:NSCLC | 1.111 | 0.419 | 0.431 | 3 |
| NCI-H1573 | Lung:NSCLC | 0.5795 | 0.4795 | 0.4416 | 3 |
| HCC-15 | Lung:NSCLC | 1.081 | 0.4963 | 0.4502 | 3 |
| RERF-LC-Ad2 | Lung:NSCLC | 0.5334 | 0.4658 | 0.4902 | 3 |
| NCI-H838 | Lung:NSCLC | 1.043 | 0.5099 | 0.3182 | 2 |
| NCI-H650 | Lung:NSCLC | 1.0045 | 0.5034 | 0.502 | 1 |
| NCI-H2405 | Lung:NSCLC | 0.8472 | 0.497 | 0.5105 | 1 |
| NCI-H2444 | Lung:NSCLC | 0.9104 | 0.601 | 0.5357 | 1 |
| PC-3 [JPC-3] | Lung:NSCLC | 0.7824 | 0.5818 | 0.5439 | 1 |
| NCI-H1693 | Lung:NSCLC | 0.6644 | 0.6313 | 0.5467 | 1 |
| COR-L 105 | Lung:NSCLC | 0.7921 | 0.5136 | 0.5478 | 1 |
| SK-LU-1 | Lung:NSCLC | 0.8993 | 0.5272 | 0.582 | 1 |
| HCC-78 | Lung:NSCLC | 0.865 | 0.666 | 0.595 | 1 |
| H3255 | Lung:NSCLC | 0.894 | 0.686 | 0.598 | 1 |
| NCI-H1781 | Lung:NSCLC | 0.8353 | 0.6108 | 0.6045 | 1 |
| HCC-827 | Lung:NSCLC | 0.8265 | 0.6909 | 0.6187 | 1 |
| HOP92 | Lung:NSCLC | 0.9934 | 0.695 | 0.6344 | 1 |
| Calu-1 | Lung:NSCLC | 0.8105 | 0.6374 | 0.6643 | 1 |
| NCI-H2342 | Lung:NSCLC | 0.8589 | 0.778 | 0.7798 | 1 |
| NCI-H2347 | Lung:NSCLC | 0.9848 | 0.8783 | 0.845 | 1 |
| LC-1 sq | Lung:NSCLC | 1.9116 | 0.996 | 1.2191 | 1 |
| JAR | Miscellaneous | 0.0398 | 0.0104 | 0.0015 | 5 |
| HT 1080 | Miscellaneous | 0.0583 | 0.0135 | 0.0141 | 5 |
| TASK1 | Miscellaneous | 0.8609 | 0.0456 | 0.0344 | 3 |
| GCT | Miscellaneous | 0.6099 | 0.097 | 0.0732 | 3 |
| STS 0421 | Muscle | 0.3838 | 0.1484 | 0.11 | 4 |
| A673 | Muscle | 0.5523 | 0.0896 | 0.0731 | 3 |
| OV-1063 | Ovary | 0.1051 | −0.0465 | −0.0045 | 5 |
| TOV-112D | Ovary | 0.059 | 0.0111 | 0.0122 | 5 |
| A2780 | Ovary | 0.1745 | 0.0693 | 0.0442 | 5 |
| OVMIU | Ovary | 0.1776 | 0.138 | 0.1443 | 5 |
| MDA-H2774 | Ovary | 0.2085 | 0.0117 | 0.0207 | 4 |
| IGROV-1 | Ovary | 0.4271 | 0.1121 | 0.1124 | 4 |
| RMG-I | Ovary | 0.2666 | 0.2123 | 0.1716 | 4 |
| SK-OV-3 | Ovary | 0.2853 | 0.2647 | 0.291 | 4 |
| OAW42 | Ovary | 0.4569 | 0.3872 | 0.3435 | 4 |
| OVTOKO | Ovary | 0.4835 | 0.42 | 0.412 | 4 |
| Caov-3 | Ovary | 0.5251 | −0.0004 | −0.0224 | 3 |
| MCAS | Ovary | 1.2885 | −0.0085 | −0.0142 | 3 |
| PA-1 | Ovary | 0.636 | 0.005 | 0.005 | 3 |
| ES-2 | Ovary | 0.9311 | 0.0747 | 0.0623 | 3 |
| RKN | Ovary | 1.0045 | 0.1482 | 0.1049 | 3 |
| OVCAR-8 | Ovary | 0.7166 | 0.1442 | 0.1224 | 3 |
| A2780ADR | Ovary | 0.5276 | 0.1526 | 0.1356 | 3 |
| TYK-nu | Ovary | 0.7871 | 0.245 | 0.2265 | 3 |
| NIH:OVCAR-3 | Ovary | 1.0723 | 0.2539 | 0.2416 | 3 |
| OAW28 | Ovary | 0.8974 | 0.2001 | 0.2458 | 3 |
| OVCAR-5 | Ovary | 0.7739 | 0.2162 | 0.2648 | 3 |
| EFO-27 | Ovary | 0.8772 | 0.2627 | 0.3237 | 3 |
| SW 626 | Ovary | 1.0372 | 0.3903 | 0.4064 | 3 |
| OVISE | Ovary | 0.6107 | 0.4587 | 0.4191 | 3 |
| OVSAYO | Ovary | 0.9829 | 0.4188 | 0.4195 | 3 |
| EFO-21 | Ovary | 0.8922 | 0.4971 | 0.4502 | 3 |
| OV-90 | Ovary | 1.175 | 0.4593 | 0.4735 | 3 |
| FU-OV-1 | Ovary | 0.9593 | 0.5098 | 0.495 | 2 |
| OVKATE | Ovary | 1.0241 | 0.9374 | 0.8461 | 1 |
| KP-4 | Pancreas | 0.1844 | 0.0203 | 0.0222 | 5 |
| PANC-1 | Pancreas | 0.3146 | 0.1726 | 0.1474 | 4 |
| KP-3 | Pancreas | 0.378 | 0.222 | 0.175 | 4 |
| KP-1N | Pancreas | 0.3155 | 0.1894 | 0.1894 | 4 |
| Panc 03.27 | Pancreas | 0.702 | 0.111 | 0.117 | 3 |

TABLE 17-continued

Activity of Compound IIa in various solid tumor cell lines.

| Cell Line | Organ | 0.2 nM | 2.0 nM | 20 nM | Sensitivity |
|---|---|---|---|---|---|
| HUP-T4 | Pancreas | 0.952 | 0.144 | 0.154 | 3 |
| A2.1 | Pancreas | 1.339 | 0.186 | 0.208 | 3 |
| HPAC | Pancreas | 0.939 | 0.251 | 0.213 | 3 |
| KP-1NL | Pancreas | 0.702 | 0.287 | 0.219 | 3 |
| BxPC-3 | Pancreas | 1.233 | 0.321 | 0.236 | 3 |
| A13A | Pancreas | 1.115 | 0.28 | 0.239 | 3 |
| KP-3L | Pancreas | 0.875 | 0.287 | 0.258 | 3 |
| Panc 10.05 | Pancreas | 1.204 | 0.2845 | 0.267 | 3 |
| HUP-T3 | Pancreas | 0.7682 | 0.2841 | 0.2686 | 3 |
| HPAF-II | Pancreas | 1.042 | 0.423 | 0.372 | 3 |
| DAN-G | Pancreas | 0.6668 | 0.3759 | 0.3811 | 3 |
| KP-2 | Pancreas | 0.8359 | 0.4032 | 0.4095 | 3 |
| YAPC | Pancreas | 0.76 | 0.507 | 0.289 | 2 |
| Capan-1 | Pancreas | 0.857 | 0.51 | 0.368 | 2 |
| Panc 02.03 | Pancreas | 1.0158 | 0.5008 | 0.4159 | 2 |
| AsPC-1 | Pancreas | 1.292 | 0.721 | 0.535 | 1 |
| SU.86.86 | Pancreas | 1.1289 | 0.645 | 0.5435 | 1 |
| PL4 | Pancreas | 0.929 | 0.651 | 0.544 | 1 |
| SUIT-2 | Pancreas | 1.123 | 0.844 | 0.57 | 1 |
| Panc 08.13 | Pancreas | 0.91 | 0.761 | 0.703 | 1 |
| Capan-2 | Pancreas | 1.0128 | 0.7716 | 0.7456 | 1 |
| Panc 04.03 | Pancreas | 0.994 | 0.798 | 0.77 | 1 |
| DU 145 | Prostate | 0.931 | 0.049 | 0.044 | 3 |
| MGH-BA-1 | Skin | 0.15 | 0.044 | −0.013 | 5 |
| WM1158 | Skin | 0.0594 | 0.0252 | 0.0321 | 5 |
| IGR-1 | Skin | 0.1978 | 0.0714 | 0.0587 | 5 |
| COLO-849 | Skin | 0.4553 | −0.0091 | 0.0093 | 4 |
| A2058 | Skin | 0.2671 | 0.0255 | 0.02 | 4 |
| M-14 | Skin | 0.3071 | 0.0703 | 0.0561 | 4 |
| MGH-ST-1 | Skin | 0.4152 | 0.074 | 0.0578 | 4 |
| COLO 792 | Skin | 0.3273 | 0.1011 | 0.0917 | 4 |
| VMRC-MELG | Skin | 0.4605 | 0.1462 | 0.1194 | 4 |
| MGH-BO-1 | Skin | 0.353 | 0.186 | 0.151 | 4 |
| A375.S2 | Skin | 0.452 | 0.1896 | 0.1536 | 4 |
| SK-MEL-39 | Skin | 0.4542 | 0.2968 | 0.2391 | 4 |
| K19 | Skin | 0.323 | 0.3 | 0.247 | 4 |
| IPC-298 | Skin | 0.4501 | 0.3059 | 0.2539 | 4 |
| MGH-SW-1 | Skin | 0.2458 | 0.2558 | 0.271 | 4 |
| A431 | Skin | 1.0122 | 0.022 | 0.0192 | 3 |
| BU-ML | Skin | 0.7451 | 0.0443 | 0.0244 | 3 |
| CHL-1 | Skin | 0.8801 | 0.0514 | 0.0326 | 3 |
| COLO 857 | Skin | 0.7565 | 0.0666 | 0.0529 | 3 |
| SK-MEL-131 | Skin | 0.7317 | 0.0848 | 0.0599 | 3 |
| UACC-62 | Skin | 0.5483 | 0.1094 | 0.124 | 3 |
| Hs 944.T | Skin | 0.7522 | 0.1316 | 0.1388 | 3 |
| MGH-PO-1 | Skin | 0.7752 | 0.1548 | 0.1397 | 3 |
| IGR-37 | Skin | 0.5675 | 0.1714 | 0.1429 | 3 |
| UACC903 | Skin | 0.555 | 0.181 | 0.175 | 3 |
| SK-MEL-37 | Skin | 0.536 | 0.2181 | 0.1784 | 3 |
| MGH-MC-1 | Skin | 0.7186 | 0.1934 | 0.1994 | 3 |
| C32 | Skin | 0.9511 | 0.2482 | 0.2055 | 3 |
| G-MEL | Skin | 0.6624 | 0.2227 | 0.2122 | 3 |
| MEWO | Skin | 0.991 | 0.255 | 0.214 | 3 |
| IGR-39 | Skin | 0.834 | 0.2702 | 0.2141 | 3 |
| MEL-JUSO | Skin | 0.7127 | 0.1949 | 0.2211 | 3 |
| 451Lu | Skin | 0.7217 | 0.2594 | 0.2265 | 3 |
| WM35 | Skin | 0.8726 | 0.2125 | 0.2318 | 3 |
| COLO 858 | Skin | 0.806 | 0.306 | 0.234 | 3 |
| 1205Lu | Skin | 0.5617 | 0.2665 | 0.2484 | 3 |
| K4 | Skin | 0.919 | 0.257 | 0.254 | 3 |
| K1 | Skin | 0.6275 | 0.2832 | 0.2662 | 3 |
| WM793B | Skin | 0.6332 | 0.3606 | 0.3015 | 3 |
| WM 266-4 | Skin | 0.7552 | 0.3436 | 0.3252 | 3 |
| MM608 | Skin | 0.7646 | 0.3161 | 0.3265 | 3 |
| MGH-TH-1 | Skin | 1.114 | 0.4408 | 0.3347 | 3 |
| K2 | Skin | 0.97 | 0.33 | 0.36 | 3 |
| Hs 939.T | Skin | 0.7495 | 0.4148 | 0.3821 | 3 |
| WM164 | Skin | 0.805 | 0.414 | 0.399 | 3 |
| MGH-QU-1 | Skin | 0.97 | 0.46 | 0.433 | 3 |
| SK-MEL-28 | Skin | 0.841 | 0.476 | 0.459 | 3 |
| Hs 940.T | Skin | 0.899 | 0.552 | 0.492 | 2 |
| MEL-HO | Skin | 0.8835 | 0.6098 | 0.5037 | 1 |
| SK-MEL-119 | Skin | 0.8436 | 0.4805 | 0.5052 | 1 |
| HMVII | Skin | 0.7604 | 0.6097 | 0.5073 | 1 |
| K8 | Skin | 0.762 | 0.468 | 0.509 | 1 |
| MGH-MCC-1 | Skin | 1.03 | 0.73 | 0.573 | 1 |
| WM239A | Skin | 1.447 | 0.732 | 0.64 | 1 |
| MM455 | Skin | 1.257 | 0.718 | 0.672 | 1 |
| WM902B | Skin | 1.401 | 0.99 | 0.805 | 1 |
| AGS | Stomach | 0.1829 | 0.0811 | 0.067 | 5 |
| Takigawa | Stomach | 0.1891 | 0.1612 | 0.1255 | 5 |
| TMK-1 | Stomach | 0.334 | 0.0293 | 0.0321 | 4 |
| AZ-521 | Stomach | 0.3819 | 0.0702 | 0.0601 | 4 |
| MKN28 | Stomach | 0.3799 | 0.1106 | 0.0748 | 4 |
| IM-95m | Stomach | 0.4254 | 0.1195 | 0.0834 | 4 |
| KATO II | Stomach | 0.3873 | 0.2237 | 0.2532 | 4 |
| HGC-27 | Stomach | 0.536 | 0.044 | 0.057 | 3 |
| NUGC-3 | Stomach | 1.1004 | 0.09 | 0.0967 | 3 |
| 23132/87 | Stomach | 1.0523 | 0.1618 | 0.1552 | 3 |
| MKN74 | Stomach | 1.0538 | 0.1651 | 0.1667 | 3 |
| KATO III | Stomach | 0.6955 | 0.1991 | 0.196 | 3 |
| RERF-GC-1B | Stomach | 0.8254 | 0.3142 | 0.2073 | 3 |
| MKN7 | Stomach | 1.1909 | 0.2781 | 0.2612 | 3 |
| NCI-N87 | Stomach | 0.8742 | 0.3371 | 0.29 | 3 |
| IM-95 | Stomach | 0.902 | 0.311 | 0.292 | 3 |
| OCUM-1 | Stomach | 0.8101 | 0.2168 | 0.3176 | 3 |
| NUGC-4 | Stomach | 0.5093 | 0.3328 | 0.335 | 3 |
| GTL-16 | Stomach | 0.7105 | 0.4124 | 0.3635 | 3 |
| MKN45 | Stomach | 0.851 | 0.326 | 0.429 | 3 |
| FU97 | Stomach | 0.7699 | 0.5171 | 0.404 | 2 |
| MKN1 | Stomach | 1.024 | 0.5318 | 0.4098 | 2 |
| KMH-2 | Thyroid | 0.343 | 0.017 | 0.0093 | 4 |
| IHH-4 | Thyroid | 0.3912 | 0.0328 | 0.0391 | 4 |
| FTC-133 | Thyroid | 0.3884 | 0.1596 | 0.1535 | 4 |
| 8505C | Thyroid | 0.7694 | 0.1011 | 0.0742 | 3 |
| FTC-238 | Thyroid | 0.5915 | 0.0995 | 0.0877 | 3 |
| CAL-62 | Thyroid | 0.9829 | 0.1362 | 0.1365 | 3 |
| ONCO-DG-1 | Thyroid | 1.0952 | 0.3063 | 0.1977 | 3 |
| TCO-1 | Thyroid | 0.7356 | 0.2228 | 0.1992 | 3 |
| HTC-C3 | Thyroid | 0.7903 | 0.2916 | 0.2857 | 3 |
| TT2609-C02 | Thyroid | 0.9862 | 0.3171 | 0.3136 | 3 |
| 8305C | Thyroid | 0.7851 | 0.435 | 0.3771 | 3 |
| ML-1 | Thyroid | 0.7562 | 0.4193 | 0.4005 | 3 |
| BHT-101 | Thyroid | 1.0259 | 0.4909 | 0.4394 | 3 |
| S-117 | Thyroid | 0.8908 | 0.4405 | 0.4683 | 3 |
| RO82-W-1 | Thyroid | 0.7894 | 0.4013 | 0.4831 | 3 |
| B-CPAP | Thyroid | 1.378 | 0.763 | 0.49 | 2 |
| ASH-3 | Thyroid | 0.7518 | 0.6432 | 0.5762 | 1 |
| MFE-319 | Uterus | 0.2338 | 0.0988 | 0.0843 | 4 |
| HEC-1 | Uterus | 0.2361 | 0.0976 | 0.1034 | 4 |
| SNG-M | Uterus | 0.6532 | 0.0129 | 0.0117 | 3 |
| Ishikawa | Uterus | 0.9421 | 0.0306 | 0.0209 | 3 |
| MFE-296 | Uterus | 0.6434 | 0.0852 | 0.0762 | 3 |
| ESS-1 | Uterus | 0.881 | 0.1059 | 0.0827 | 3 |
| MES-SA | Uterus | 0.808 | 0.1341 | 0.1377 | 3 |
| SKN | Uterus | 0.864 | 0.2716 | 0.1851 | 3 |
| AN3CA | Uterus | 0.9261 | 0.2145 | 0.2207 | 3 |
| Ishikawa (Heraklio) 02 ER- | Uterus | 0.88 | 0.242 | 0.225 | 3 |
| MFE-280 | Uterus | 0.9711 | 0.4052 | 0.3979 | 3 |
| EFE-184 | Uterus | 0.986 | 0.5066 | 0.426 | 2 |
| EN | Uterus | 1.0579 | 0.6322 | 0.5471 | 1 |

Example 14

Compounds of Formula II are Effective Against Many Solid Tumor Cell Lines

Compound IIa was tested against a panel of cell lines derived from hematological malignancies in a cell survival assay using CellTiter-Glo® as a readout after 48 hours in the presence of compound. Table 18 lists the type of hematological malignancy, the name of the sample, its $GI_{50}$ (concentration needed to achieve 50% growth inhibition) value in the assay, the logarithm of the $GI_{50}$ ($\log(GI_{50})$), and the relative sensitivity of each sample (Differential). The differential is calculated by subtracting the $\log(GI_{50})$ for each cell line from the average log($GI_{50}$) across the entire panel (0.236 in this case); a positive value indicates a sample that is more sensitive than average, whereas a negative value indicates a sample that is less sensitive than average.

Sensitive hematological malignancies are: Acute myelogenous leukemia (AML), chronic myelogenous leukemia (CML), acute lymphoblastic leukemia (ALL), multiple myeloma (MM), non-Hodgkin lymphoma (NHL) and Hodgkin lymphoma (HL).

TABLE 18

Activity of Compound IIa in hematological cancer cell lines.

| Disease | Cell Line | $GI_{50}$ (nM) | Log($GI_{50}$) | Differential |
|---|---|---|---|---|
| AML | MV4; 11 | 0.08 | −1.114 | 0.747 |
| AML | MV4; 11Luc | 0.11 | −0.979 | 0.613 |
| AML | AML-193 | 0.11 | −0.959 | 0.593 |
| AML | Kasumi-1 | 0.44 | −0.357 | −0.010 |
| AML | UKE-1 | 0.18 | −0.757 | 0.391 |
| AML | SET-2 | 0.34 | −0.469 | 0.102 |
| AML | MOLM13-Luc | 0.23 | −0.645 | 0.279 |
| AML | HL60 | 0.17 | −0.783 | 0.416 |
| AML | HL60-Luc | 0.51 | −0.294 | −0.072 |
| AML | HEL92 | 0.49 | −0.310 | −0.056 |
| CML | K562 | 0.21 | −0.680 | 0.314 |
| ALL | CCRF-CEM | 0.16 | −0.785 | 0.419 |
| ALL | RS4; 11 | 0.10 | −1.000 | 0.634 |
| ALL | MOLT-4 | 0.33 | −0.480 | 0.114 |
| ALL | SEM-Luc | 0.15 | −0.824 | 0.458 |
| ALL | MOLT-3 | 0.34 | −0.475 | 0.109 |
| ALL | REH | 0.18 | −0.745 | 0.379 |
| ALL | SUP-B15 | 0.19 | −0.721 | 0.355 |
| ALL | CCRF-HSB-2 | 0.19 | −0.733 | 0.367 |
| ALL | 697 | 0.11 | −0.979 | 0.613 |
| ALL | NALM-6 | 0.14 | −0.870 | 0.504 |
| ALL | NALM-19 | 0.19 | −0.721 | 0.355 |
| ALL | TANOUE | 10.00 | 1.000 | −1.366 |
| ALL | MHH-CALL-2 | 0.32 | −0.502 | 0.136 |
| ALL | MHH-CALL-3 | 0.20 | −0.699 | 0.333 |
| ALL | MHH-CALL-4 | 10.00 | 1.000 | −1.366 |
| ALL | MUTZ-5 | 10.00 | 1.000 | −1.366 |
| ALL | YT | 10.00 | 1.000 | −1.366 |
| MM | KMS11 | 0.48 | −0.316 | −0.050 |
| MM | KMS11-Luc | 0.29 | −0.538 | 0.172 |
| MM | KMS18-Luc | 0.52 | −0.286 | −0.080 |
| MM | OPM2 | 0.14 | −0.870 | 0.504 |
| MM | MM1-S | 0.24 | −0.620 | 0.254 |
| MM | MM1-S-Luc | 0.23 | −0.638 | 0.272 |
| MM | KMS26 | 0.24 | −0.620 | 0.254 |
| MM | KMS12 | 0.29 | −0.538 | 0.172 |
| MM | L363 | 0.13 | −0.886 | 0.520 |
| MM | LP1 | 0.21 | −0.688 | 0.322 |
| MM | INA-6 | 0.12 | −0.921 | 0.555 |
| MM | RPMI8226 | 0.26 | −0.582 | 0.216 |
| MM | H929 | 0.34 | −0.475 | 0.109 |
| MM | H929-Luc | 1.69 | 0.227 | −0.593 |
| NHL | RL | 20.00 | 1.301 | −1.667 |
| NHL | SuDHL-1 | 10.00 | 1.000 | −1.366 |
| NHL | SuDHL-4 | 0.45 | −0.350 | −0.016 |
| NHL | SuDHL-6 | 0.16 | −0.796 | 0.430 |
| NHL | U937 | 0.20 | −0.699 | 0.333 |
| NHL | SR | 0.11 | −0.957 | 0.591 |
| NHL | Karpas-299-Luc | 20.18 | 1.305 | −1.671 |
| NHL | Karpas-299 | 0.20 | −0.699 | 0.333 |
| NHL | Karpas-422 | 5.14 | 0.711 | −1.077 |
| NHL | Ramos | 0.16 | −0.796 | 0.430 |
| NHL | HuT78 | 0.28 | −0.561 | 0.195 |
| NHL | HH | 0.22 | −0.668 | 0.301 |
| NHL | DEL | 0.28 | −0.548 | 0.182 |
| NHL | SUP-M2 | 0.18 | −0.745 | 0.379 |
| NHL | DOHH2 | 0.24 | −0.629 | 0.263 |
| NHL | SUP-T1 | 5.57 | 0.746 | −1.112 |
| HL | HDLM-2 | 0.12 | −0.921 | 0.555 |
| HL | L-1236 | 3.67 | 0.564 | −0.930 |
| HL | L428 | 20.00 | 1.301 | −1.667 |

TABLE 18-continued

Activity of Compound IIa in hematological cancer cell lines.

| Disease | Cell Line | $GI_{50}$ (nM) | Log($GI_{50}$) | Differential |
|---|---|---|---|---|
| HL | KM-H2 | 0.23 | −0.632 | 0.266 |
|  | Mean | 0.430 | −0.366 |  |

That which is claimed:

1. A compound of formula (II):

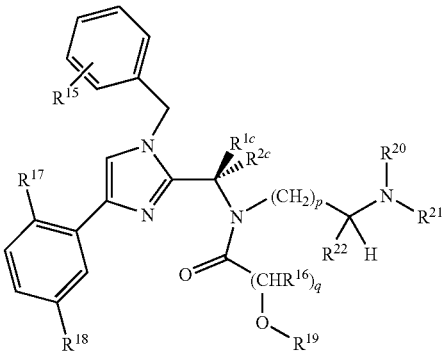

(II)

wherein:
$R^{1c}$ is selected from the group consisting of ethyl, isopropyl, t-butyl, phenyl, —CH(CH$_2$)$_2$O (oxetan-3-yl) and —CCH$_3$(CH$_2$)$_2$O (3-methyloxetan-3-yl);
$R^{2c}$ is hydrogen;
$R^{15}$ and $R^{16}$ are each independently selected from H, halo, C1-4 alkyl, C1-4 haloalkyl, and CN;
$R^{17}$ and $R^{18}$ are each halo;
$R^{19}$, $R^{20}$ and $R^{21}$ are each independently H or optionally substituted C1-C10 acyl;
$R^{22}$ is C1-C4 haloalkyl;
p is 2;
q is 1
or a pharmaceutically acceptable salt thereof.

2. The compound of claim 1, wherein $R^{22}$ is fluoromethyl.
3. The compound of any of claims 1-2, wherein $R^{15}$ is H.
4. The compound of claim 3, wherein $R^{20}$ and $R^{21}$ are each H.
5. The compound of any of claim 1-2, 3 or 4, wherein $R^{19}$ is H.
6. The compound of any of claim 1-2, 3 or 4, wherein $R^{19}$ is optionally substituted C1-C10 acyl.
7. A compound of Formula IIIb:

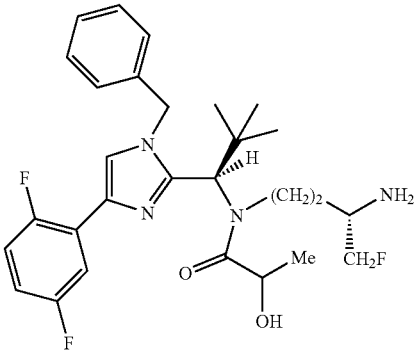

IIb or a pharmaceutically acceptable salt thereof.

8. A compound of formula IIIa:
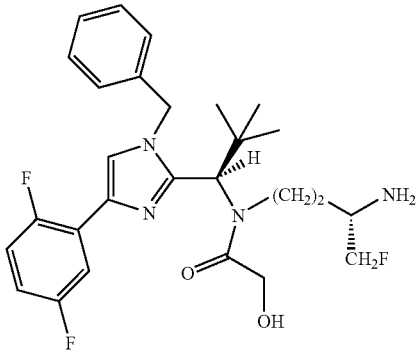
or a pharmaceutically acceptable salt thereof.
9. A compound of formula IIIc:
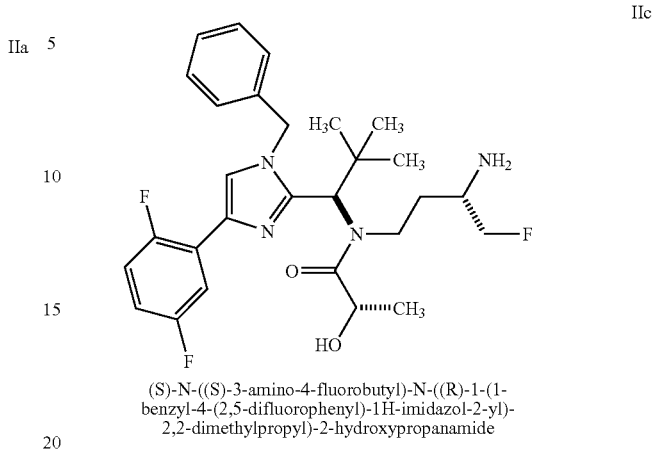
(S)-N-((S)-3-amino-4-fluorobutyl)-N-((R)-1-(1-benzyl-4-(2,5-difluorophenyl)-1H-imidazol-2-yl)-2,2-dimethylpropyl)-2-hydroxypropanamide
or a pharmaceutically acceptable salt thereof.
* * * * *